:::

(12) United States Patent
Harikrishnan et al.

(10) Patent No.: US 10,399,987 B2
(45) Date of Patent: Sep. 3, 2019

(54) TGF BETA RECEPTOR ANTAGONISTS

(71) Applicant: BRISTOL-MYERS SQUIBB COMPANY, Princeton, NJ (US)

(72) Inventors: Lalgudi S. Harikrishnan, Skillman, NJ (US); Brian E. Fink, Yardley, PA (US); Robert M. Borzilleri, Carversville, PA (US); Gopikishan Tonukunuru, Bangalore (IN); Jayakumar Sankara Warrier, Bangalore (IN)

(73) Assignee: Bristol-Myer Squibb Company, Princeton, NJ (US)

( * ) Notice: Subject to any disclaimer, the term of this patent is extended or adjusted under 35 U.S.C. 154(b) by 0 days.

(21) Appl. No.: 15/747,843

(22) PCT Filed: Jul. 27, 2016

(86) PCT No.: PCT/US2016/044233
§ 371 (c)(1),
(2) Date: Jan. 26, 2018

(87) PCT Pub. No.: WO2017/019757
PCT Pub. Date: Feb. 2, 2017

(65) Prior Publication Data
US 2018/0215762 A1    Aug. 2, 2018

Related U.S. Application Data

(60) Provisional application No. 62/197,667, filed on Jul. 28, 2015.

(51) Int. Cl.
| | | |
|---|---|---|
| *C07D 487/04* | (2006.01) | |
| *A61P 35/00* | (2006.01) | |
| *A61K 31/519* | (2006.01) | |

(52) U.S. Cl.
CPC .......... *C07D 487/04* (2013.01); *A61K 31/519* (2013.01); *A61P 35/00* (2018.01)

(58) Field of Classification Search
CPC ............................ C07D 487/04; A61K 31/519
See application file for complete search history.

(56) References Cited

U.S. PATENT DOCUMENTS 7,223,766 B2 *  5/2007  Dugar .................. A61K 31/517
                                                          514/258.1

FOREIGN PATENT DOCUMENTS

| WO | WO 2004/021979 A2 | 3/2004 |
|---|---|---|
| WO | WO 2004/081009 A1 | 9/2004 |
| WO | 2004087056 A2 * | 10/2004 |
| WO | WO 2004/087056 A2 | 10/2004 |

\* cited by examiner

*Primary Examiner* — Alexander R Pagano
*Assistant Examiner* — Ebenezer O Sackey
(74) *Attorney, Agent, or Firm* — Elliott Korsen

(57) ABSTRACT

The invention relates generally to compounds that modulate the activity of TGFβR-1 and TGFβR-2, pharmaceutical compositions containing said compounds and methods of treating proliferative disorders and disorders of dysregulated apoptosis, such as cancer, utilizing the compounds of the invention.

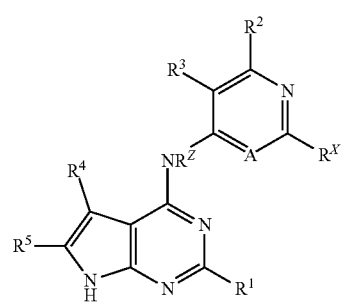

(I)

11 Claims, No Drawings

TGF BETA RECEPTOR ANTAGONISTS

CROSS-REFERENCE TO RELATED APPLICATIONS

This application claims the benefit of U.S. Provisional Application No. 62/197,667, filed Jul. 28, 2015, the disclosure of which is incorporated herein by reference in its entirety.

FIELD OF THE INVENTION

The invention relates generally to compounds that modulate the activity of TGFβR-1 and TGFβR-2, pharmaceutical compositions containing said compounds and methods of treating proliferative disorders and disorders of dysregulated apoptosis, such as cancer, utilizing the compounds of the invention.

BACKGROUND OF THE INVENTION

TGFβ is a multifunctional cytokine that regulates a wide variety of biological processes that include cell proliferation and differentiation, migration and adhesion, extracellular matrix modification including tumor stroma and immunosuppression, angiogenesis and desmoplasia (Ling and lee, Current Pharmaceutical Biotech. 2011, 12:2190-2202), processes supporting tumor progression and late stage disease.

The active form of TGFβ is a dimer that signals through the formation of a membrane bound heterotetramer composed of the serine threonine type 1 and type 2 receptors, TGFβR-1 (ALK5) and TGFβR-2, respectively. Upon binding of two type 1 and two type 2 receptors, the type 2 constitutively activated receptors phosphorylate the type 1 receptors in the glycine and serine rich "GS region" activating a signaling cascade through the intracellular signaling effector molecules, Smad2 or Smad3. TGFβR-1 phosphorylates the receptor Smad2 and/or Smad3 (RSmads) that form a complex with Smad4 (Shi and Massague, Cell 2003, 113:685-700). These complexes then translocate to the nucleus where they elicit a wide variety of transcriptional responses resulting in altered gene expression (Weiss and Attisano, WIREs Developmental Biology, 2013, 2:47-63). The TGFβ proteins are prototypic members of a large family of related factors in mammals with a number of these also identified in other phyla. Generally, two groups have been characterized, the TGFβ-like and BMP-like ligands. In addition, in vertebrates, seven type1 receptors and five type 2 receptors have been identified. An additional layer of complexity in ligand/receptor binding is the potential of co-receptors known as type 3, that facilitate ligand binding to the type 1 and 2 receptor complex. These type 3 receptors, also known as Betaglycan and Endoglin are comprised of large extracellular domains and short cytoplasmic tails and bind different TGFβ family members (Bernabeu et al., Biochem Biophys Acta 2009, 1792:954-73). Although type 3 receptors facilitate signaling, cleavage of the extracellular domain can generate soluble proteins that sequester ligands and can potentially inhibit signaling (Bernabeu et al., Biochem Biophys Acta 2009, 1792:954-73). While multiple redundancies in this large family present challenges to identifying a selective inhibitor, TGFβR-1 and -2 are relatively selective targets for TGFβ ligand engagement.

Alteration in TGFβ signaling are associated with a wide variety of human disorders including fibrosis, inflammatory, skeletal, muscular and cardiovascular disorders as well as cancer (Harradine, et al, 2006, Annals of Medicine 38:403-14). In human cancer, TGFβ signaling alterations can occur in the germline or arise spontaneously in various cancer types. TGFβ is also a potent inducer of angiogenesis, which provides a critical support system for solid tumors as well as a mechanism for tumor cell dissemination (Buijs et al., 2011, Curr Pharmaceutical Biotech, 12:2121-37). Therefore multiple strategies to inhibit TGFβ signaling have been exploited in various disease states.

SUMMARY OF THE INVENTION

In a first aspect of the present invention, there is provided a compound of formula (I)

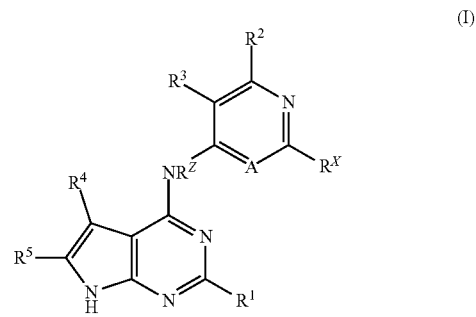

wherein:
A is $CR^y$ or N;
$R^1$ is aryl or heteroaryl, substituted with 0-5 $R^6$;
$R^2$ is hydrogen, a 5-8 membered heterocyclic ring containing 1-4 heteroatoms selected from —O—, —S— or —N—, $NHSO_2R^7$ or $NHCOR^7$;
$R^3$ is hydrogen, halogen, $(C_1-C_3)$alkyl, $(C_1-C_3)$alkoxy, —$CONR^8R^9$ or —$OR^{10}$; or
$R^3$ and the —NH— linker group are taken together to form a 10-12 membered heterobicyclic ring containing 1-4 heteroatoms selected from —O—, —S— or —N—;
$R^4$ is $(C_1-C_6)$alkyl, —$CH_2NR^{11}R^{12}$ or —$CONR^{11}R^{12}$;
$R^5$ is hydrogen, —$CONHR^{13}$, —$CH_2NHR^{14}R^{15}$ or —$NHR^{14}R^{15}$;
$R^x$ is hydrogen, halogen, $(C_1-C_6)$alkyl or —$NHCO(C_1-C_6)$alkyl;
$R^y$ is hydrogen or halogen;
$R^z$ is hydrogen or $(C_1-C_3)$alkyl;
$R^6$ is hydrogen, halogen, $(C_1-C_6)$alkyl, $(C_1-C_6)$alkoxy, —$CHF_2$, —$CFH_2$, $CF_3$, $(C_3-C_8)$cycloalkyl, —$NH_2$ or $NHSO_2(C_1-C_6)$alkyl;
$R^7$ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;
$R^8$ is hydrogen, $(C_1-C_6)$alkoxy or $(C_1-C_6)$alkyl;
$R^9$ is hydrogen or a 5-8 membered heterocyclic ring containing 1-4 heteroatoms selected from —O—, —S— or —N—; or
$R^8$ and $R^9$ are taken together with the nitrogen to which they are attached to form a 5-8 membered heterocyclic ring containing 1-4 heteroatoms selected from —O—, —S— or —N—;
$R^{10}$ is $(C_1-C_6)$alkyl;
$R^{11}$ is hydrogen, amino$(C_1-C_6)$alkyl or hydroxy$(C_1-C_6)$alkyl;
$R^{12}$ is hydrogen, amino$(C_1-C_6)$alkyl or hydroxy$(C_1-C_6)$alkyl; or $R^{11}$ and $R^{12}$ are taken together with the nitrogen to which they are attached to form a 5-8 membered heterocyclic ring containing 1-4 heteroatoms selected from —O—, —S— or —N—;

$R^{13}$ is hydrogen or $(C_1-C_6)$alkyl;
$R^{14}$ is hydrogen or $(C_1-C_6)$alkyl
$R^{15}$ is hydrogen or $(C_1-C_6)$alkyl; or
$R^{14}$ and $R^{15}$ are taken together with the nitrogen to which they are attached to form a 5-8 membered heterocyclic ring containing 1-4 heteroatoms selected from —O—, —S— or —N—;

or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, there is provided a compound of the invention for use in the treatment of a disease or condition for which a TGFβR antagonist is indicated.

In another aspect, there is provided a method of treating cancers, fibrosis, inflammatory, skeletal, muscular and cardiovascular disorders which comprise administering to a subject in need thereof a therapeutically effective amount of a TGFβR antagonist.

DETAILED DESCRIPTION OF THE INVENTION

In a first aspect of the present invention, there is provided a compound of formula (I)

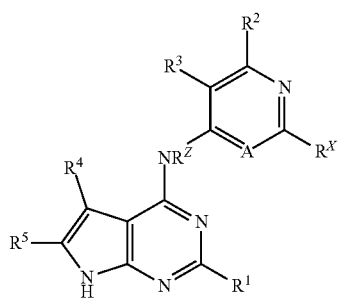

(I)

wherein:
A is $CR^y$ or N;
$R^1$ is aryl or heteroaryl, substituted with 0-5 $R^6$;
$R^2$ is hydrogen, a 5-8 membered heterocyclic ring containing 1-4 heteroatoms selected from —O—, —S— or —N—, $NHSO_2R^7$ or $NHCOR^7$;
$R^3$ is hydrogen, halogen, $(C_1-C_3)$alkyl, $(C_1-C_3)$alkoxy, —$CONR^8R^9$ or —$OR^{10}$; or
$R^3$ and the —NH— linker group are taken together to form a 10-12 membered heterobicyclic ring containing 1-4 heteroatoms selected from —O—, —S— or —N—;
$R^4$ is $(C_1-C_6)$alkyl, —$CH_2NR^{11}R^{12}$ or —$CONR^{11}R^{12}$;
$R^5$ is hydrogen, —$CONHR^{13}$, —$CH_2NHR^{14}R^{15}$ or —$NHR^{14}R^{15}$;
$R^x$ is hydrogen, halogen, $(C_1-C_6)$alkyl or —$NHCO(C_1-C_6)$alkyl;
$R^y$ is hydrogen or halogen;
$R^z$ is hydrogen or $(C_1-C_3)$alkyl;

$R^6$ is hydrogen, halogen, $(C_1-C_6)$alkyl, $(C_1-C_6)$alkoxy, —$CHF_2$, —$CFH_2$, $CF_3$, $(C_3-C_8)$cycloalkyl, —$NH_2$ or $NHSO_2(C_1-C_6)$alkyl;
$R^7$ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;
$R^8$ is hydrogen, $(C_1-C_6)$alkoxy or $(C_1-C_6)$alkyl;
$R^9$ is hydrogen or a 5-8 membered heterocyclic ring containing 1-4 heteroatoms selected from —O—, —S— or —N—; or
$R^8$ and $R^9$ are taken together with the nitrogen to which they are attached to form a 5-8 membered heterocyclic ring containing 1-4 heteroatoms selected from —O—, —S— or —N—;
$R^{10}$ is $(C_1-C_6)$alkyl;
$R^{11}$ is hydrogen, amino$(C_1-C_6)$alkyl or hydroxy$(C_1-C_6)$alkyl;
$R^{12}$ is hydrogen, amino$(C_1-C_6)$alkyl or hydroxy$(C_1-C_6)$alkyl; or
$R^{11}$ and $R^{12}$ are taken together with the nitrogen to which they are attached to form a 5-8 membered heterocyclic ring containing 1-4 heteroatoms selected from —O—, —S— or —N—;
$R^{13}$ is hydrogen or $(C_1-C_6)$alkyl;
$R^{14}$ is hydrogen or $(C_1-C_6)$alkyl
$R^{15}$ is hydrogen or $(C_1-C_6)$alkyl; or
$R^{14}$ and $R^{15}$ are taken together with the nitrogen to which they are attached to form a 5-8 membered heterocyclic ring containing 1-4 heteroatoms selected from —O—, —S— or —N—;

or a pharmaceutically acceptable salt, tautomer or stereoisomer thereof.

In a second aspect within the scope of the first aspect of the invention, there is provided a compound of formula (II)

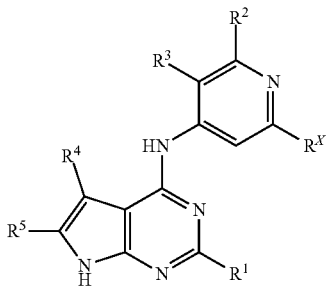

(II)

$R^1$ is aryl or heteroaryl, substituted with 0-3 $R^6$;
$R^2$ is hydrogen, a 5-8 membered heterocyclic ring containing 1-4 heteroatoms selected from —O—, —S— or —N—, $NHSO_2R^7$ or $NHCOR^7$;
$R^3$ is hydrogen, halogen, $(C_1-C_3)$alkyl, $(C_1-C_3)$alkoxy, —$CONR^8R^9$ or —$OR^{10}$; or
$R^3$ and the —NH— linker group are taken together to form a 10-12 membered heterobicyclic ring containing 1-4 heteroatoms selected from —O—, —S— or —N—;
$R^4$ is $(C_1-C_6)$alkyl, —$CH_2NR^{11}R^{12}$ or —$CONR^{11}R^{12}$;
$R^5$ is hydrogen, —$CONHR^{13}$, —$CH_2NHR^{14}R^{15}$ or —$NHR^{14}R^{15}$;
$R^x$ is hydrogen, halogen, $(C_1-C_6)$alkyl or —$NHCO(C_1-C_6)$alkyl;
$R^6$ is hydrogen, halogen, $(C_1-C_6)$alkyl, $(C_1-C_6)$alkoxy, —$CHF_2$, —$CFH_2$, $CF_3$, $(C_3-C_8)$cycloalkyl, —$NH_2$ or $NHSO_2(C_1-C_6)$alkyl;

$R^7$ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;

$R^8$ is hydrogen, $(C_1-C_6)$alkoxy or $(C_1-C_6)$alkyl;

$R^9$ is hydrogen or a 5-8 membered heterocyclic ring containing 1-4 heteroatoms selected from —O—, —S— or —N—; or $R^8$ and $R^9$ are taken together with the nitrogen to which they are attached to form a 5-8 membered heterocyclic ring containing 1-4 heteroatoms selected from —O—, —S— or —N—;

$R^{10}$ is $(C_1-C_6)$alkyl;

$R^{11}$ is hydrogen, amino$(C_1-C_6)$alkyl or hydroxy$(C_1-C_6)$alkyl;

$R^{12}$ is hydrogen, amino$(C_1-C_6)$alkyl or hydroxy$(C_1-C_6)$alkyl; or $R^{11}$ and $R^{12}$ are taken together with the nitrogen to which they are attached to form a 5-8 membered heterocyclic ring containing 1-4 heteroatoms selected from —O—, —S— or —N—;

$R^{13}$ is hydrogen or $(C_1-C_6)$alkyl;

$R^{14}$ is hydrogen or $(C_1-C_6)$alkyl $R^{15}$ is hydrogen or $(C_1-C_6)$alkyl; or $R^{14}$ and $R^{15}$ are taken together with the nitrogen to which they are attached to form a 5-8 membered heterocyclic ring containing 1-4 heteroatoms selected from —O—, —S— or —N—;

or a pharmaceutically acceptable salt, tautomer or stereoisomer thereof.

In a third aspect of the invention, there is provided a compound of formula (III)

wherein:

$R^2$ is hydrogen, pyrrolidin-2-one, NHSO$_2$R$^7$ or NHCOR$^7$;

$R^3$ is hydrogen, halogen, $(C_1-C_3)$alkyl, $(C_1-C_3)$alkoxy, —CONR$^8$R$^9$ or —OR$^{10}$; or $R^3$ and the —NH— linker group are taken together to form a 10-12 membered heterobicyclic ring containing 1-4 heteroatoms selected from —O—, —S— or —N—;

$R^4$ is $(C_1-C_6)$alkyl, —CH$_2$NR$^{11}$R$^{12}$ or —CONR$^{11}$R$^{12}$;

$R^5$ is hydrogen, —CONHR$^{13}$, —CH$_2$NHR$^{14}$R$^{15}$ or —NHR$^{14}$R$^{15}$;

$R^x$ is hydrogen, halogen, $(C_1-C_6)$alkyl or —NHCO$(C_1-C_6)$alkyl;

$R^6$ is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;

$R^7$ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;

$R^8$ is hydrogen, $(C_1-C_6)$alkoxy or $(C_1-C_6)$alkyl;

$R^9$ is hydrogen or a 5-8 membered heterocyclic ring containing 1-4 heteroatoms selected from —O—, —S— or —N—; or $R^8$ and $R^9$ are taken together with the nitrogen to which they are attached to form a 5-8 membered heterocyclic ring containing 1-4 heteroatoms selected from —O—, —S— or —N—;

$R^{10}$ is $(C_1-C_6)$alkyl;

$R^{11}$ is hydrogen, amino$(C_1-C_6)$alkyl or hydroxy$(C_1-C_6)$alkyl;

$R^{12}$ is hydrogen, amino$(C_1-C_6)$alkyl or hydroxy$(C_1-C_6)$alkyl; or $R^{11}$ and $R^{12}$ are taken together with the nitrogen to which they are attached to form a 5-8 membered heterocyclic ring containing 1-4 heteroatoms selected from —O—, —S— or —N—;

$R^{13}$ is hydrogen or $(C_1-C_6)$alkyl;

$R^{14}$ is hydrogen or $(C_1-C_6)$alkyl $R^{15}$ is hydrogen or $(C_1-C_6)$alkyl; or $R^{14}$ and $R^{15}$ are taken together with the nitrogen to which they are attached to form a 5-8 membered heterocyclic ring containing 1-4 heteroatoms selected from —O—, —S— or —N—;

n is 0, 1, 2 or 3;

or a pharmaceutically acceptable salt, tautomer or stereoisomer thereof.

In a fourth aspect of the invention, there is provided a compound of formula (III)

wherein:

$R^2$ is hydrogen, pyrrolidin-2-one, NHSO$_2$R$^7$ or NHCOR$^7$;

$R^3$ is hydrogen, halogen, $(C_1-C_3)$alkyl, $(C_1-C_3)$alkoxy, —CONR$^8$R$^9$ or —OR$^{10}$; or $R^3$ and the —NH— linker group are taken together to form a 10-12 membered heterobicyclic ring containing 1-4 heteroatoms selected from —O—, —S— or —N—;

$R^4$ is $(C_1-C_6)$alkyl, —CH$_2$NR$^{11}$R$^{12}$ or —CONR$^{11}$R$^{12}$;

$R^5$ is hydrogen, —CONHR$^{13}$, —CH$_2$NHR$^{14}$R$^{15}$ or —NHR$^{14}$R$^{15}$;

$R^x$ is hydrogen, halogen, $(C_1-C_6)$alkyl or —NHCO$(C_1-C_6)$alkyl;

$R^6$ is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;

$R^7$ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;

$R^8$ is hydrogen, $(C_1-C_6)$alkoxy or $(C_1-C_6)$alkyl;

$R^9$ is hydrogen or a 5-8 membered heterocyclic ring containing 1-4 heteroatoms selected from —O—, —S— or —N—; or R[8] and R[9] are taken together with the nitrogen to which they are attached to form a 5-8 membered heterocyclic ring containing 1-4 heteroatoms selected from —O—, —S— or —N—;

R[10] is $(C_1-C_6)$alkyl;

R[11] is hydrogen, amino$(C_1-C_6)$alkyl or hydroxy$(C_1-C_6)$alkyl;

R[12] is hydrogen, amino$(C_1-C_6)$alkyl or hydroxy$(C_1-C_6)$alkyl; or

R[11] and R[12] are taken together with the nitrogen to which they are attached to form a 5-8 membered heterocyclic ring containing 1-4 heteroatoms selected from —O—, —S— or —N—;

R[13] is hydrogen or $(C_1-C_6)$alkyl;

R[14] is hydrogen or $(C_1-C_6)$alkyl

R[15] is hydrogen or $(C_1-C_6)$alkyl; or

R[14] and R[15] are taken together with the nitrogen to which they are attached to form a 5-8 membered heterocyclic ring containing 1-4 heteroatoms selected from —O—, —S— or —N—;

n is 0, 1 or 2;

or a pharmaceutically acceptable salt, tautomer or stereoisomer thereof.

In a fifth aspect of the invention, there is provided a compound of formula (III)

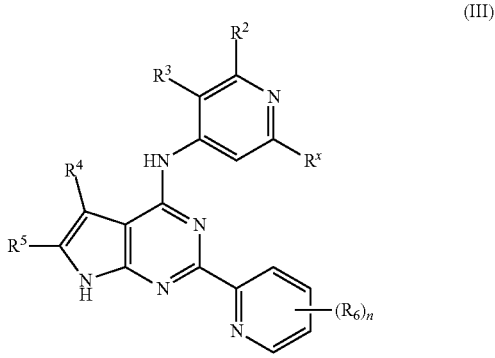

(III)

wherein:

R[2] is hydrogen, pyrrolidin-2-one, NHSO$_2$R[7] or NHCOR[7];

R[3] is hydrogen, halogen, $(C_1-C_3)$alkyl, $(C_1-C_3)$alkoxy, —CONR[8]R[9] or —OR[10]; or R[3] and the —NH— linker group are taken together to form a 10-12 membered heterobicyclic ring containing 1-4 heteroatoms selected from —O—, —S— or —N—;

R[4] is $(C_1-C_6)$alkyl, —CH$_2$NR[11]R[12] or —CONR[11]R[12];

R[5] is hydrogen, —CONHR[13], —CH$_2$NHR[14]R[15] or —NHR[14]R[15];

R[x] is hydrogen, halogen, $(C_1-C_6)$alkyl or —NHCO$(C_1-C_6)$alkyl;

R[6] is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;

R[7] is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;

R[8] is hydrogen, $(C_1-C_6)$alkoxy or $(C_1-C_6)$alkyl;

R[9] is hydrogen or a 5-8 membered heterocyclic ring containing 1-4 heteroatoms selected from —O—, —S— or —N—; or R[8] and R[9] are taken together with the nitrogen to which they are attached to form a 5-8 membered heterocyclic ring containing 1-4 heteroatoms selected from —O—, —S— or —N—;

R[10] is $(C_1-C_6)$alkyl;

R[11] is hydrogen, amino$(C_1-C_6)$alkyl or hydroxy$(C_1-C_6)$alkyl;

R[12] is hydrogen, amino$(C_1-C_6)$alkyl or hydroxy$(C_1-C_6)$alkyl; or

R[11] and R[12] are taken together with the nitrogen to which they are attached to form a 5-8 membered heterocyclic ring containing 1-4 heteroatoms selected from —O—, —S— or —N—;

R[13] is hydrogen or $(C_1-C_6)$alkyl;

R[14] is hydrogen or $(C_1-C_6)$alkyl

R[15] is hydrogen or $(C_1-C_6)$alkyl; or

R[14] and R[15] are taken together with the nitrogen to which they are attached to form a 5-8 membered heterocyclic ring containing 1-4 heteroatoms selected from —O—, —S— or —N—;

n is 0 or 1;

or a pharmaceutically acceptable salt, tautomer or stereoisomer thereof.

In a sixth aspect of the invention, there is provided a compound of formula (III)

wherein:

R[2] is hydrogen, pyrrolidin-2-one, NHSO$_2$R[7] or NHCOR[7];

R[3] is hydrogen, halogen, $(C_1-C_3)$alkyl, $(C_1-C_3)$alkoxy, —CONR[8]R[9] or —OR[10]; or R[3] and the —NH— linker group are taken together to form a 10-12 membered heterobicyclic ring containing 1-4 heteroatoms selected from —O—, —S— or —N—;

R[4] is $(C_1-C_6)$alkyl, —CH$_2$NR[11]R[12] or —CONR[11]R[12];

R[5] is hydrogen, —CONHR[13], —CH$_2$NHR[14]R[15] or —NHR[14]R[15];

R[x] is hydrogen, halogen, $(C_1-C_6)$alkyl or —NHCO$(C_1-C_6)$alkyl;

R[6] is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;

R[7] is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;

R[8] is hydrogen, $(C_1-C_6)$alkoxy or $(C_1-C_6)$alkyl;

R[9] is hydrogen or a 5-8 membered heterocyclic ring containing 1-4 heteroatoms selected from —O—, —S— or —N—; or R[8] and R[9] are taken together with the nitrogen to which they are attached to form a 5-8 membered heterocyclic ring containing 1-4 heteroatoms selected from —O—, —S— or —N—;

R[10] is $(C_1-C_6)$alkyl;

R[11] is hydrogen, amino$(C_1-C_6)$alkyl or hydroxy$(C_1-C_6)$alkyl;

R[12] is hydrogen, amino$(C_1-C_6)$alkyl or hydroxy$(C_1-C_6)$alkyl;

R[13] is hydrogen or $(C_1-C_6)$alkyl;

R[14] is hydrogen or $(C_1-C_6)$alkyl

R[15] is hydrogen or $(C_1-C_6)$alkyl;

n is 0 or 1;

or a pharmaceutically acceptable salt, tautomer or stereoisomer thereof.

In a seventh aspect of the invention, there is provided a compound of formula (III)

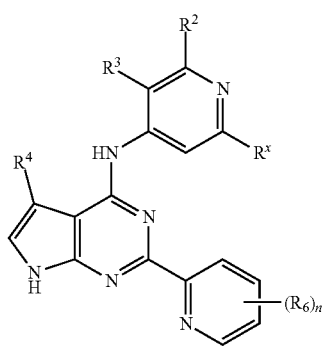

wherein:
R² is hydrogen or NHCOR⁷;
R³ is hydrogen, halogen, (C₁-C₃)alkyl, (C₁-C₃)alkoxy, —CONR⁸R⁹ or —OR¹⁰;
R⁴ is (C₁-C₆)alkyl, —CH₂NR¹¹R¹² or —CONR¹¹R¹²;
Rˣ is hydrogen, halogen, (C₁-C₆)alkyl or —NHCO(C₁-C₆)alkyl;
R⁶ is hydrogen, halogen, (C₁-C₆)alkyl, (C₁-C₆)alkoxy, —CHF₂, —CFH₂, CF₃, (C₃-C₈)cycloalkyl, —NH₂ or NHSO₂(C₁-C₆)alkyl;
R⁷ is (C₁-C₆)alkyl, (C₁-C₆)alkoxy, (C₃-C₈)cycloalkyl, heterocyclylalkyl, amino(C₁-C₆)alkyl or hydroxy(C₁-C₆)alkyl;
R⁸ is hydrogen, (C₁-C₆)alkoxy or (C₁-C₆)alkyl;
R⁹ is hydrogen or a 5-8 membered heterocyclic ring containing 1-4 heteroatoms selected from —O—, —S— or —N—; or
R⁸ and R⁹ are taken together with the nitrogen to which they are attached to form a 5-8 membered heterocyclic ring containing 1-4 heteroatoms selected from —O—, —S— or —N—;
R¹⁰ is (C₁-C₆)alkyl;
R¹¹ is hydrogen, amino(C₁-C₆)alkyl or hydroxy(C₁-C₆)alkyl;
R¹² is hydrogen, amino(C₁-C₆)alkyl or hydroxy(C₁-C₆)alkyl;
n is 0 or 1;
or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

II. Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, triple-negative breast cancer, colorectal cancer, prostate cancer, melanoma, pancreatic cancer, multiple myeloma, T-acute lymphoblastic leukemia or AML.

In another embodiment, the invention provides a method for the treatment and/or prophylaxis of Marfan's syndrome and associated diseases, disorders and conditions associated with aberrant TGF-β expression.

In another embodiment, the invention provides a method for the treatment and/or prophylaxis of fibrosis such as hepatic or pulmonary fibrosis.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

III. Therapeutic Applications

The compounds of formula (I) of the invention are TGFβR antagonists and have potential utility in the treatment of diseases and conditions for which a TGFβR antagonist is indicated.

In one embodiment there is provided a method for the treatment of a disease or condition, for which a TGFβR antagonists is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

TGFβR antagonists are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

TGFβR antagonists may be useful in the treatment of fibrotic conditions such as idiopathic pulmonary fibrosis, renal fibrosis, post-operative stricture, keloid formation, scleroderma and cardiac fibrosis.

TGFβR antagonists may be useful in the treatment of cancer, including hematological, epithelial including lung, breast and colon carcinomas, midline carcinomas, mesenchymal, hepatic, renal and neurological tumours.

The term "diseases or conditions for which a TGFβR antagonists is indicated" is intended to include any of or all of the above disease states.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO009/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO009/1156652, WO11/56652, and WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C6 alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

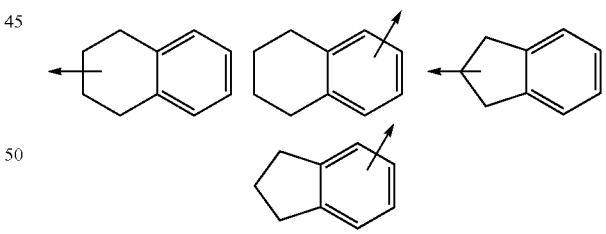

Arrowed lines drawn from the ring system indicate that the bond may be attached to any of the suitable ring atoms.

The term "benzyl," as used herein, refers to a methyl group on which one of the hydrogen atoms is replaced by a phenyl group.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl.

Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, CD3 denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

Compounds of general formula (i) can be prepared according to the method outlined in Scheme i. Protection of NH followed by selective displacement of the chlorine atom at the 4 position with alkoxide can afford ether iC. Palladium mediated coupling of mono chloro intermediate iC with various organometallic reagents can afford intermediate iD. The ether compound iD may be reacted with various amines followed by removal of the protecting group to yield compounds of general formula (i).

Scheme i

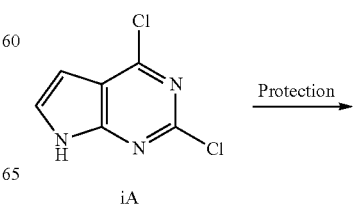

iA

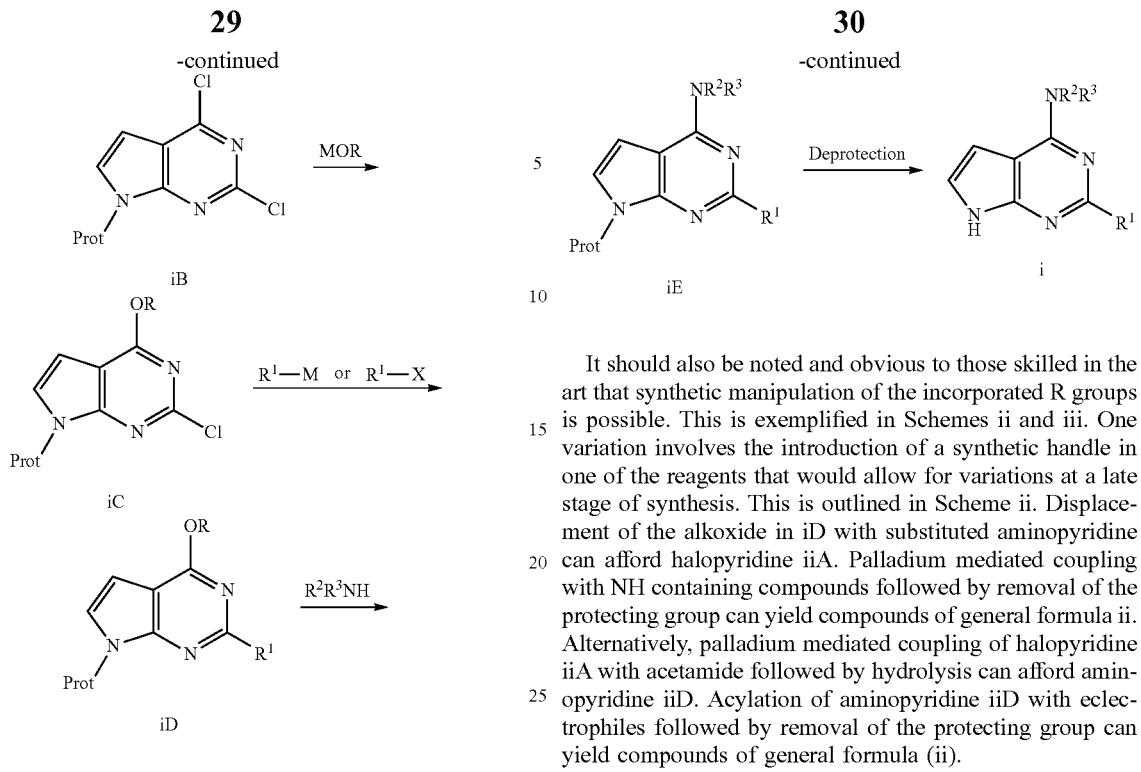

It should also be noted and obvious to those skilled in the art that synthetic manipulation of the incorporated R groups is possible. This is exemplified in Schemes ii and iii. One variation involves the introduction of a synthetic handle in one of the reagents that would allow for variations at a late stage of synthesis. This is outlined in Scheme ii. Displacement of the alkoxide in iD with substituted aminopyridine can afford halopyridine iiA. Palladium mediated coupling with NH containing compounds followed by removal of the protecting group can yield compounds of general formula ii. Alternatively, palladium mediated coupling of halopyridine iiA with acetamide followed by hydrolysis can afford aminopyridine iiD. Acylation of aminopyridine iiD with eclectrophiles followed by removal of the protecting group can yield compounds of general formula (ii).

Scheme ii

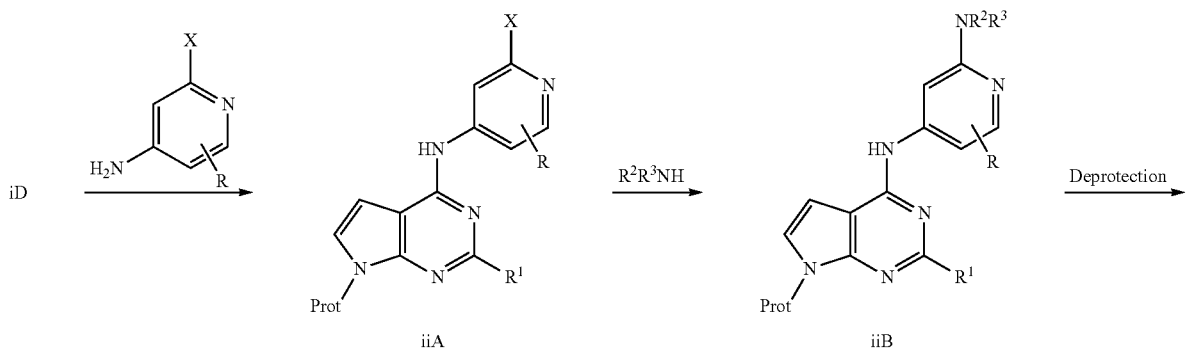

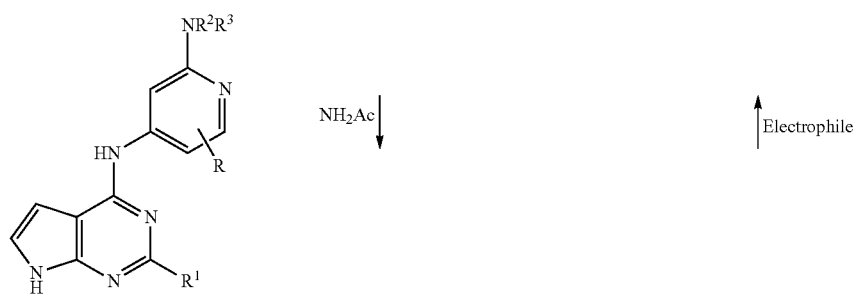

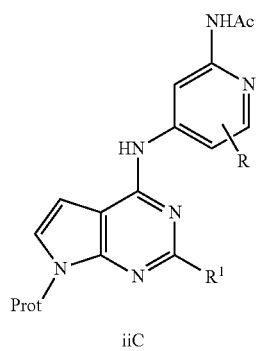

iiC

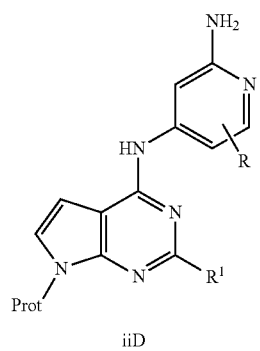

iiD

In another variation the primary amine iiD can be acylated with chloroacetylchloride to obtain halo amide iiiA (Scheme iii). Displacement of the chlorine atom of amide iiiA with amine nucleophiles can afford amine iiiB. Removal of the protecting group in amine iiiB can yield compounds of general formula iii.

Scheme iii iiD → [Cl-CH2-COCl] → iiiA

[R²R³NH] →

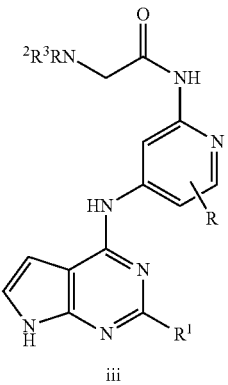

iii

Another variation involves the synthesis of differentially substituted pyrrolopyrimidine core as outlined in Schemes iv and v. This will allow for variations at the 5-position by using the iodine or aldehyde as a synthetic handle. Iodination of intermediate iD followed by palladium mediated coupling can afford ether ivB (Scheme iv). Substitution of alkoxide in ivB with amine nucleophiles followed by removal of the protecting group can form compounds of general formula iv.

Scheme iv

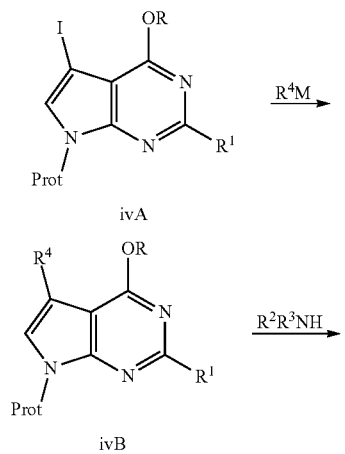

iiiB

Deprotection → iD → NIS → ivA → R⁴M → ivB → R²R³NH →

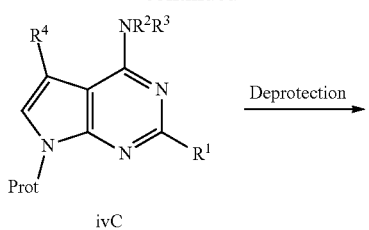

ivC

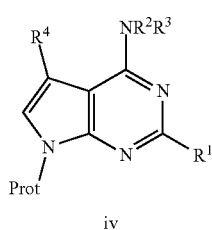

iv

Yet another variation is outlined in Scheme v. Formylation of intermediate iD can form aldehyde vA. Reductive amination of aldehyde vA with amine can yield ether vB. Nucleophilic aromatic substitution on ether vB followed by removal of the protecting group can afford compounds of general formula v.

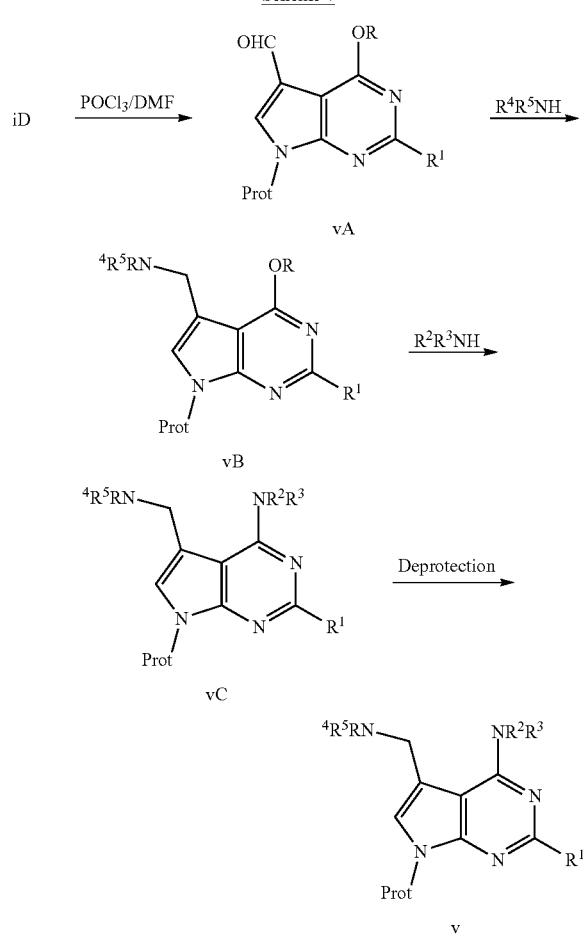

EXAMPLES

HPLC Conditions:

A: Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm.

B: Waters Acquity BEH C18 (2.1×50 mm) 1.7 micron; Buffer: 5 mM Ammonium Acetate pH 3.5, Solvent A: Buffer:ACN (95:5), Solvent B: Buffer:ACN (5:95), Method: % B: 0 min-5%:1.1 min-95%:1.7 min-95%, Flow: 0.8 mL/min.

C: Ascentis Express C18 (2.1×50 mm), 2.7 micron; Solvent A: 5:95 acetonitrile:water with 10 mM $NH_4OAc$; Solvent B: 95:5 acetonitrile:water with 10 mM $NH_4OAc$; Temperature: 50° C.; Gradient: 0-100% B over 3 minutes; Flow rate: 1.1 mL/min; Detection: UV at 220 nm.

D: Column: Ascentis Express C18 (50×2.1 mm), 2.7 micron; Solvent A: 5:95 Acetonitrile:water with 0.1% TFA; Solvent B: 95:5 Acetonitrile:water with 0.1% TFA; Temperature: 50° C.; Gradient: 0-100% B over 3 minutes; Flow: 1.1 mL/min.

E: Kinetex XB-C18 (75×3 mm) 2.6 micron; Solvent A: 10 mM ammonium formate in water:acetonitrile (98:02); Mobile Phase B: 10 mM ammonium formate in water:acetonitrile (02:98); Temperature: 50° C.; Gradient: 0-100% B over 3 minutes; Flow rate: 1.1 mL/min; Detection: UV at 220 nm.

F: Kinetix C18 (75×3 mm) 2.6 micron; Solvent A: 0.1% Formic acid in water; Solvent B: 0.1% Formic acid in acetonitrile; Gradient: 0-100% B over 4 min; Flow rate: 1.0 mL/min; Detection: UV at 254 nm.

G: Waters Acquity UPLC BEH C18 (2.1×50 mm), 1.7 micron; Solvent A: 5:95 acetonitrile:water with 10 mM ammonium acetate; Solvent B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

H. Waters Acquity UPLC BEH C18 (2.1×50 mm), 1.7 micron; Solvent A: 5:95 acetonitrile:water with 0.1% trifluoroacetic acid; Solvent B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Scheme 1

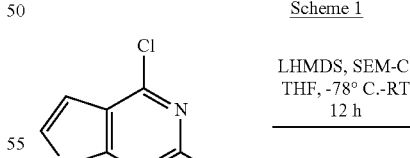

1A

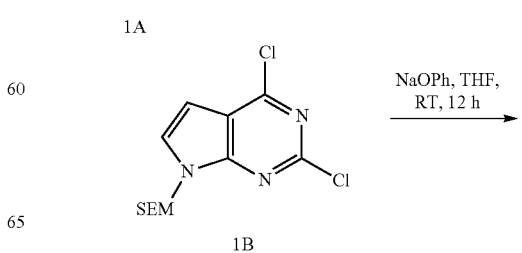

1B

-continued

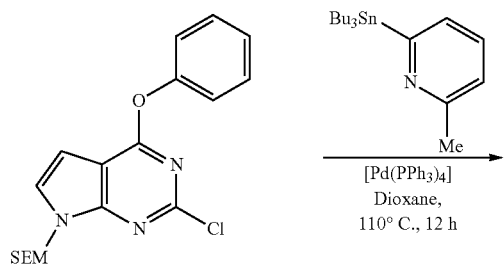

1C

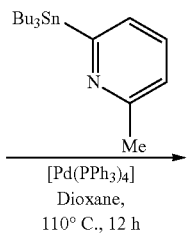
[Pd(PPh₃)₄]
Dioxane,
110° C., 12 h

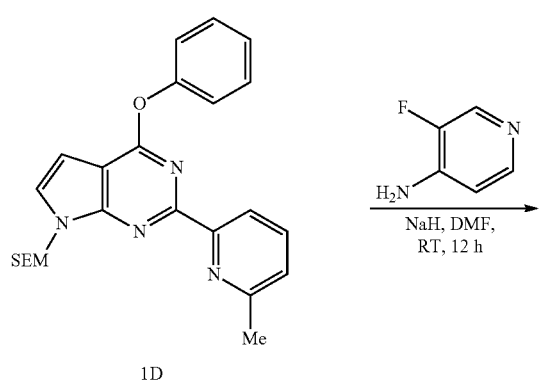

1D

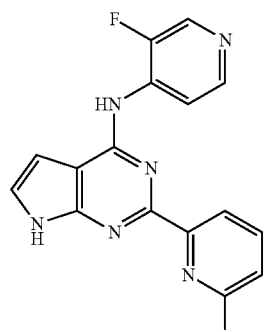
NaH, DMF,
RT, 12 h

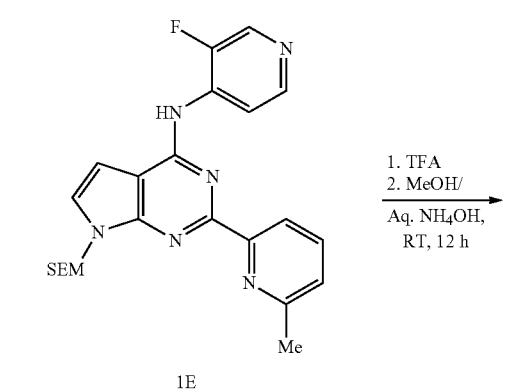

1E

1. TFA
2. MeOH/
Aq. NH₄OH,
RT, 12 h

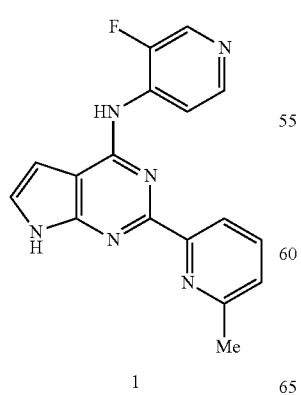

1

Example 1

N-(3-fluoropyridin-4-yl)-2-(6-methylpyridin-2-yl)-7H-pyrrolo[2,3-d]pyrimidin-4-amine Intermediate 1B: 2,4-dichloro-7-((2-(trimethylsilyl)ethoxy)methyl)-7H-pyrrolo[2,3-d]pyrimidine

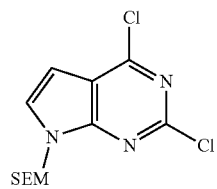 [SMILES: C[Si](C)(C)CCOCn1ccc2c(Cl)nc(Cl)nc21]

To a stirred solution of 2,4-dichloro-7H-pyrrolo[2,3-d]pyrimidine (5.00 g, 26.6 mmol) in THF (100 mL) at −78° C. was added a 1.0 M solution of LHMDS (26.6 mL, 26.6 mmol) in THF. The reaction mixture was stirred for 45 min and then a solution of SEM-Cl (4.72 mL, 26.6 mmol) in THF (10 mL) was added. The reaction mixture was warmed up to room temperature and stirred for 12 h. The reaction was judged complete by LCMS. The reaction mixture was diluted with ethyl acetate (500 mL) and washed with water (100 mL). The organic phase was dried over anhydrous sodium sulfate and concentrated. The resulting residue was purified by silica gel chromatography (using 20-30% ethyl acetate in petroleum ether) to get 2,4-dichloro-7-((2-(trimethylsilyl)ethoxy)methyl)-7H-pyrrolo[2,3-d]pyrimidine (7 g, 19.79 mmol, 74.4% yield) as colorless liquid. LCMS m/z 318.2 (M+H); rt 3.71 min; conditions E.

Intermediate 1C: 2-chloro-4-phenoxy-7-((2-(trimethylsilyl)ethoxy)methyl)-7H-pyrrolo[2,3-d]pyrimidine To a mixture of 2,4-dichloro-7-((2-(trimethylsilyl)ethoxy)methyl)-7H-pyrrolo[2,3-d]pyrimidine (3.0 g, 9.43 mmol) and sodium phenolate (1.423 g, 12.25 mmol) was added THF (30 mL) and stirred at room temperature for 12 h. The reaction mixture was concentrated. The residue was dissolved in ethyl acetate and washed with water. The organic phase was dried over anhydrous sodium sulfate and concentrated. The resulting residue was purified by silica gel chromatography (using 20-30% ethyl acetate/petroleum ether) to get 2-chloro-4-phenoxy-7-((2-(trimethylsilyl)ethoxy)methyl)-7H-pyrrolo[2,3-d]pyrimidine (3.2 g, 7.66 mmol, 81% yield) as colorless liquid. LCMS m/z 376.2 (M+H); rt 3.91 min; conditions F.

Intermediate-4; 2-(6-methylpyridin-2-yl)-4-phenoxy-7-((2-(trimethylsilyl)ethoxy) methyl)-7H-pyrrolo[2,3-d]pyrimidine

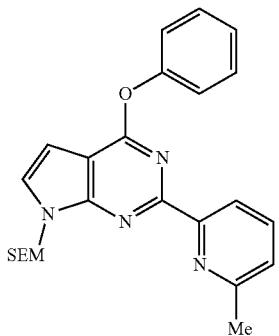 [SMILES: Cc1cccc(-c2nc(Oc3ccccc3)c3ccn(COCC[Si](C)(C)C)c3n2)n1]

To a degassed solution of 2-chloro-4-phenoxy-7-((2-(trimethylsilyl) ethoxy)methyl)-7H-pyrrolo[2,3-d]pyrimidine (0.5 g, 1.330 mmol) and 2-methyl-6-(tributylstannyl)pyridine (0.559 g, 1.463 mmol) in 1,4-dioxane (20 mL) was added tetrakis(triphenylphosphine)palladium(0) (0.154 g, 0.133 mmol). The reaction mixture was heated to 110° C. in sealed tube for 12 h. The reaction mixture was cooled to room temperature, filtered through a pad of celite and concentrated. The resulting residue was purified by silica gel chromatography (using 25-40% ethyl acetate in petroleum ether) to obtain 2-(6-methylpyridin-2-yl)-4-phenoxy-7-((2-(trimethylsilyl)ethoxy)methyl)-7H-pyrrolo[2,3-d]pyrimidine (0.492 g, 1.069 mmol, 80% yield) as colorless liquid. LCMS m/z 333.2 (M+H); rt 3.89 min; conditions E.

Intermediate 1E: N-(3-fluoropyridin-4-yl)-2-(6-methylpyridin-2-yl)-7-((2-(trimethylsilyl)ethoxy)methyl)-7H-pyrrolo[2,3-d]pyrimidin-4-amine

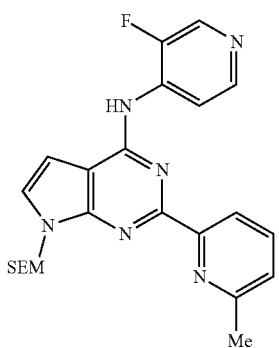 [SMILES: Cc1cccc(-c2nc(Nc3ccncc3F)c3ccn(COCC[Si](C)(C)C)c3n2)n1]

To a solution of 3-fluoropyridin-4-amine (0.45 g, 4.01 mmol) and 2-(6-methylpyridin-2-yl)-4-phenoxy-7-((2-(trimethylsilyl)ethoxy)methyl)-7H-pyrrolo[2,3-d]pyrimidine (0.45 g, 1.040 mmol) in DMF (10 mL) at 0° C. was added sodium hydride (0.325 g, 13.52 mmol). The reaction mixture was stirred at room temperature for 12 h. The reaction was monitored by LCMS until completion. The reaction mixture was poured into ice-cold water and stirred for 30 min. The precipitate formed was filtered and dried to get N-(3-fluoropyridin-4-yl)-2-(6-methylpyridin-2-yl)-7-((2-(trimethylsilyl) ethoxy)methyl)-7H-pyrrolo[2,3-d]pyrimidin-4-amine (320 mg, 0.696 mmol, 66.9% yield) as light gray solid. LCMS m/z 451.2 (M+H); rt 3.24 min; conditions E.

To N-(3-fluoropyridin-4-yl)-2-(6-methylpyridin-2-yl)-7-((2-(trimethylsilyl)ethoxy)methyl)-7H-pyrrolo[2,3-d]pyrimidin-4-amine (55 mg, 0.122 mmol) was added TFA (2 mL, 26.0 mmol) and stirred at room temperature for 12 h. The reaction mixture was analyzed by LCMS to observe the N—CH$_2$OH intermediate (m/z 351). The reaction mixture was concentrated. To the resulting residue was added methanol (1.5 mL), 33% aqueous ammonium hydroxide (1.5 mL) and stirred for 1 h at room temperature until the reaction was judged complete by LCMS. The reaction mixture was concentrated, and the residue was purified by reverse phase HPLC to obtain Example 1 (26.3 mg, 0.081 mmol, 66.6% yield) as an off white solid. LCMS m/z 321.2, (M+H); rt 2.26 min; conditions E; $^1$H NMR (400 MHz, DMSO-d$_6$) δ 12.13 (br. s., 1H), 9.63-9.55 (m, 1H), 8.80 (s, 1H), 8.58-8.52 (m, 1H), 8.43-8.32 (m, 1H), 8.14 (s, 1H), 7.81 (t, J=7.8 Hz, 1H), 7.47-7.39 (m, 1H), 7.32 (s, 1H), 7.02-6.95 (m, 1H), 2.59 (s, 3H).

Scheme 2

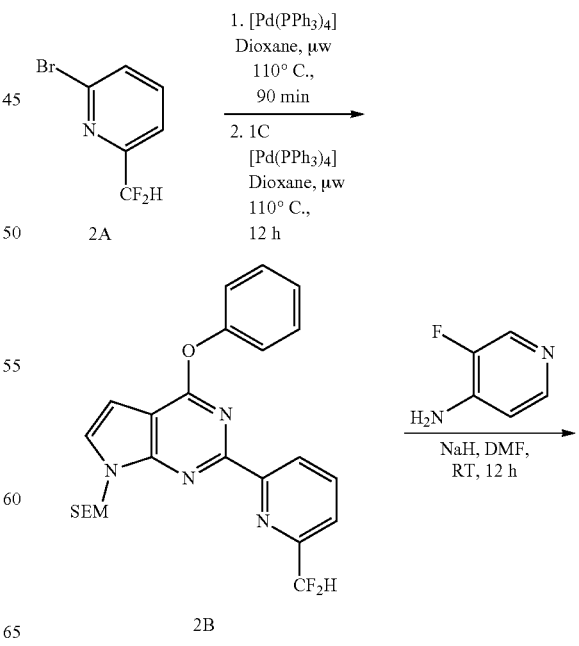

-continued

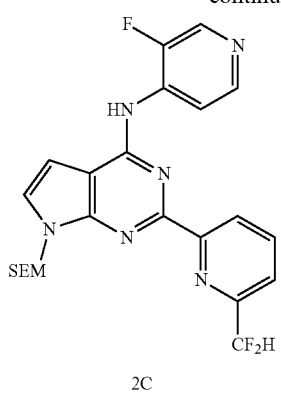

2C

1. TFA
2. MeOH/
Aq. NH₄OH,
RT, 12 h
→

Intermediate 2B: 2-(6-(difluoromethyl)pyridin-2-yl)-4-phenoxy-7-((2-(trimethylsilyl) ethoxy)methyl)-7H-pyrrolo[2,3-d]pyrimidine

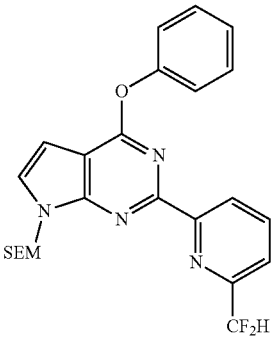

To 2-bromo-6-(difluoromethyl)pyridine (0.6 g, 2.88 mmol) and hexamethylditin (0.718 mL, 3.46 mmol) was added 1,4-dioxane (15 mL). The reaction mixture was degassed and then added tetrakis(triphenylphosphine)palladium(0) (0.333 g, 0.288 mmol). The mixture was stirred at 110° C. under microwave irradiation for 90 min. LCMS indicated completion of reaction. The reaction mixture was cooled to room temperature, filtered through a pad of celite and concentrated. To the resulting crude stannyl intermediate was added 2-chloro-4-phenoxy-7-((2-(trimethylsilyl) ethoxy)methyl)-7H-pyrrolo[2,3-d]pyrimidine (1.084 g, 2.88 mmol) and 1,4-dioxane (15 mL). To the resulting reaction mixture was added tetrakis(triphenylphosphine)palladium (0) (0.333 g, 0.288 mmol)) and heated to 110° C. in 100 mL sealed tube for 12 h. The mixture was cooled to room temperature and filtered through a pad of celite. The filtrate was concentrated. The resulting crude compound was purified by silica gel chromatography (10-15% ethyl acetate in petroleum ether) to get 2-(6-(difluoromethyl)pyridin-2-yl)-4-phenoxy-7-((2-(trimethylsilyl)ethoxy)methyl)-7H-pyrrolo[2,3-d]pyrimidine (0.6 g, 1.024 mmol, 35.5% yield) as a pale yellow liquid. LCMS m/z 469.2 (M+H); rt 3.03 min; conditions E.

Intermediate 2C: 2-(6-(difluoromethyl)pyridin-2-yl)-N-(3-fluoropyridin-4-yl)-7-((2-(trimethylsilyl)ethoxy)methyl)-7H-pyrrolo[2,3-d]pyrimidin-4-amine

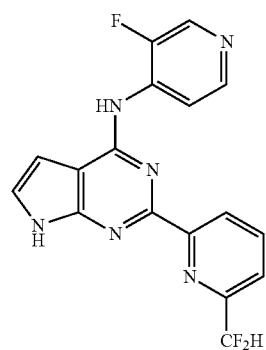 [SMILES: Fc1cnccc1Nc1nc(-c2cccc(C(F)F)n2)nc2[nH]ccc12]

2

Example 2

2-(6-(difluoromethyl)pyridin-2-yl)-N-(3-fluoropyridin-4-yl)-7H-pyrrolo[2,3-d]pyrimidin-4-amine

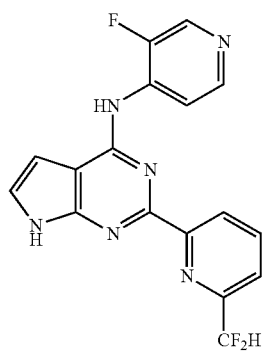

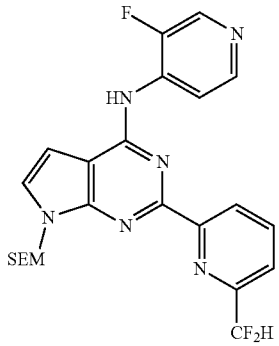 [SMILES: C[Si](C)(C)CCOCn1ccc2c(Nc3ccncc3F)nc(-c3cccc(C(F)F)n3)nc21]

Intermediate 2C was prepared in a similar fashion to intermediate 1E (Scheme 1) to obtain (130 mg, 0.102 mmol, 23.79%) as a light brown solid. LCMS m/z 487.2 (M+H); rt 4.186 min; conditions E.

Example 2 (54 mg, 0.145 mmol, 54.5%) was synthesized employing the procedure described for Example 1 (Scheme 1) LCMS m/z 357.2 (M+H); rt 1.61 min; conditions C; $^1$H NMR (400 MHz, DMSO-$d_6$) δ 12.51 (br. s., 1H), 9.96 (s, 1H), 9.09-8.98 (m, 1H), 8.83 (d, J=3.4 Hz, 1H), 8.73 (s, 1H), 8.66 (d, J=5.4 Hz, 1H), 8.50-8.30 (m, 1H), 8.04 (s, 1H), 7.82-7.66 (m, 1H), 7.53-7.10 (m, 2H).

Scheme 3

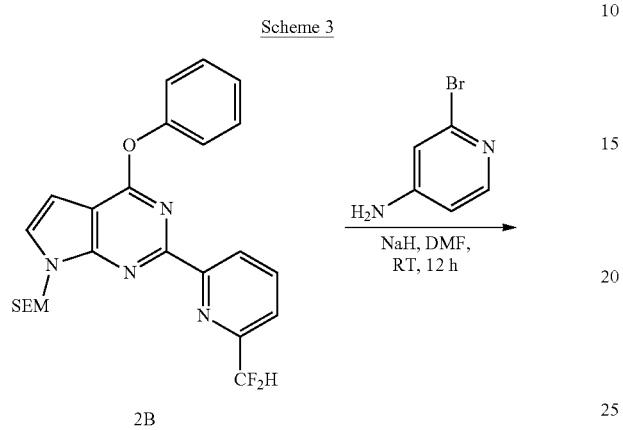
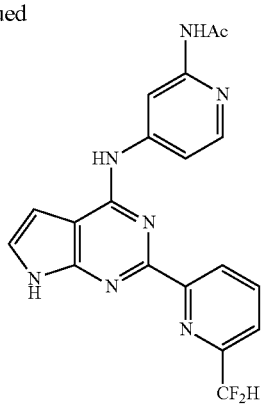

2B

Example 3

N-(4-((2-(6-(difluoromethyl)pyridin-2-yl)-7H-pyrrolo[2,3-d]pyrimidin-4-yl)amino)pyridin-2-yl)acetamide

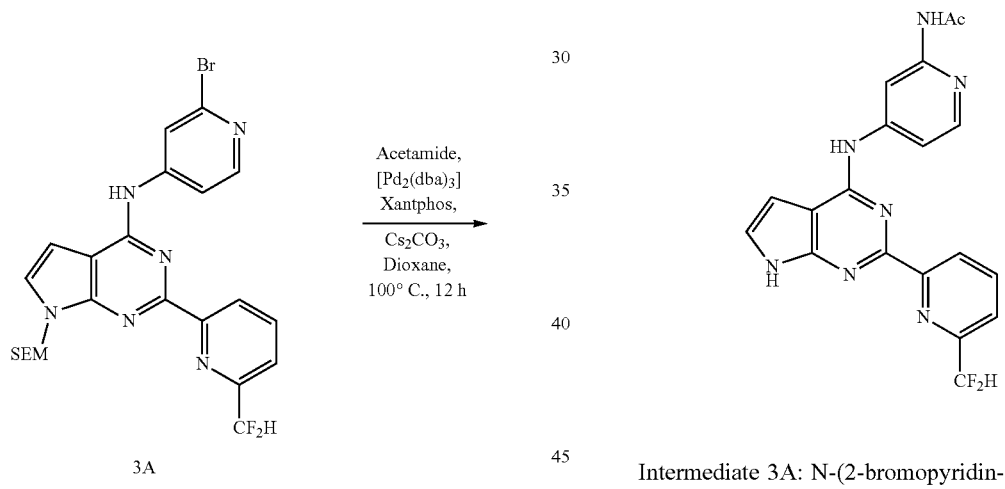

Intermediate 3A: N-(2-bromopyridin-4-yl)-2-(6-(difluoromethyl)pyridin-2-yl)-7-((2-(trimethylsilyl)ethoxy)methyl)-7H-pyrrolo[2,3-d]pyrimidin-4-amine

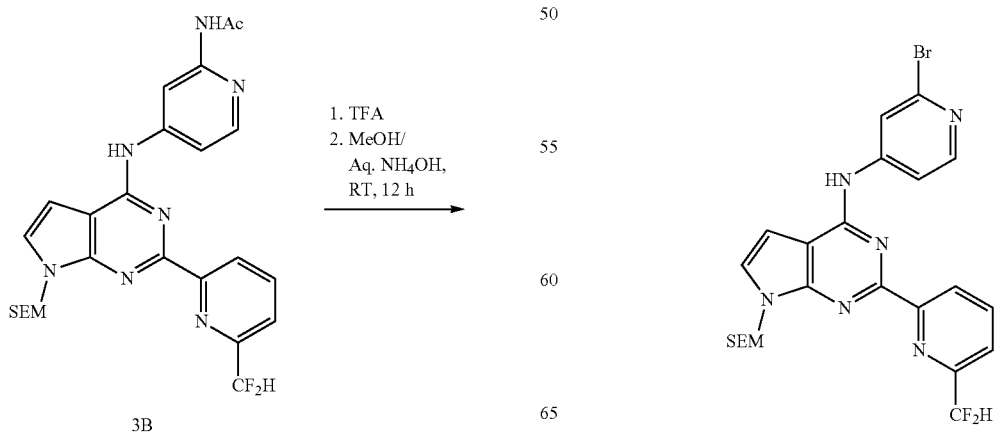

Intermediate 3A (0.25 g, 0.269 mmol, 50.5%) was synthesized employing the procedure described for intermediate 1E (Scheme 1). LCMS m/z 549.2 (M+2); rt 3.90 min; conditions E.

Intermediate 3B: N-(4-((2-(6-(difluoromethyl)pyridin-2-yl)-7-((2-(trimethylsilyl)ethoxy)methyl)-7H-pyrrolo[2,3-d]pyrimidin-4-yl)amino)pyridin-2-yl)acetamide

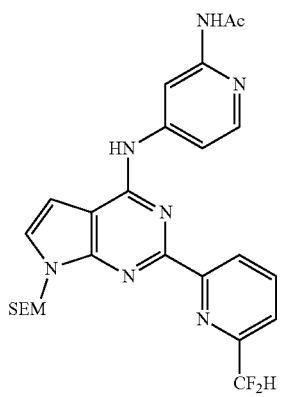 [SMILES: CC(=O)Nc1cc(Nc2nc(-c3cccc(C(F)F)n3)nc3c2ccn3COCC[Si](C)(C)C)ccn1]

To a stirred suspension of N-(2-bromopyridin-4-yl)-2-(6-(difluoromethyl)pyridin-2-yl)-7-((2-(trimethylsilyl)ethoxy)methyl)-7H-pyrrolo[2,3-d]pyrimidin-4-amine (0.25 g, 0.457 mmol), acetamide (0.040 g, 0.685 mmol), 4,5-bis(diphenylphosphino)-9,9-dimethylxanthene (0.053 g, 0.091 mmol) and cesium carbonate (0.298 g, 0.913 mmol) in dioxane (10 mL) was added tris(dibenzylidineacetone)dipalladium(0) (0.042 g, 0.046 mmol). The reaction mixture was heated at 100° C. for 12 h. The reaction was monitored by LCMS. The reaction mixture was cooled to room temperature and filtered through a pad of celite. The filtrate was concentrated to get N-(4-((2-(6-(difluoromethyl)pyridin-2-yl)-7-((2-(trimethylsilyl)ethoxy)methyl)-7H-pyrrolo[2,3-d]pyrimidin-4-yl)amino)pyridin-2-yl)acetamide (0.2 g, 0.297 mmol, 65.0% yield) as a semi solid. LCMS m/z 526.2 (M+1); rt 3.82 min; conditions E.

Example 3 (13 mg, 0.033 mmol, 8.56%) was obtained employing the procedure described for Example 1 (Scheme 1). LCMS m/z 396.1 (M+H); rt 1.45 min; conditions C; $^1$H NMR (400 MHz, DMSO-$d_6$) δ 12.47 (br. s., 1H), 10.67-10.51 (m, 1H), 10.28-10.08 (m, 1H), 9.00 (d, J=7.8 Hz, 2H), 8.58-8.32 (m, 3H), 8.13-7.93 (m, 1H), 7.72 (s, 1H), 7.53-7.07 (m, 2H), 2.40 (s, 3H).

Scheme 4

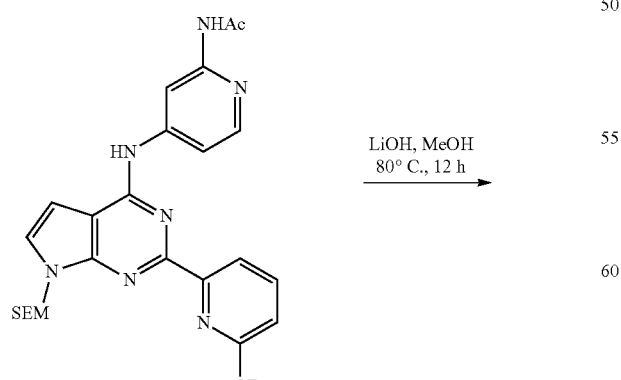

4A

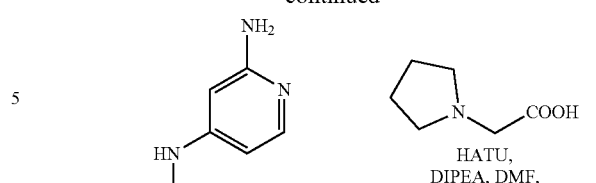

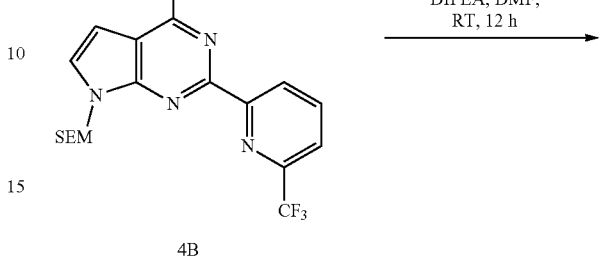

4B

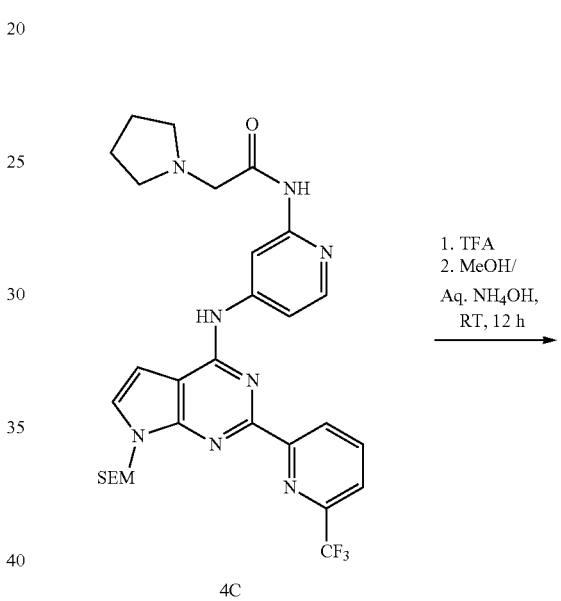

4C

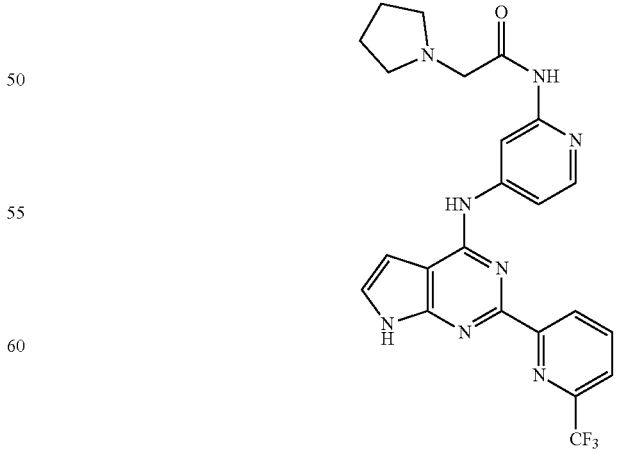

4

Example 4

2-(pyrrolidin-1-yl)-N-(4-((2-(6-(trifluoromethyl) pyridin-2-yl)-7H-pyrrolo[2,3-d]pyrimidin-4-yl) amino)pyridin-2-yl)acetamide

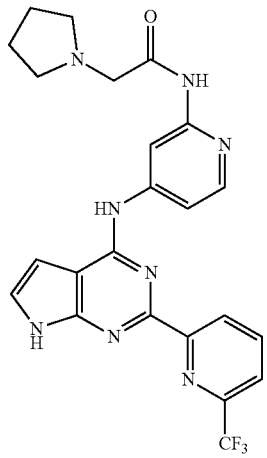 [SMILES: O=C(CN1CCCC1)Nc1cc(Nc2nc(-c3cccc(C(F)(F)F)n3)nc3[nH]ccc23)ccn1]

Intermediate 4A: N-(4-((2-(6-(trifluoromethyl)pyridin-2-yl)-7-((2-(trimethylsilyl) ethoxy)methyl)-7H-pyrrolo[2,3-d]pyrimidin-4-yl)amino)pyridin-2-yl) acetamide

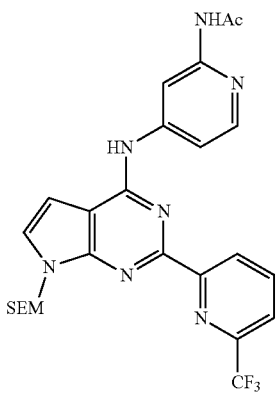 [SMILES: CC(=O)Nc1cc(Nc2nc(-c3cccc(C(F)(F)F)n3)nc3c2ccn3COCC[Si](C)(C)C)ccn1]

Intermediate 4A was synthesized employing the procedure described for intermediate 3B. LCMS m/z 544.2 (M+1); rt 3.46 min; conditions E.

Intermediate 4B: $N^4$-(2-(6-(trifluoromethyl))pyridin-2-yl)-7-((2-(trimethylsilyl)ethoxy)methyl)-7H-pyrrolo[2,3-d]pyrimidin-4-yl)pyridine-2,4-diamine

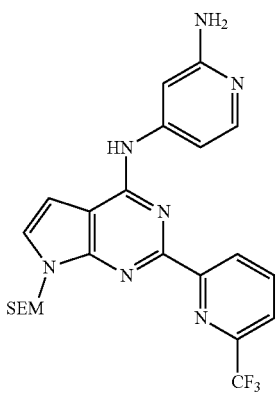 [SMILES: C[Si](C)(C)CCOCn1ccc2c(Nc3ccnc(N)c3)nc(-c3cccc(C(F)(F)F)n3)nc21]

To a stirred solution of N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide (0.15 g, 0.276 mmol) in methanol (5 mL) was added 2.0 M aqueous lithium hydroxide (2 mL, 4.00 mmol) and mixture was heated at 80° C. for 12 h. The reaction mixture was cooled to room temperature and analyzed LCMS to verify complete conversion. The reaction mixture was concentrated. To the resulting residue was added water, stirred and decanted. The resulting gum was triturated with petroleum ether. The resulting suspension was filtered to get $N^4$-(2-(6-(trifluoromethyl)pyridin-2-yl)-7-((2-(trimethylsilyl)ethoxy)methyl)-7H-pyrrolo[2,3-d]pyrimidin-4-yl)pyridine-2,4-diamine (110 mg, 0.219 mmol, 79% yield) as a pale orange solid. LCMS m/z 502.2 (M+H); rt 3.54 min: conditions E.

Intermediate 4C: 2-(pyrrolidin-1-yl)-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide

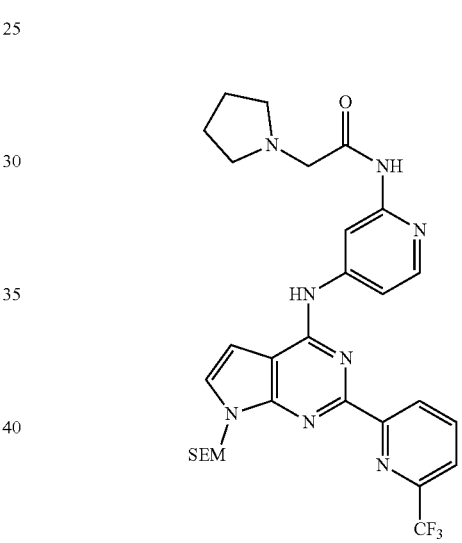

$N^4$-(2-(6-(trifluoromethyl)pyridin-2-yl)-7-((2-(trimethylsilyl)ethoxy)methyl)-7H-pyrrolo[2,3-d]pyrimidin-4-yl)pyridine-2,4-diamine (100 mg, 0.199 mmol) was added to a stirred solution of 2-(pyrrolidin-1-yl)acetic acid (64.4 mg, 0.498 mmol), HATU (265 mg, 0.698 mmol) and DIPEA (0.104 mL, 0.598 mmol) in DMF (2 mL). The reaction mixture was stirred at room temperature for 12 h. The reaction mixture was concentrated under reduced pressure and the residue was partitioned between DCM and water. The aqueous layer was extracted with DCM. The combined organic layer was dried over sodium sulfate and concentrated to get 22-(pyrrolidin-1-yl)-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl) acetamide (90 mg, 0.110 mmol, 55.3% yield) as a gum, which was used in the next step without purification. LCMS m/z 613.2 (M+H); rt 4.26 min; conditions E.

Example 4 (31 mg, 0.064 mmol, 43.7%) was synthesized from intermediate 4C, employing the procedure described for Example 1 (Scheme 1). LCMS m/z 483.2 (M+H); rt 1.84 min; conditions D; $^1$H NMR (400 MHz, DMSO-$d_6$) δ 12.30 (br. s., 1H), 10.03 (s, 1H), 9.80 (br. s., 1H), 8.90 (d, J=8.0 Hz, 1H), 8.74 (d, J=1.5 Hz, 1H), 8.29-8.08 (m, 3H), 8.01-7.89 (m, 1H), 7.48 (dd, J=3.5, 2.5 Hz, 1H), 7.01 (dd, J=3.5, 2.0 Hz, 1H), 3.46-3.36 (m, 2H), 2.75-2.64 (m, 4H), 1.86-1.74 (m, 4H).
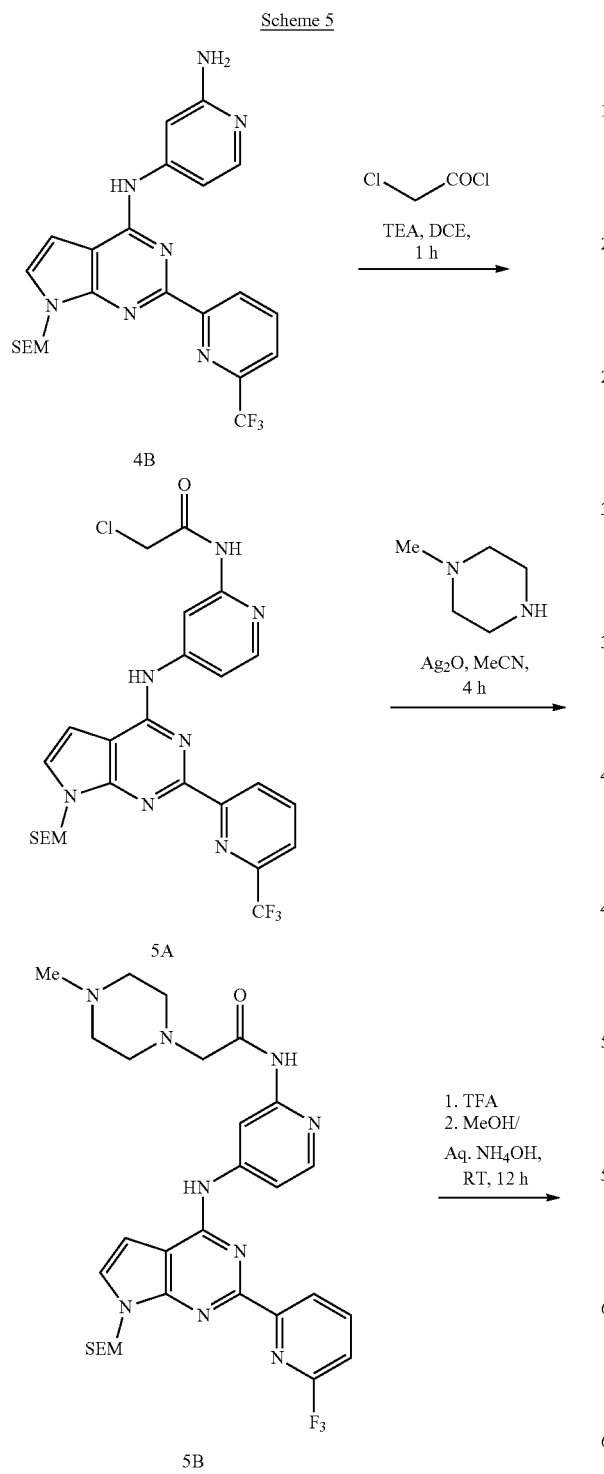
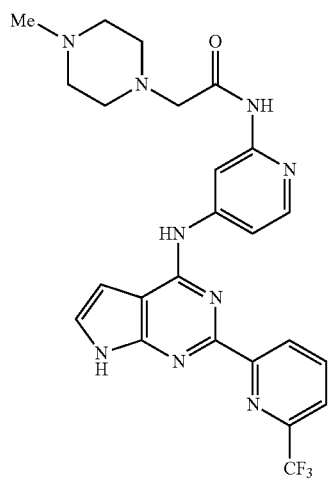 [SMILES: CN1CCN(CC(=O)Nc2cc(Nc3nc(-c4cccc(C(F)(F)F)n4)nc4[nH]ccc34)ccn2)CC1]
5
Example 5
2-(4-methylpiperazin-1-yl)-N-(4-((2-(6-(trifluoromethyl)pyridin-2-yl)-7H-pyrrolo[2,3-d]pyrimidin-4-yl)amino)pyridin-2-yl)acetamide
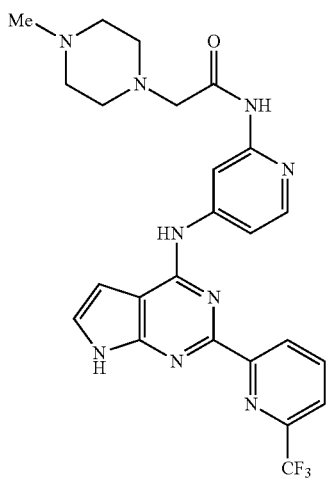

Intermediate 5A: 2-chloro-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide

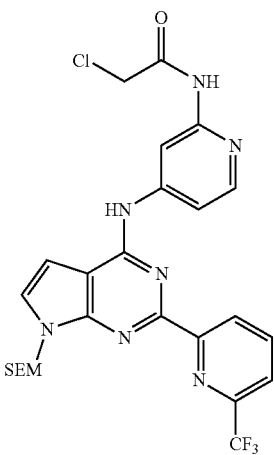 [SMILES: C[Si](C)(C)CCOCn1ccc2c(Nc3ccnc(NC(=O)CCl)c3)nc(-c3cccc(C(F)(F)F)n3)nc21]

To a stirred solution of N⁴-(2-(6-(trifluoromethyl)pyridin-2-yl)-7-((2-(trimethylsilyl)ethoxy)methyl)-7H-pyrrolo[2,3-d]pyrimidin-4-yl)pyridine-2,4-diamine (0.11 g, 0.219 mmol) and triethylamine (0.153 mL, 1.097 mmol) in 1,2-dichloroethane (8 mL) at 0° C., was added chloroacetyl chloride (0.079 mL, 0.987 mmol). The reaction mixture was stirred at room temperature for 1 h. The reaction was monitored by LCMS. The reaction mixture was diluted with DCM (10 mL) and washed with water. The organic phase was dried over anhydrous sodium sulfate and concentrated to get 2-chloro-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide (0.13 g, 0.164 mmol, 74.9% yield) as black semi solid. LCMS m/z 578.2 (M+H); rt 3.85 min; conditions E.

Intermediate 5B: 2-(4-methylpiperazin-1-yl)-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide

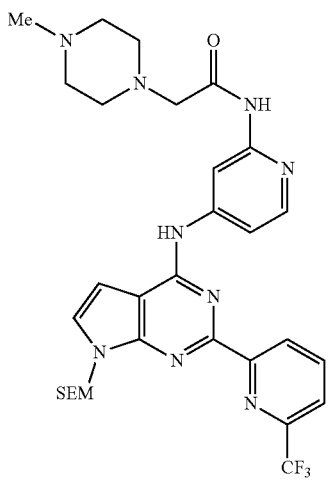 [SMILES: CN1CCN(CC(=O)Nc2cc(Nc3nc(-c4cccc(C(F)(F)F)n4)nc4c3ccn4COCC[Si](C)(C)C)ccn2)CC1]

To a solution of 2-chloro-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide (0.13 g, 0.225 mmol) in acetonitrile (8 mL) were added 1-methylpiperazine (0.150 mL, 1.349 mmol) and silver oxide (0.104 g, 0.450 mmol). The reaction mixture was stirred at room temperature for 4 h. The reaction was monitored by LCMS. The reaction mixture was diluted with ethyl acetate and filtered through a apd of celite. The filtrate was concentrated and purified by silica gel chromatography (2-3% MeOH in DCM) to get 2-(4-methylpiperazin-1-yl)-N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide (77 mg, 0.029 mmol, 12.80% yield) as a gum. LCMS m/z 642.2 (M+H); rt 4.29 min; conditions E.

Example 5 (14.1 mg, 0.027 mmol, 22.75%) was obtained from intermediate 5B, employing the procedure described for the conversion of intermediate 1E to Example 1. LCMS m/z 512.2 (M+H); rt 1.34 min; conditions C; ¹H NMR (400 MHz, DMSO-d₆) δ 12.30 (br. s., 1H), 10.03 (s, 1H), 9.92 (br. s., 1H), 8.90 (d, J=8.1 Hz, 1H), 8.77 (s, 1H), 8.23 (s, 3H), 7.99 (s, 1H), 7.49 (dd, J=3.4, 2.4 Hz, 1H), 7.01 (dd, J=3.4, 2.0 Hz, 2H), 3.18 (d, J=5.1 Hz, 1H), 2.96 (br. s., 4H), 2.73 (br. s., 4H), 2.68-2.61 (m, 3H).

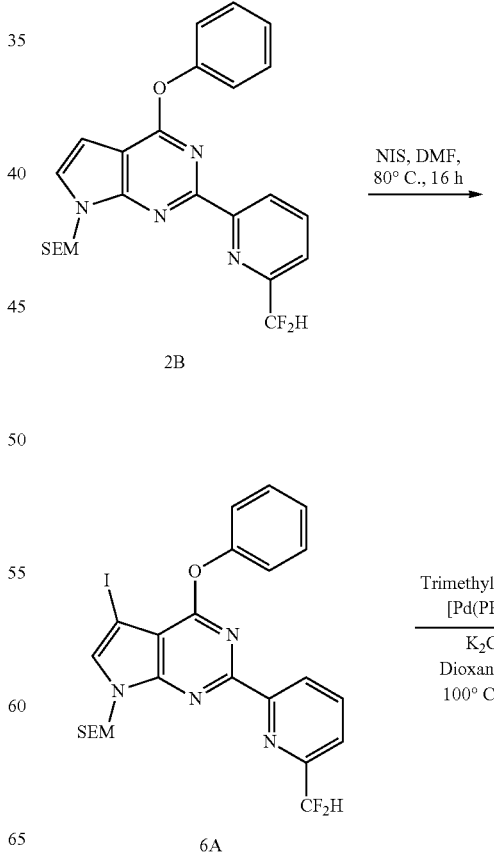

-continued

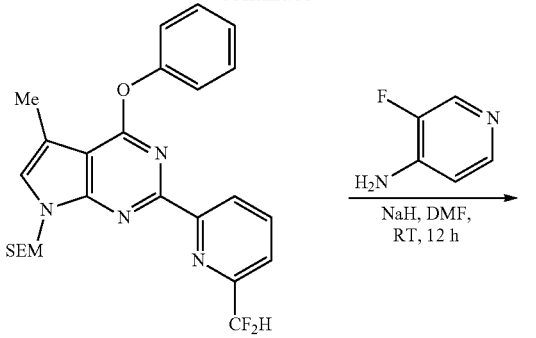

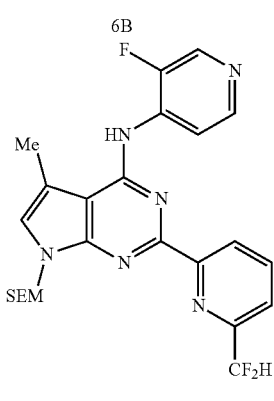

6C

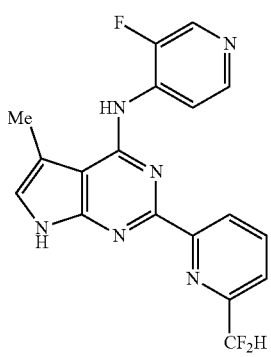 [SMILES: Cc1c[nH]c2nc(-c3cccc(C(F)F)n3)nc(Nc3ccncc3F)c12]

6

Example 6

2-(6-(difluoromethyl)pyridin-2-yl)-N-(3-fluoropyridin-4-yl)-5-methyl-7H-pyrrolo[2,3-d]pyrimidin-4-amine

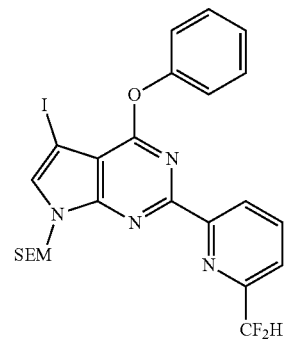 [SMILES: C[Si](C)(C)CCOCn1cc(I)c2c(Oc3ccccc3)nc(-c3cccc(C(F)F)n3)nc21]

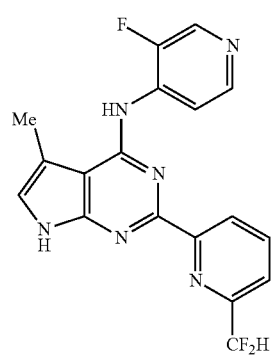

Intermediate 6A: 2-(6-(difluoromethyl)pyridin-2-yl)-5-iodo-4-phenoxy-7-((2-(trimethylsilyl)ethoxy)methyl)-7H-pyrrolo[2,3-d]pyrimidine To a 50 mL flask was added 2-(6-(difluoromethyl) pyridin-2-yl)-4-phenoxy-7-((2-(trimethylsilyl) ethoxy) methyl)-7H-pyrrolo[2, 3-d]pyrimidine (0.6 g, 1.280 mmol), N-iodosuccinimide (0.432 g, 1.921 mmol) and DMF (5 mL). The reaction mixture was stirred at 80° C. for 16 h. Upon completion of the reaction as judged by TLC, the reaction mixture was quenched with 20% aqueous $Na_2S_2O_3$. The resulting mixture was extracted with ethyl acetate (3×15 mL). The combined the organic layer was washed with aqueous $NaHCO_3$ (2×15 mL) and brine. The organic layer was dried over sodium sulfate and concentrated. The residue was purified via silica gel chromatography (10:1 Hex/EtOAc) to afford 2-(6-(difluoromethyl)pyridin-2-yl)-5-iodo-4-phenoxy-7-((2-trimethylsilyl)ethoxy)methyl)-7H-pyrrolo[2,3-d]pyrimidine (0.5 g, 0.841 mmol, 65%) as a yellow solid. LCMS m/z 595 (M+H); rt 4.41 min; conditions E.

Intermediate 6B: 2-(6-(difluoromethyl)pyridin-2-yl)-5-methyl-4-phenoxy-7-((2-(trimethylsilyl)ethoxy)methyl)-7H-pyrrolo[2,3-d]pyrimidine

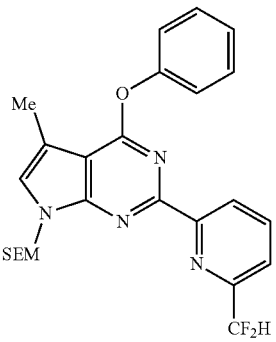 [SMILES: Cc1cn(COCC[Si](C)(C)C)c2nc(-c3cccc(C(F)F)n3)nc(Oc3ccccc3)c12]

To a 30 mL pressure tube was added 2-(6-(difluoromethyl)pyridin-2-yl)-5-iodo-4-phenoxy-7-((2-(trimethylsilyl)ethoxy)methyl)-7H-pyrrolo[2,3-d]pyrimidine (0.3 g, 0.505 mmol), trimethylboroxine (0.422 ml, 3.03 mmol), potassium carbonate (0.209 g, 1.514 mmol), 1,4-dioxane (5 mL) and water (1 mL). The resulting mixture was degassed with nitrogen, and then added tetrakis(triphenylphosphine)palladium (0) (0.029 g, 0.025 mmol). The reaction mixture was stirred at 100° C. for 16 h. Upon completion of reaction as judged by LCMS, the reaction mixture was diluted with water and extracted with ethyl acetate (3×10 mL). The combined organic layer was washed with 10% aqueous $NaHCO_3$ (2×10 mL) and brine. The organic layer was dried over sodium sulfate and concentrated. The residue was purified via silica gel chromatography on (5:1 Hexanes/EtOAc) to afford 2-(6-(difluoromethyl)pyridin-2-yl)-5-methyl-4-phenoxy-7-((2-(trimethylsilyl)ethoxy)methyl)-7H-pyrrolo[2,3-d]pyrimidine (0.15 g, 0.311 mmol, 61%) as a pale yellow gum. LCMS m/z 483.2 (M+H); rt 4.32; conditions E.

Intermediate 6C

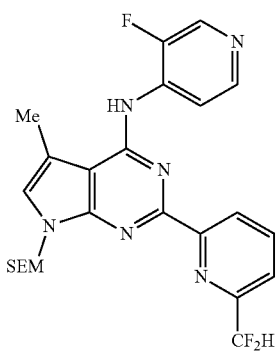 [SMILES: Cc1cn(COCC[Si](C)(C)C)c2nc(-c3cccc(C(F)F)n3)nc(Nc3ccncc3F)c12]

To a 25 mL flask was 3-fluoropyridin-4-amine (0.177 g, 1.575 mmol) and DMF (2 ml). The resulting solution was cooled to 0° C., NaH (0.173 g, 4.33 mmol) was added portionwise and stirred for 10 min. To the resulting mixture was added 2-(6-(difluoromethyl) pyridin-2-yl)-5-methyl-4-phenoxy-7-((2-(trimethylsilyl) ethoxy) methyl)-7H-pyrrolo[2,3-d]pyrimidine (0.19 g, 0.394 mmol) and stirred at room temperature for 16 h. Upon completion of reaction as judged by LCMS, the reaction mixture was quenched with ice and stirred. The resulting suspension was filtered, washed extensively with water and dried. Obtained 2-(6-(difluoromethyl) pyridin-2-yl)-N-(3-fluoropyridin-4-yl)-5-methyl-7-((2-(trimethylsilyl)ethoxy)methyl)-7H-pyrrolo[2,3-d]pyrimidin-4-amine (0.15 g, 0.300 mmol, 75%) as an off-white solid. LCMS m/z 501 (M+H); rt 0.95 min; conditions A.

To a 25 mL flask was added 2-(6-(difluoromethyl) pyridin-2-yl)-N-(3-fluoropyridin-4-yl)-5-methyl-7-((2-(trimethylsilyl)ethoxy)methyl)-7H-pyrrolo[2,3-d]pyrimidin-4-amine (0.1 g, 0.200 mmol), DCM (5 mL), cooled to 0° C. and stirred. To the resulting solution TFA (0.154 ml, 1.998 mmol) was added and the reaction mixture was stirred at room temperature for 3 h. The reaction was monitored by LCMS. Upon completion of reaction, the reaction mixture was concentrated. To the resulting residue was added 10% aqueous $NaHCO_3$ (5 mL), stirred and filtered to obtain the crude product as a brown solid. The crude material was purified via preparative LC/MS to afford Example 6 (3 mg, 7.86 μmol, 3.93%) as pale yellow solid. LCMS m/z 371.1 (M+H); rt 1.75 min; conditions C. $^1$H NMR (400 MHz, DMSO-$d_6$) δ 11.99 (br. s., 1H) 8.79 (t, J=6.48 Hz, 1H) 8.52 (d, J=2.93 Hz, 1H) 8.44 (d, J=8.07 Hz, 1H) 8.37 (d, J=5.38 Hz, 2H) 8.13 (t, J=7.83 Hz, 1H) 7.75 (d, J=7.83 Hz, 1H) 7.26 (s, 1H) 6.90-7.20 (m, 1H) 2.53 (d, J=0.98 Hz, 3H).

Scheme 7

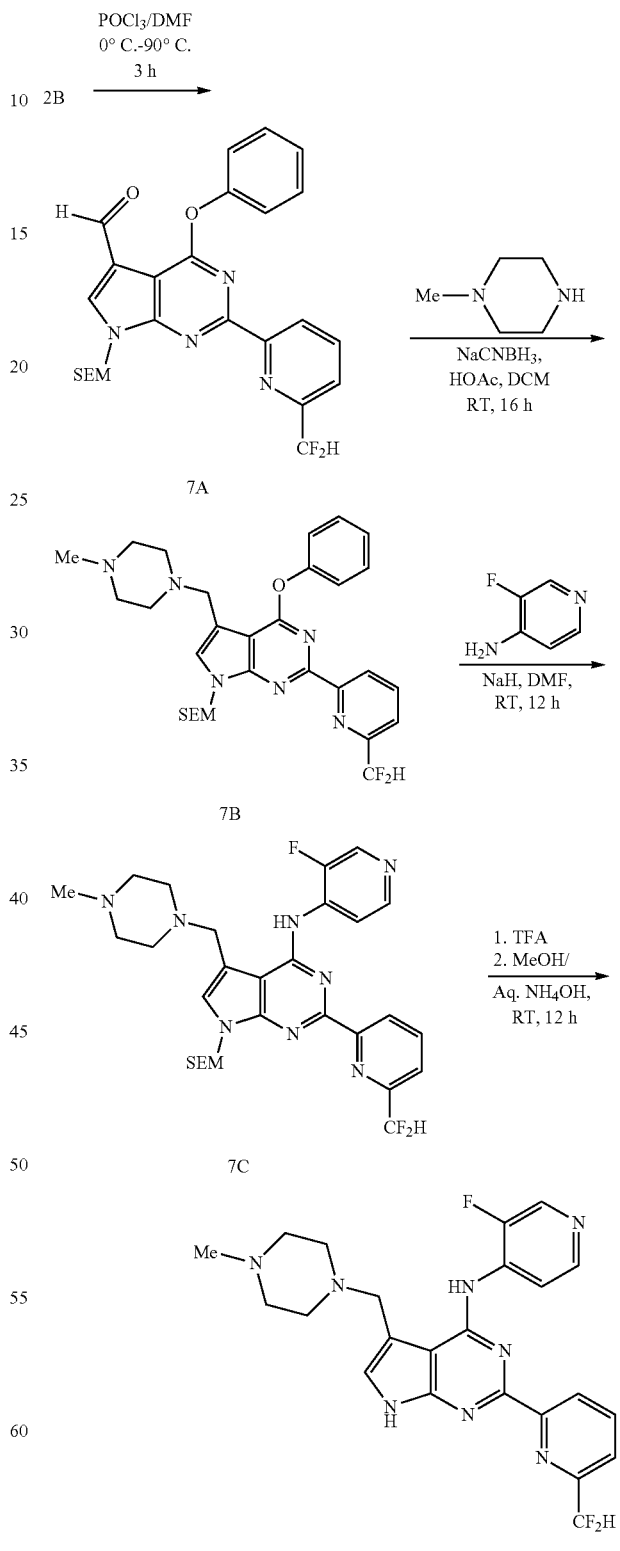

Example 7

2-(6-(difluoromethyl)pyridin-2-yl)-N-(3-fluoropyridin-4-yl)-5-((4-methylpiperazin-1-yl)methyl)-7H-pyrrolo[2,3-d]pyrimidin-4-amine

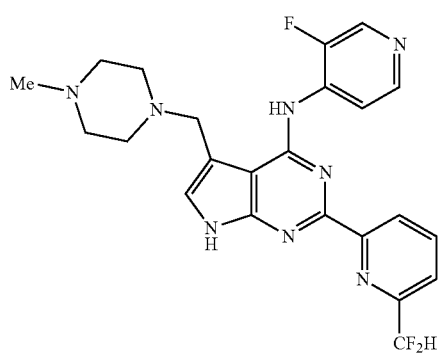 [SMILES: CN1CCN(Cc2c[nH]c3nc(-c4cccc(C(F)F)n4)nc(Nc4ccncc4F)c23)CC1]

Intermediate 7A: 2-(6-(difluoromethyl)pyridin-2-yl)-4-phenoxy-7-((2-(trimethylsilyl)ethoxy)methyl)-7H-pyrrolo[2,3-d]pyrimidine-5-carbaldehyde

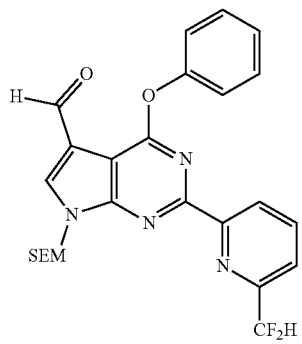 [SMILES: C[Si](C)(C)CCOCn1cc(C=O)c2c(Oc3ccccc3)nc(-c3cccc(C(F)F)n3)nc21]

To ice-cold DMF (2 mL) was dropwise added POCl$_3$ (0.119 mL, 1.280 mmol) and stirred for 30 min. To the resulting reaction mixture was dropwise added a solution of 2-(6-(difluoromethyl)pyridin-2-yl)-4-phenoxy-7-((2-(trimethylsilyl)ethoxy)methyl)-7H-pyrrolo[2,3-d]pyrimidine (300 mg, 0.640 mmol) in DMF (2 mL). The reaction mixture was heated to 90° C. and stirred for 3 h. The reaction mixture was cooled to room temperature and poured into crushed ice. Excess POCl$_3$ was quenched with 1 N NaOH and let stand at room temperature for 16 h. An aliquot of the reaction mixture was diluted with methanol and analyzed by LCMS to ensure complete conversion. The reaction mixture was diluted with water and extracted with dichloromethane. The organic layer was concentrated. The residue was purified by silica gel column chromatography (35% Ethylacetate in Hexane) to afford 2-(6-(difluoromethyl)pyridin-2-yl)-4-phenoxy-7-((2-(trimethylsilyl)ethoxy)methyl)-7H-pyrrolo[2,3-d]pyrimidine-5-carbaldehyde (170 mg, 0.229 mmol, 35.8% yield) as an off white solid. LCMS m/z 498.4 (M+H); rt 1.52 min; conditions B.

Intermediate 7B: 2-(6-(difluoromethyl)pyridin-2-yl)-5-((4-methylpiperazin-1-yl)methyl)-4-phenoxy-7-((2-(trimethylsilyl)ethoxy)methyl)-7H-pyrrolo[2,3-d]pyrimidine

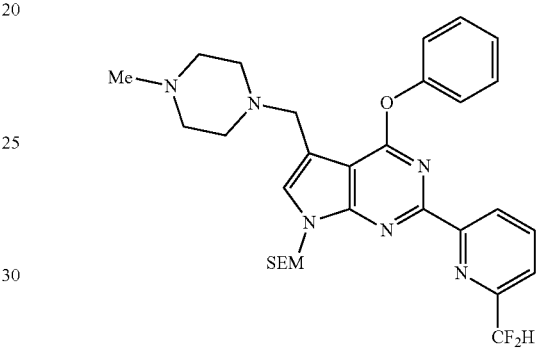

To a solution of 2-(6-(difluoromethyl)pyridin-2-yl)-4-phenoxy-7-((2-(trimethylsilyl)ethoxy)methyl)-7H-pyrrolo[2,3-d]pyrimidine-5-carbaldehyde (80 mg, 0.161 mmol) in dichloromethane (4 mL) was added 1-methylpiperazine (0.021 mL, 0.193 mmol) and acetic acid (0.0092 µL, 0.161 µmol). The reaction mixture was stirred at room temperature for 16 h. To the reaction mixture was added sodium cyanoborohydride (20.25 mg, 0.322 mmol) and stirred until the reaction was complete by LCMS. The reaction mixture was poured into water and extracted with dichloromethane. The organic phase was concentrated to afford 2-(6-(difluoromethyl)pyridin-2-yl)-5-((4-methylpiperazin-1-yl)methyl)-4-phenoxy-7-((2-(trimethylsilyl)ethoxy)methyl)-7H-pyrrolo[2,3-d]pyrimidine as a colorless liquid. LCMS m/z 581.2 (M+H); rt 4.13 min; conditions E.

To a solution of 2-(6-(difluoromethyl)pyridin-2-yl)-N-(3-fluoropyridin-4-yl)-5-((4-methylpiperazin-1-yl)methyl)-7-((2-(trimethylsilyl)ethoxy)methyl)-7H-pyrrolo[2,3-d]pyrimidin-4-amine (150 mg, 0.251 mmol) in dichloromethane (5 mL) was added TFA (0.097 mL, 1.253 mmol) and stirred the reaction mixture at room temperature for 16 h. The reaction mixture was concentrated. To the residue was added methanol (2 mL), aqueous 30% ammonium hydroxide (1 mL) and stirred the reaction mass at room temperature for 2 h. An aliquot of the reaction mixture was diluted with methanol and analyzed by LCMS to ensure complete conversion. The reaction mixture was diluted with water and extracted with dichloromethane. The organic phase was concentrated and purified by reverse phase HPLC to afford Example 7 (5.2 mg, 10.99 μmol, 4.39% yield) as a pale yellow solid. LCMS m/z 469.2 (M+H); rt 1.46 min; conditions C. ¹H NMR (400 MHz, DMSO-d₆) δ 11.38 (s, 1H), 9.49 (dd, J=5.50, 7.21 Hz, 1H), 8.75-8.85 (m, 2H), 8.66 (d, J=5.62 Hz, 1H), 8.45 (t, J=7.83 Hz, 1H), 8.03-8.10 (m, 1H), 7.71 (s, 1H), 7.20-7.51 (m, 1H), 3.98-4.04 (m, 3H), 2.59 (td, J=1.83, 3.67 Hz, 2H), 2.40 (s, 3H), 2.11 (s, 3H).

Example 8

N-(3-fluoropyridin-4-yl)-2-(pyridin-2-yl)-7H-pyrrolo[2,3-d]pyrimidin-4-amine

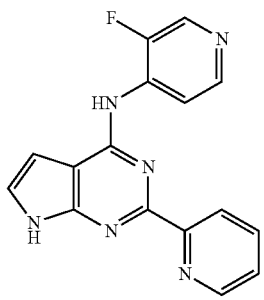 [SMILES: Fc1cnccc1Nc1nc(-c2ccccn2)nc2[nH]ccc12]

Example 8 (23.7 mg, 0.061 mmol, 26.5%) was synthesized employing the procedure described for Example 1 (Scheme 1). LCMS m/z 307.2 (M+H); rt 1.26 min; conditions E; ¹H NMR (400 MHz, DMSO-d₆) δ 12.09 (s, 1H), 9.61 (s, 1H), 8.75-8.65 (m, 1H), 8.55 (d, J=3.5 Hz, 1H), 8.42-8.28 (m, 2H), 8.00-7.80 (m, 1H), 7.50-7.33 (m, 2H), 7.00 (d, J=3.5 Hz, 1H).

Example 9

2-(pyridin-2-yl)-4-(1H-pyrrolo[3,2-c]pyridin-1-yl)-7H-pyrrolo[2,3-d]pyrimidine

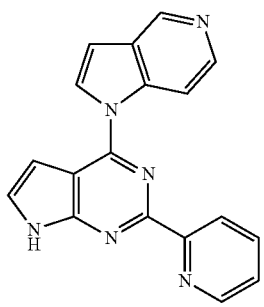 [SMILES: c1ccc(-c2nc(-n3ccc4cnccc43)c3cc[nH]c3n2)nc1]

Example 9 (3 mg, 9.22 μmo, 6.80%) was synthesized employing the procedure described for Example 1 (Scheme 1). LCMS m/z 313.1 (M+H); rt 1.40 min; conditions D: ¹H NMR (400 MHz, DMSO-d₆) δ 13.07 (br. s., 1H), 9.66-9.59 (m, 1H), 9.51 (d, J=6.4 Hz, 1H), 9.13-9.04 (m, 1H), 9.01-8.90 (m, 1H), 8.83-8.69 (m, 1H), 8.30 (td, J=7.8, 1.8 Hz, 1H), 8.20-8.09 (m, 1H), 7.87-7.76 (m, 1H), 7.66-7.57 (m, 1H), 7.54-7.43 (m, 1H), 7.35-7.28 (m, 1H).

Example 10

N-(3-fluoropyridin-4-yl)-2-(6-(trifluoromethyl)pyridin-2-yl)-7H-pyrrolo[2,3-d]pyrimidin-4-amine

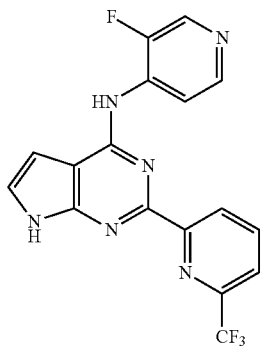

Example 10 (45.7 mg, 0.120 mmol, 43.1%) was synthesized employing the procedure described for Example 2 (Scheme 2). LCMS m/z 375.2 (M+H); rt 1.26 min; conditions E; ¹H NMR (400 MHz, DMSO-d₆) δ 12.38 (br. s., 1H), 9.97 (br. s., 1H), 8.95 (br. s., 1H), 8.68 (br. s., 2H), 8.40 (d, J=6.0 Hz, 1H), 8.26 (s, 1H), 7.98 (s, 1H), 7.53 (s, 1H), 7.29-6.71 (m, 2H).

Example 11

2-(5-fluoro-6-methylpyridin-2-yl)-N-(3-fluoropyridin-4-yl)-7H-pyrrolo[2,3-d]pyrimidin-4-amine

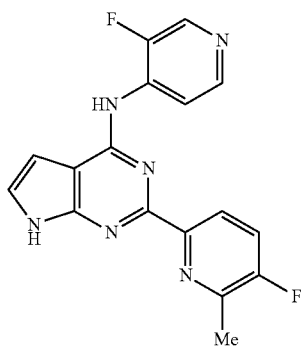 [SMILES: Cc1nc(-c2nc(Nc3ccncc3F)c3cc[nH]c3n2)ccc1F]

Example 11 (38.3 mg, 0.109 mmol, 23.15% yield) was synthesized employing the procedure described for Example 2 (Scheme 2). LCMS m/z 339.0 (M+H); rt 2.41 min; conditions E. ¹H NMR (400 MHz, DMSO-d₆) δ 12.18-12.12 (m, 1H), 9.69-9.58 (m, 1H), 8.79-8.69 (m, 1H), 8.61-8.52 (m, 1H), 8.41-8.36 (m, 1H), 8.26-8.17 (m, 1H), 7.81-7.69 (m, 1H), 7.46-7.39 (m, 1H), 7.05-6.91 (m, 1H), 2.62-2.53 (d, 3H).

Example 12

2-(6-(difluoromethyl)pyridin-2-yl)-4-(1H-pyrrolo[3,2-c]pyridin-1-yl)-7H-pyrrolo[2,3-d]pyrimidine

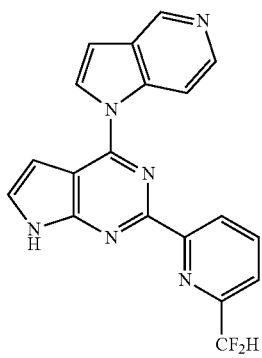 [SMILES: FC(F)c1cccc(-c2nc(-n3ccc4cnccc43)c3cc[nH]c3n2)n1]

Example 12 (13 mg, 0.035 mmol, 11.54%) was synthesized employing the procedure described for Example 2 (Scheme 2). LCMS m/z 363.2 (M+H); rt 1.962 min; conditions E; $^1$H NMR (400 MHz, DMSO-$d_6$) δ 12.81-12.75 (m, 1H), 9.02 (d, J=1.0 Hz, 1H), 8.99-8.94 (m, 1H), 8.66 (d, J=7.0 Hz, 1H), 8.50 (s, 1H), 8.42 (d, J=3.5 Hz, 1H), 8.26 (t, J=7.8 Hz, 1H), 7.90-7.79 (m, 2H), 7.32-6.98 (m, 3H).

Example 13

N-(2-chloro-5-fluoropyridin-4-yl)-2-(5-fluoro-6-methylpyridin-2-yl)-7H-pyrrolo[2,3-d]pyrimidin-4-amine

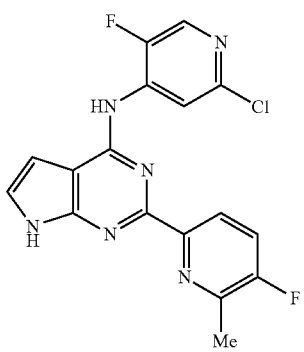 [SMILES: Cc1nc(-c2nc(Nc3cc(Cl)ncc3F)c3cc[nH]c3n2)ccc1F]

Example 13 (17.2 mg, 0.044 mmol, 11.02%) was synthesized employing the procedure described for Example 2 (Scheme 2). LCMS m/z 373.2 (M+H); rt 2.38 min; conditions E; $^1$H NMR (400 MHz, DMSO-$d_6$) δ 12.45 (br. s., 1H), 10.10-9.95 (m, 1H), 9.92-9.80 (m, 1H), 8.68-8.62 (m, 1H), 8.58-8.46 (m, 1H), 8.11-7.97 (m, 1H), 7.73 (d, J=3.7 Hz, 1H), 7.36 (d, J=3.4 Hz, 1H), 2.90 (d, J=2.9 Hz, 3H).

Example 14

2-(5-fluoropyridin-2-yl)-N-(3-fluoropyridin-4-yl)-7H-pyrrolo[2,3-d]pyrimidin-4-amine

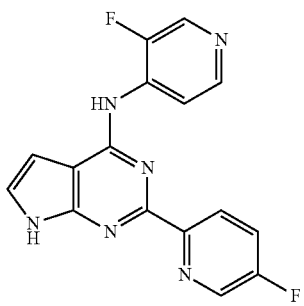 [SMILES: Fc1ccc(-c2nc(Nc3ccncc3F)c3cc[nH]c3n2)nc1]

Example 14 (10.9 mg, 0.027 mmol, 8.52% yield) was synthesized employing the procedure described for Example 2 (Scheme 2). LCMS m/z 325.0 (M+H); rt 2.39 min; conditions E, HPLC RT—8.053 min, $^1$H NMR (400 MHz, DMSO-$d_6$) δ 12.38-12.33 (m, 1H), 10.68-10.56 (br. s, 1H), 9.30-9.23 (m, 1H), 9.00-8.94 (m, 1H), 8.77-8.70 (m, 1H), 8.63-8.56 (m, 1H), 8.47-8.40 (m, 1H), 7.94-7.83 (m, 1H), 7.61-7.53 (m, 1H), 7.11-7.04 (m, 1H).

Example 15

N-(2-chloropyrimidin-4-yl)-2-(6-(difluoromethyl)pyridin-2-yl)-7H-pyrrolo[2,3-d]pyrimidin-4-amine

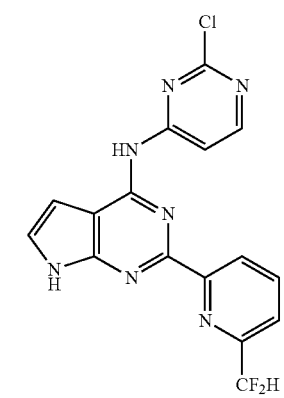 [SMILES: FC(F)c1cccc(-c2nc(Nc3ccnc(Cl)n3)c3cc[nH]c3n2)n1]

Example 15 (5.2 mg, 0.013 mmol, 5.01%) was synthesized employing the procedure described for Example 2 (Scheme 2). LCMS m/z 374.1 (M+H); rt 1.99 min; conditions C, $^1$H NMR (400 MHz, DMSO-$d_6$) δ 12.88-12.82 (m, 1H), 9.25-9.18 (m, 1H), 9.14-9.06 (m, 1H), 8.60-8.52 (m, 1H), 8.51-8.44 (m, 1H), 8.19-8.12 (m, 1H), 8.12-8.04 (m, 1H), 7.81-7.73 (m, 1H), 7.67-7.61 (m, 1H), 7.53-7.13 (m, 2H).

Example 16

N-(4-((2-(6-(difluoromethyl)pyridin-2-yl)-7H-pyrrolo[2,3-d]pyrimidin-4-yl)amino)-5-fluoropyridin-2-yl)acetamide

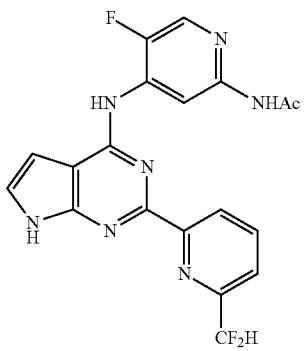 [SMILES: CC(=O)Nc1cc(Nc2nc(-c3cccc(C(F)F)n3)nc3[nH]ccc23)c(F)cn1]

Example 16 (25.2 mg, 0.059 mmol, 15.9%) was synthesized employing the procedure described for Example 3 (Scheme 3). LCMS m/z 414.2 (M+H); rt 1.62 min; conditions E; $^1$H NMR (400 MHz, DMSO-$d_6$) δ 12.26 (br. s., 1H), 10.48 (s, 1H), 9.63 (br. s., 1H), 9.15 (s, 1H), 8.73 (s, 1H), 8.31 (d, J=3.0 Hz, 1H), 8.08 (d, J=15.6 Hz, 1H), 7.75 (d, J=7.5 Hz, 1H), 7.47 (d, J=3.5 Hz, 1H), 7.26-6.69 (m, 2H), 2.08 (s, 3H).

Example 17 methyl (4-((2-(6-(difluoromethyl)pyridin-2-yl)-7H-pyrrolo[2,3-d]pyrimidin-4-yl)amino)pyridin-2-yl)carbamate

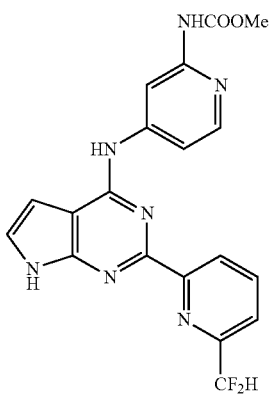

Example 17 (8 mg, 0.019 mmol, 25.5%) was synthesized employing the procedure described for Example 3 (Scheme 3). LCMS m/z 412.2 (M+H); rt 1.87 min; conditions E, $^1$H NMR (400 MHz, DMSO-$d_6$) δ 12.22 (br. s., 1H), 10.03 (s, 1H), 9.91 (s, 1H), 8.79 (s, 1H), 8.60 (d, J=2.0 Hz, 1H), 8.17 (d, J=15.6 Hz, 2H), 7.97 (s, 1H), 7.78 (d, J=7.5 Hz, 1H), 7.47 (s, 1H), 7.12-6.81 (m, 2H), 3.73 (s, 3H).

Example 18

N-(5-fluoro-4-((2-(5-fluoro-6-methylpyridin-2-yl)-7H-pyrrolo[2,3-d]pyrimidin-4-yl)amino)pyridin-2-yl)acetamide

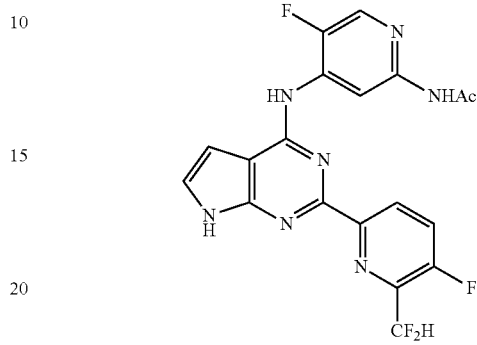

Example 18 (4.3 mg, 10.77 μmol, 6.29%) was synthesized employing the procedure described got Example 3 (Scheme 3). LCMS m/z 396.2 (M+H); rt 1.673 min; conditions E; $^1$H NMR (400 MHz, DMSO-$d_6$) δ 12.19-12.06 (m, 1H), 10.46 (s, 1H), 9.58 (s, 1H), 9.15-9.00 (m, 1H), 8.50-8.38 (m, 1H), 8.34-8.19 (m, 1H), 7.68-7.54 (m, 1H), 7.48-7.35 (m, 1H), 6.94 (br. s., 1H), 2.53 (br. s., 3H), 2.13 (s, 3H).

Example 19

1-(4-((2-(6-(difluoromethyl)pyridin-2-yl)-7H-pyrrolo[2,3-d]pyrimidin-4-yl)amino)pyridin-2-yl)pyrrolidin-2-one

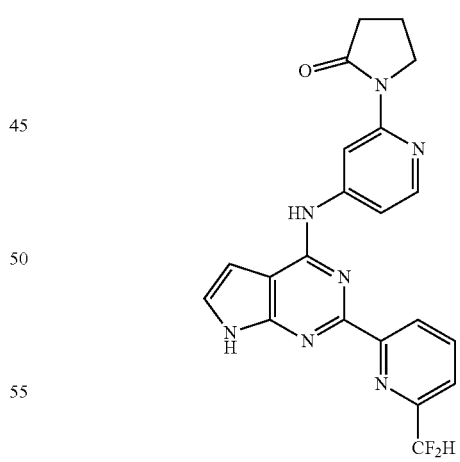

Example 19 (4.3 mg, 10.77 μmol, 6.29%) was synthesized employing the procedure described for Example 3 (Scheme 3). LCMS m/z 422.2 (M+H); rt 2.13 min; conditions E; $^1$H NMR (400 MHz, DMSO-$d_6$) δ 12.21 (br. s., 1H), 10.01-9.95 (m, 1H), 8.92-8.83 (m, 1H), 8.78-8.67 (m, 1H), 8.36-8.24 (m, 1H), 8.22-8.10 (m, 2H), 7.83-7.71 (m, 1H), 7.50-7.40 (m, 1H), 7.24-6.90 (m, 2H), 4.12-3.96 (m, 2H), 2.73-2.57 (m, 2H), 2.14-1.97 (m, 2H).

Example 20

N-(4-((2-(6-(trifluoromethyl)pyridin-2-yl)-7H-pyrrolo[2,3-d]pyrimidin-4-yl)amino)pyridin-2-yl)acetamide

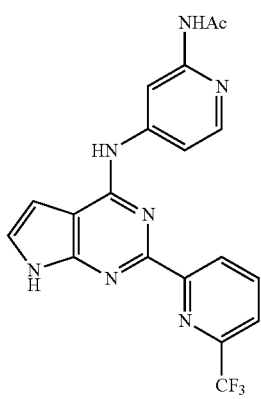 [SMILES: CC(=O)Nc1cc(Nc2nc(-c3cccc(C(F)(F)F)n3)nc3[nH]ccc23)ccn1]

Example 20 (46.8 mg, 0.112 mmol, 33.9%) was synthesized employing the procedure described for Example 3 (Scheme 3). LCMS m/z 414.2 (M+H); rt 2.02 min; conditions E; $^1$H NMR (400 MHz, DMSO-$d_6$) δ 12.31 (br. s., 1H), 8.54 (s, 1H), 8.17 (t, J=7.8 Hz, 1H), 7.82-7.67 (m, 1H), 7.55 (br. s., 1H), 7.23-7.07 (m, 1H), 6.88 (s, 1H), 5.66-5.48 (m, 1H), 5.27 (s, 2H), 3.16-2.97 (m, 1H).

Example 21

N-(4-((2-(pyridin-2-yl)-7H-pyrrolo[2,3-d]pyrimidin-4-yl)amino)pyridin-2-yl)acetamide

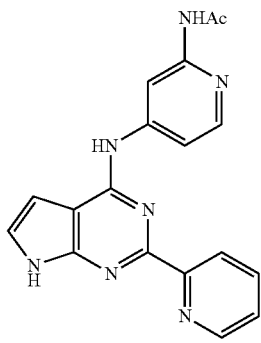 [SMILES: CC(=O)Nc1cc(Nc2nc(-c3ccccn3)nc3[nH]ccc23)ccn1]

Example 21 (31 mg, 0.088 mmol, 20.92%) was synthesized employing the procedure described for Example 3 (Scheme 3). LCMS m/z 346.2 (M+H); rt 1.38 min; conditions E; $^1$H NMR (400 MHz, DMSO-$d_6$) δ 12.07 (br. s., 1H), 10.36-10.26 (m, 1H), 9.95-9.86 (m, 1H), 8.75-8.69 (m, 1H), 8.56 (d, J=7.0 Hz, 2H), 8.26 (dd, J=5.5, 2.0 Hz, 3H), 8.00-7.82 (m, 1H), 7.46 (ddd, J=7.4, 4.9, 1.3 Hz, 2H), 6.99 (dd, J=3.5, 2.0 Hz, 1H), 2.13 (s, 3H).

Example 22

N-(4-((2-(6-methylpyridin-2-yl)-7H-pyrrolo[2,3-d]pyrimidin-4-yl)amino)pyridin-2-yl)acetamide

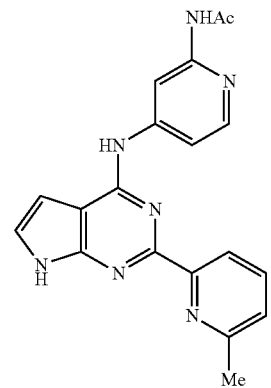 [SMILES: CC(=O)Nc1cc(Nc2nc(-c3cccc(C)n3)nc3[nH]ccc23)ccn1]

Example 22 (41 mg, 0.113 mmol, 46.1%) was synthesized employing the procedure described for Example 3 (Scheme 3). LCMS m/z 358.2 (M−H); rt 1.55 min; conditions E; $^1$H NMR (400 MHz, DMSO-$d_6$) δ 12.34 (br. s., 1H), 10.57 (s, 1H), 10.15 (s, 1H), 8.89-8.74 (m, 1H), 8.61 (s, 1H), 8.55 (dd, J=5.9, 2.0 Hz, 1H), 8.45 (d, J=5.6 Hz, 1H), 8.07 (t, J=7.7 Hz, 1H), 7.66 (d, J=3.4 Hz, 1H), 7.57 (d, J=7.3 Hz, 1H), 7.23 (d, J=3.4 Hz, 1H), 2.85 (s, 3H), 2.38 (s, 3H).

Example 23

N-(4-((2-(5-(trifluoromethyl)pyridin-2-yl)-7H-pyrrolo[2,3-d]pyrimidin-4-yl)amino)pyridin-2-yl)acetamide

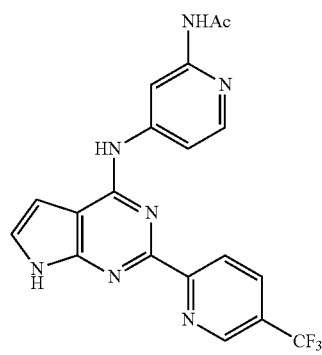 [SMILES: CC(=O)Nc1cc(Nc2nc(-c3ccc(C(F)(F)F)cn3)nc3[nH]ccc23)ccn1]

Example 23 (8.79 mg, 0.020 mmol, 11.11%) was synthesized employing the procedure described for Example 3 (Scheme 3). LCMS m/z 414.2 (M+H); rt 2.55 min; conditions E; $^1$H NMR (400 MHz, DMSO-$d_6$) δ 12.21 (br. s., 1H), 10.34 (s, 1H), 9.98 (s, 1H), 9.10 (d, J=2.0 Hz, 1H), 8.78 (d, J=8.5 Hz, 1H), 8.65 (d, J=1.5 Hz, 1H), 8.31 (dd, J=8.3, 2.3 Hz, 1H), 8.23-8.11 (m, 2H), 7.49 (d, J=3.5 Hz, 1H), 7.02 (d, J=3.5 Hz, 1H), 2.14 (s, 3H).

Example 24

N-(4-((2-(6-(trifluoromethyl)pyridin-2-yl)-7H-pyrrolo[2,3-d]pyrimidin-4-yl)amino)pyridin-2-yl)propionamide

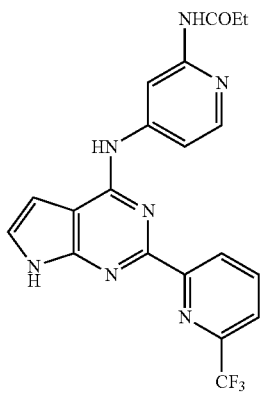

Example 24 (50.4 mg, 0.117 mmol, 81% yield) was synthesized employing the procedure described for Example 3 (Scheme 3). LSMS m/z 428 (M+H); rt 1.73 min; conditions C; $^1$H NMR (400 MHz, DMSO-$d_6$) δ 12.57-12.53 (m, 1H), 10.59-10.54 (m, 1H), 10.23-10.19 (m, 1H), 9.21-9.17 (m, 1H), 9.07-9.03 (m, 1H), 8.52-8.46 (m, 1H), 8.44-8.42 (m, 1H), 8.40-8.35 (m, 1H), 8.26-8.21 (m, 1H), 7.75-7.71 (m, 1H), 7.29-7.25 (m, 1H), 2.74-2.65 (m, 2H), 1.39 (t, J=7.6 Hz, 3H).

Example 25

N-(4-((2-(6-(difluoromethyl)pyridin-2-yl)-5-methyl-7H-pyrrolo[2,3-d]pyrimidin-4-yl)amino)pyridin-2-yl)acetamide

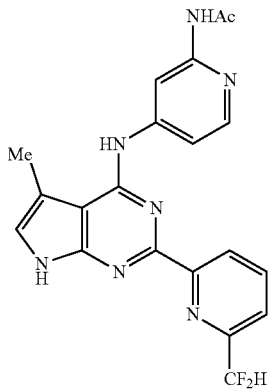 [SMILES: CC(=O)Nc1cc(Nc2nc(-c3cccc(C(F)F)n3)nc3[nH]cc(C)c23)ccn1]

Example 25 (1.5 mg, 3.66 μmol, 6.6%) was synthesized from Intermediate 6B employing the procedure described for Example 3 (Scheme 3). LCMS m/z 410.0 (M+H); rt 1.31 min; conditions D. $^1$H NMR (400 MHz, DMSO-$d_6$) δ 11.94 (s, 1H) 10.30 (s, 1H) 8.70 (s, 1H) 8.66 (d, J=8.07 Hz, 1H) 8.14 (d, J=5.62 Hz, 1H) 8.09 (t, J=7.95 Hz, 1H) 7.73 (d, J=8.31 Hz, 1H) 7.65 (dd, J=5.62, 2.20 Hz, 1H) 7.21 (s, 1H) 6.88-7.17 (m, 1H) 2.51-2.54 (m, 3H) 2.08-2.11 (d, J=0.98 Hz, 3H).

Example 26

3,3-dimethyl-N-(4-((2-(6-(trifluoromethyl)pyridin-2-yl)-7H-pyrrolo[2,3-d]pyrimidin-4-yl)amino)pyridin-2-yl)butanamide

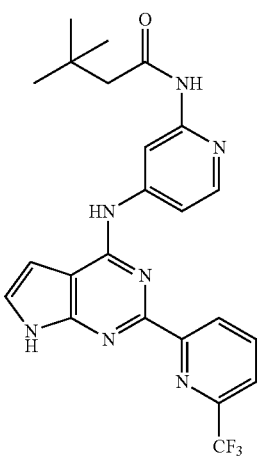 [SMILES: CC(C)(C)CC(=O)Nc1cc(Nc2nc(-c3cccc(C(F)(F)F)n3)nc3[nH]ccc23)ccn1]

Example 26 (63.6 mg, 0.135 mmol, 62.5% yield) was synthesized employing the procedure described for Example 3 (Scheme 3). LCMS m/z 470 (M+H); rt 2.14 min; conditions C; $^1$H NMR (400 MHz, DMSO-$d_6$) δ 12.56-12.52 (m, 1H), 10.50-10.47 (m, 1H), 10.22-10.19 (m, 1H), 9.18-9.15 (m, 1H), 9.02-8.99 (m, 1H), 8.43 (d, J=1.0 Hz, 3H), 8.25-8.22 (m, 1H), 7.75-7.71 (m, 1H), 7.28-7.25 (m, 1H), 2.59 (s, 2H), 1.32 (s, 9H).

Example 27

3-methyl-N-(4-((2-(6-(trifluoromethyl)pyridin-2-yl)-7H-pyrrolo[2,3-d]pyrimidin-4-yl)amino)pyridin-2-yl)butanamide

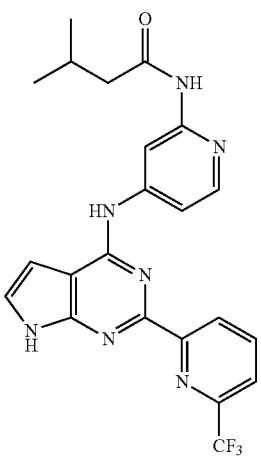 [SMILES: CC(C)CC(=O)Nc1cc(Nc2nc(-c3cccc(C(F)(F)F)n3)nc3[nH]ccc23)ccn1]

Example 27 (63.4 mg, 0.139 mmol, 45.3% yield) was synthesized employing the procedure described for Example 3 (Scheme 3). LCMS m/z 456 (M+H); rt 1.97 min; conditions C; $^1$H NMR (400 MHz, DMSO-$d_6$) δ 12.33-12.23 (m, 1H), 10.31 (s, 1H), 9.96 (s, 1H), 8.92 (d, J=8.0 Hz, 1H), 8.78

(d, J=1.5 Hz, 1H), 8.29-8.12 (m, 3H), 8.01-7.95 (m, 1H), 7.48 (dd, J=3.3, 2.3 Hz, 1H), 7.01 (dd, J=3.5, 2.0 Hz, 1H), 2.32 (d, J=7.0 Hz, 2H), 2.22-2.10 (m, 1H), 0.98 (d, J=7.0 Hz, 6H).

Example 28

N-(4-((2-(6-(trifluoromethyl)pyridin-2-yl)-7H-pyrrolo[2,3-d]pyrimidin-4-yl)amino)pyridin-2-yl)methanesulfonamide

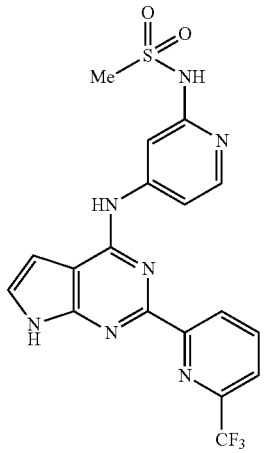 [SMILES: CS(=O)(=O)Nc1cc(Nc2nc(-c3cccc(C(F)(F)F)n3)nc3[nH]ccc23)ccn1]

Example 28 (14.2 mg, 0.031 mmol, 13.95% yield) was synthesized employing the procedure described for Example 3 (Scheme 3). LSMS m/z 450 (M+H); rt 1.31 min; conditions C; $^1$H NMR (400 MHz, DMSO-$d_6$) δ 12.47-12.31 (m, 1H), 10.19-10.06 (m, 1H), 8.92-8.81 (m, 1H), 8.31-8.18 (m, 1H), 8.07-7.67 (m, 4H), 7.60-7.46 (m, 1H), 7.11-6.88 (m, 1H), 3.08-2.88 (m, 3H).

Example 29

N-(4-((2-(5-fluoro-6-methylpyridin-2-yl)-7H-pyrrolo[2,3-d]pyrimidin-4-yl)amino)pyridin-2-yl)acetamide

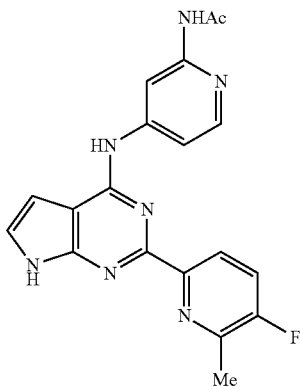 [SMILES: CC(=O)Nc1cc(Nc2nc(-c3ccc(F)c(C)n3)nc3[nH]ccc23)ccn1]

Example 29 (54.1 mg, 0.143 mmol, 95%) was synthesized employing the procedure described for Example 3 (Scheme 3). LCMS m/z 378.2 (M+H); rt 1.078 min; conditions D. $^1$H NMR (400 MHz, DMSO-$d_6$) δ 12.09 (br. s., 1H), 10.33 (s, 1H), 9.90 (s, 1H), 8.62 (s, 1H), 8.48-8.44 (m, 1H), 8.20 (d, J=1.0 Hz, 2H), 7.71 (t, J=9.0 Hz, 1H), 7.42-7.40 (m, 1H), 6.97 (dd, J=3.5, 2.0 Hz, 1H), 2.58 (d, J=2.5 Hz, 3H), 2.13 (s, 3H).

Example 30 methyl (4-((2-(6-(trifluoromethyl)pyridin-2-yl)-7H-pyrrolo[2,3-d]pyrimidin-4-yl)amino)pyridin-2-yl)carbamate

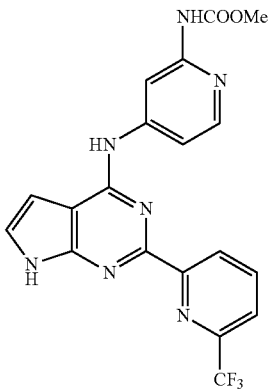

Example 30 (1.3 mg, 3.03 μmol, 2.8% yield) was synthesized employing the procedure described for Example 3 (Scheme 3). LCMS m/z 430 (M+H); rt 1.71 min; conditions C; $^1$H NMR (400 MHz, DMSO-$d_6$) δ 12.46-12.27 (m, 1H), 10.29-9.73 (m, 2H), 8.95-8.81 (m, 1H), 8.56-8.44 (m, 1H), 8.35-8.21 (m, 1H), 8.20-8.03 (m, 2H), 8.00-7.79 (m, 1H), 7.56-7.41 (m, 1H), 7.04-6.85 (m, 1H), 3.83-3.63 (s, 3H).

Example 31

N-(4-((2-(6-(difluoromethyl)pyridin-2-yl)-7H-pyrrolo[2,3-d]pyrimidin-4-yl)amino)-3-fluoropyridin-2-yl)acetamide

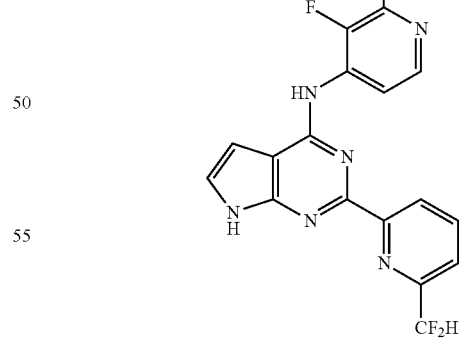

Example 31 (11 mg, 0.026 mmol, 27.8%) was synthesized employing the procedure described for Example 3 (Scheme 3). LCMS m/z 414.1 (M+H); rt 1.14 min; conditions C; $^1$H NMR (400 MHz, DMSO-$d_6$) δ 12.22 (br. s., 1H) 10.19 (s, 1H) 9.75 (s, 1H) 8.60 (t, J=5.62 Hz, 1H) 8.54 (d, J=7.83 Hz, 1H) 8.09-8.21 (m, 2H) 7.76 (d, J=7.58 Hz, 1H) 7.46 (dd, J=3.42, 2.45 Hz, 1H) 6.91-7.24 (m, 2H) 2.11 (s, 3H).

Example 32

2-morpholino-N-(4-((2-(6-(trifluoromethyl)pyridin-2-yl)-7H-pyrrol[2,3-d]pyrimidin-4-yl)amino)pyridin-2-yl)acetamide

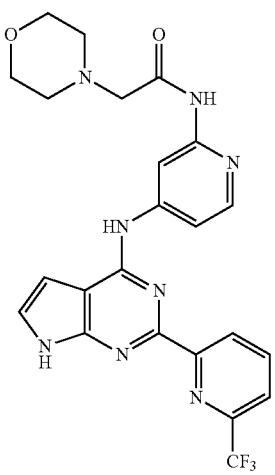 [SMILES: O=C(CN1CCOCC1)Nc1cc(Nc2nc(-c3cccc(C(F)(F)F)n3)nc3[nH]ccc23)ccn1]

Example 32 (16.8 mg, 0.034 mmol, 23.54%) was synthesized employing the procedure described for Example 4 (Scheme 4). LCMS m/z 499.2 (M+H); rt 1.72 min; $^1$H NMR (400 MHz, DMSO-d$_6$) δ 12.30 (br. s., 1H), 10.03-9.99 (m, 1H), 9.86 (s, 1H), 8.90 (d, J=8.0 Hz, 1H), 8.77 (s, 1H), 8.27-8.17 (m, 3H), 7.99 (s, 1H), 7.49 (dd, J=3.5, 2.5 Hz, 1H), 7.01 (br. s., 1H), 3.67 (d, J=4.5 Hz, 4H), 3.25 (s, 3H), 2.59 (d, J=4.0 Hz, 4H).

Example 33

N-(3-fluoropyridin-4-yl)-5-methyl-2-(6-methylpyridin-2-yl)-7H-pyrrolo[2,3-d]pyrimidin-4-amine

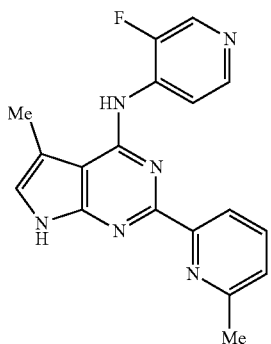 [SMILES: Cc1cccc(-c2nc(Nc3ccncc3F)c3c(C)c[nH]c3n2)n1]

Example 33 (8 mg, 0.023 mmol, 15.5%) was synthesized employing the procedure described for Example 6 (Scheme 6). LCMS m/z 335.2 (M+H); rt 2.17 min; conditions E; $^1$H NMR (400 MHz, Methanol-d$_4$) δ 9.01 (dd, J=7.0, 5.5 Hz, 1H), 8.44 (d, J=3.0 Hz, 1H), 8.36 (d, J=5.5 Hz, 1H), 8.27 (d, J=8.0 Hz, 1H), 7.89 (t, J=7.8 Hz, 1H), 7.38 (d, J=7.5 Hz, 1H), 7.18 (d, J=1.0 Hz, 1H), 2.69 (s, 3H).

Example 34

N-(3-fluoropyridin-4-yl)-5-methyl-2-(6-(trifluoromethyl)pyridin-2-yl)-7H-pyrrolo[2,3-d]pyrimidin-4-amine

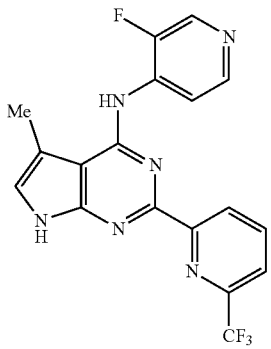

Example 34 (3 mg, 7.53 mol, 7.8%) was synthesized employing the procedure described for Example 6 (Scheme 6). LCMS m/z 389.1 (M+H); rt 1.83 min; conditions C. $^1$H NMR (400 MHz, DMSO-d$_6$) δ 12.13 (s, 1H) 8.86 (dd, J=6.97, 5.75 Hz, 1H) 8.55-8.66 (m, 3H) 8.37 (d, J=5.62 Hz, 1H) 8.25 (t, J=7.83 Hz, 1H) 7.98 (d, J=7.83 Hz, 1H) 7.29-7.35 (m, 1H) 2.55 (s, 3H).

Example 35

1-(((2-(6-(difluoromethyl)pyridin-2-yl)-4-((3-fluoropyridin-4-yl)amino)-7H-pyrrolo[2,3-d]pyrimidin-5-yl)methyl)amino)-2-methylpropan-2-ol

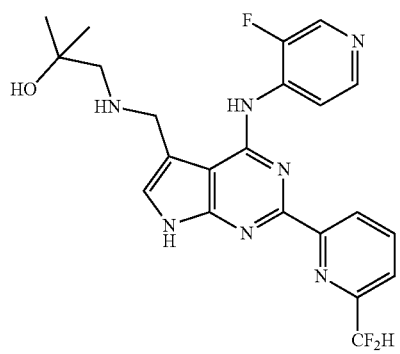 [SMILES: CC(C)(O)CNCc1c[nH]c2nc(-c3cccc(C(F)F)n3)nc(Nc3ccncc3F)c12]

To a flask containing 1-(((2-(6-(difluoromethyl)pyridin-2-yl)-4-((3-fluoropyridin-4-yl)amino)-7-((2-(trimethylsilyl)ethoxy)methyl)-7H-pyrrolo[2,3-d]pyrimidin-5-yl)methyl)amino)-2-methylpropan-2-ol (120 mg, 0.204 mmol) in dioxane (4 mL) was added 4 M HCl in 1,4-dioxane (0.510 mL, 2.04 mmol) and stirred at room temperature for 16 h. The reaction mixture was concentrated. To the residue was added methanol (2 mL), 30% aqueous ammonium hydroxide (1 mL) and stirred for 2 h. An aliquot of the reaction mixture was diluted with methanol and analyzed by LCMS to ensure complete conversion. The reaction mixture was diluted with water and extracted with dichloromethane. The organic phase was concentrated. The residue was purified by reverse phase HPLC to afford Example 35 (7.9 mg, 0.017 mmol, 8.1% yield) as a pale yellow solid. LCMS m/z 458.2 (M+H); rt 1.60 min; conditions C. $^1$H NMR (400 MHz, DMSO-d$_6$) δ 12.32 (br. s., 1H), 9.59 (dd, J=5.62, 7.34 Hz, 1H), 8.79-8.83 (m, 1H), 8.76 (d, J=3.42 Hz, 1H), 8.63 (d, J=5.62 Hz, 1H), 8.45 (t, J=7.83 Hz, 1H), 8.06 (d, J=7.34 Hz, 1H), 7.68 (s, 1H), 7.21-7.52 (m, 2H), 4.26 (s, 2H), 2.71 (br. s., 2H), 1.32 (s, 6H).

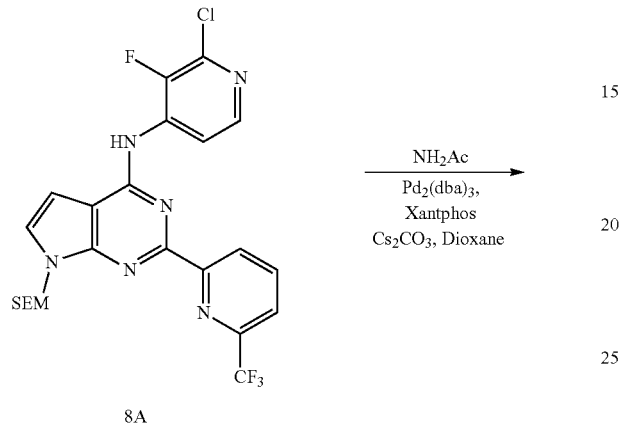

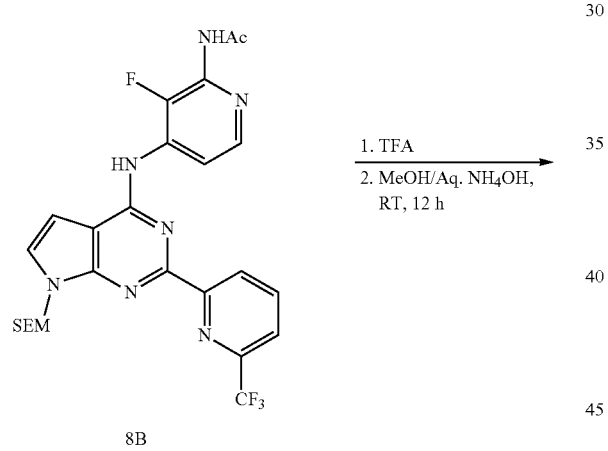

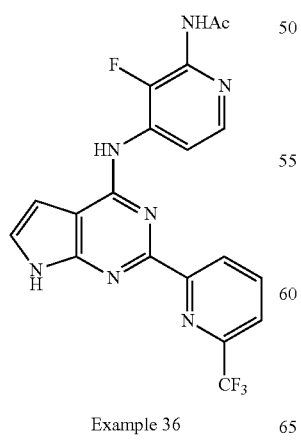

Example 36

Example 36

N-[3-fluoro-4-({2-[6-(trifluoromethyl)pyridin-2-yl]-7H-pyrrolo[2,3-d]pyrimidin-4-yl}amino)pyridin-2-yl]acetamide

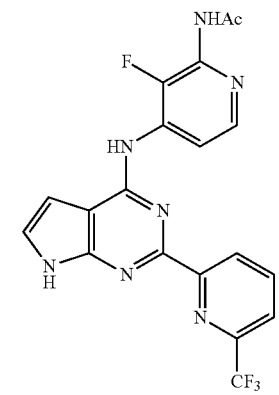 [SMILES: CC(=O)Nc1nccc(Nc2nc(-c3cccc(C(F)(F)F)n3)nc3[nH]ccc23)c1F]

Intermediate 8A: Intermediate 8A was synthesized employing the procedure described for intermediate 1E (Scheme 1).

Intermediate 8B: N-(3-fluoro-4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)acetamide

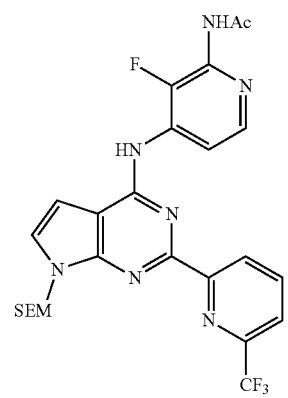 [SMILES: CC(=O)Nc1nccc(Nc2nc(-c3cccc(C(F)(F)F)n3)nc3c2ccn3COCC[Si](C)(C)C)c1F]

Intermediate 8B was synthesized employing the procedure described for Example 3 (Scheme 3). The crude compound was purified via silica gel chromatography (1:1 Hex/EtOAc) to afford 8B (0.1 g, 0.178 mmol, 48%) as pale yellow solid. LCMS: m/z 562.2 (M+H); rt 3.26 min; Conditions E.

Example 36 (2.0 mg, 4.54 μmol, 2.55%) was synthesized employing the procedure described for Example 1 (Scheme 1). LCMS: m/z 432.1 (M+H); rt 1.26 min; Conditions C. $^1$H NMR (400 MHz, DMSO-d$_6$) δ 12.29 (br. s., 1H) 10.20 (s, 1H) 9.80 (s, 1H) 8.60-8.70 (m, 2H) 8.19-8.25 (m, 1H) 8.14 (d, J=5.52 Hz, 1H) 7.96 (d, J=7.53 Hz, 1H) 7.46-7.50 (m, 1H) 7.07 (dd, J=3.51, 2.01 Hz, 1H) 2.11 (s, 3H).

Example 37

3-methyl-N-{2-[6-(trifluoromethyl)pyridin-2-yl]-7H-pyrrolo[2,3-d]pyrimidin-4-yl}pyridin-4-amine

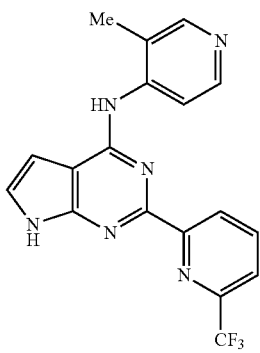

Example 37 (9.5 mg, 0.025 mmol, 24.91% yield) was synthesized employing the procedure described for Example 1 (Scheme 1). LCMS: m/z 371.0 (M+H); rt 1.34 min; Conditions G. $^1$H NMR (DMSO-d6) δ 12.25 (br. s., 1H), 8.51 (d, J=8.0 Hz, 1H), 8.42 (s, 1H), 8.37 (d, J=5.3 Hz, 1H), 8.20 (t, J=7.9 Hz, 1H), 8.14 (d, J=5.4 Hz, 1H), 7.93 (d, J=7.7 Hz, 1H), 7.45 (br. s., 1H), 6.82 (br. s., 1H), 2.36 (s, 3H).

Example 38

N-methyl-N-{2-[6-(trifluoromethyl)pyridin-2-yl]-7H-pyrrolo[2,3-d]pyrimidin-4-yl}pyridin-4-amine

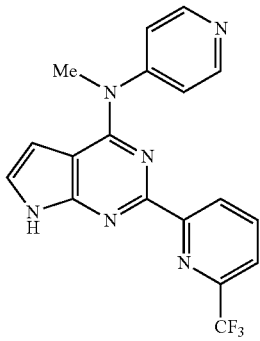 [SMILES: CN(c1ccncc1)c1nc(-c2cccc(C(F)(F)F)n2)nc2[nH]ccc12]

Example 38 was synthesized employing the procedure described for Example 1 (Scheme 1). LCMS: m/z 371.0 (M+H); rt 1.45 min; Conditions G. $^1$H NMR (DMSO-d6) δ 12.28 (br. s., 1H), 8.67 (d, J=7.9 Hz, 1H), 8.52 (d, J=4.9 Hz, 2H), 8.23 (t, J=7.9 Hz, 1H), 7.96 (d, J=7.7 Hz, 1H), 7.38 (d, J=5.8 Hz, 2H), 7.32-7.35 (m, 1H), 5.61 (br. s., 1H), 3.75 (s, 3H).

Example 39

3-(trifluoromethyl)-N-{2-[6-(trifluoromethyl)pyridin-2-yl]-7H-pyrrolo[2,3-d]pyrimidin-4-yl}pyridin-4-amine

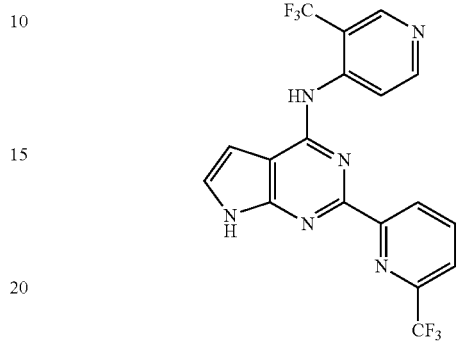

Example 39 (7.4 mg, 0.017 mmol, 16.59% yield) was synthesized employing the procedure described for Example 1 (Scheme 1). LCMS: m/z 425.1 (M+H); rt 1.74 min; Conditions G. $^1$H NMR (DMSO-d6) δ 10.70 (br. s., 1H), 8.74 (s, 1H), 8.56 (t, J=5.4 Hz, 1H), 8.38 (d, J=7.7 Hz, 1H), 7.89 (d, J=7.6 Hz, 1H), 7.83 (s, 1H), 7.59 (t, J=7.7 Hz, 1H), 7.32 (br. s., 1H), 6.87 (br. s., 1H), 6.66-6.79 (m, J=2.6 Hz, 1H).

Example 40

3-chloro-N-{2-[6-(trifluoromethyl)pyridin-2-yl]-7H-pyrrolo[2,3-d]pyrimidin-4-yl}pyridin-4-amine

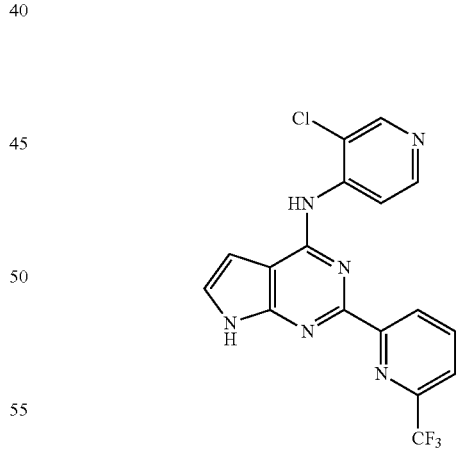

Example 40 (10.0 mg, 0.024 mmol, 23.36% yield) was synthesized employing the procedure described for Example 1 (Scheme 1). LCMS: m/z 391.3 (M+H); rt 1.94 min; Conditions G. $^1$H NMR (DMSO-d6) δ 8.64 (s, 1H), 8.52-8.61 (m, 2H), 8.46 (d, J=5.6 Hz, 1H), 8.23 (t, J=7.9 Hz, 1H), 7.96 (d, J=7.7 Hz, 1H), 7.51 (d, J=3.4 Hz, 1H), 6.93 (d, J=3.3 Hz, 1H).

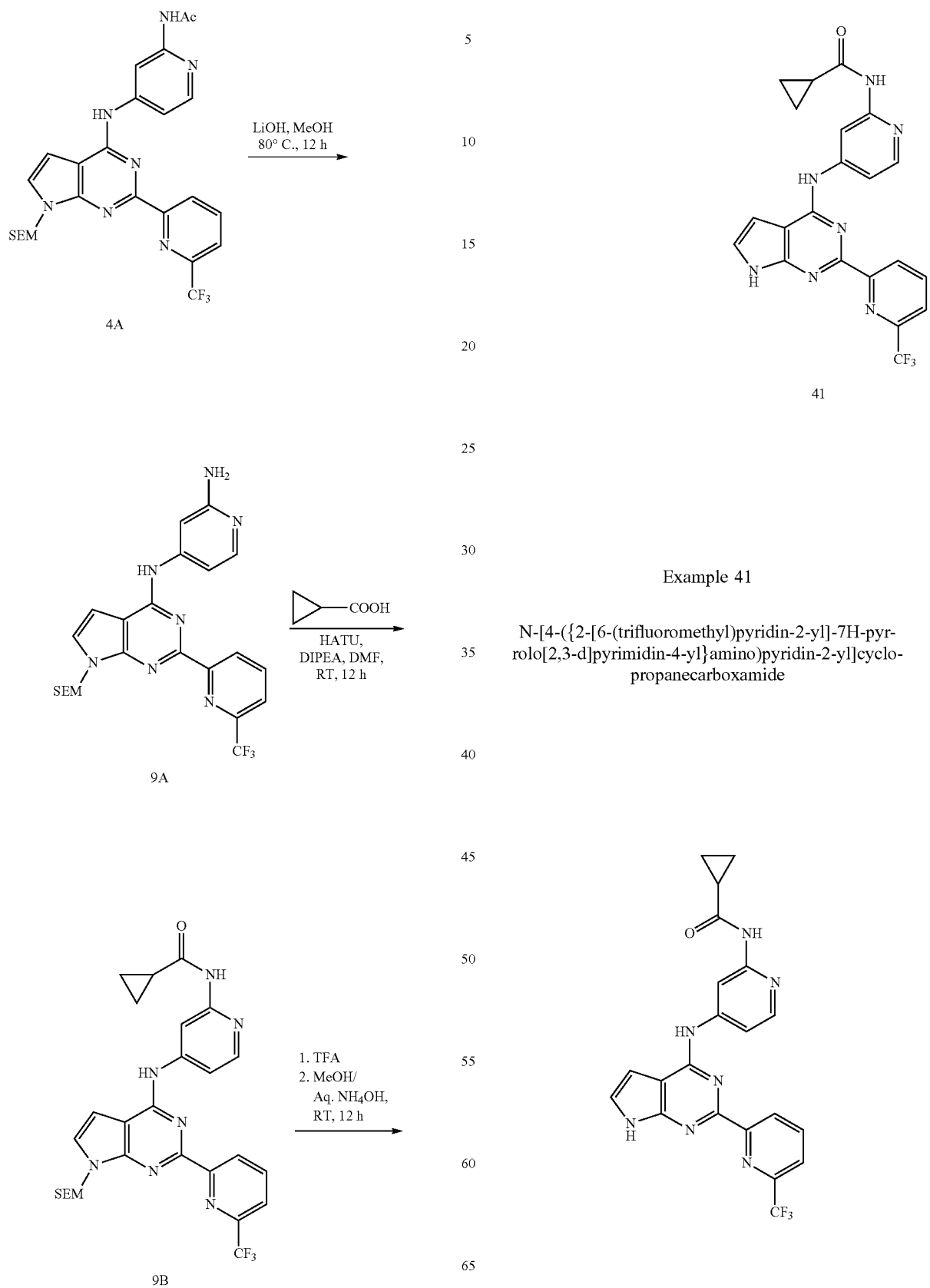
Example 41
N-[4-({2-[6-(trifluoromethyl)pyridin-2-yl]-7H-pyrrolo[2,3-d]pyrimidin-4-yl}amino)pyridin-2-yl]cyclopropanecarboxamide Intermediate 9A: N⁴-(2-(6-(trifluoromethyl)pyridin-2-yl)-7-((2-(trimethylsilyl)ethoxy)methyl)-7H-pyrrolo[2,3-d]pyrimidin-4-yl)pyridine-2,4-diamine

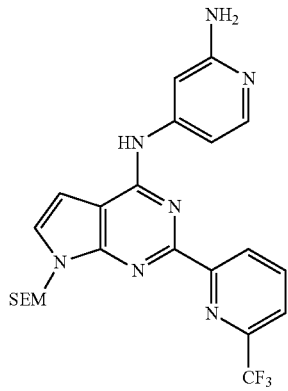 [SMILES: C[Si](C)(C)CCOCn1ccc2c(Nc3ccnc(N)c3)nc(-c3cccc(C(F)(F)F)n3)nc21]

Intermediate 9A (80 mg, 0.160 mmol, 87% yield) was synthesized employing the procedure described for Intermediate 4B (Scheme 4). LCMS: m/z 502.5 (M+H); rt 4.02 min: Conditions E.

Intermediate 9B: N-(4-((2-(6-(trifluoromethyl)pyridin-2-yl)-7-((2-(trimethylsilyl)ethoxy)methyl)-7H-pyrrolo[2,3-d]pyrimidin-4-yl)amino)pyridin-2-yl)cyclopropanecarboxamide

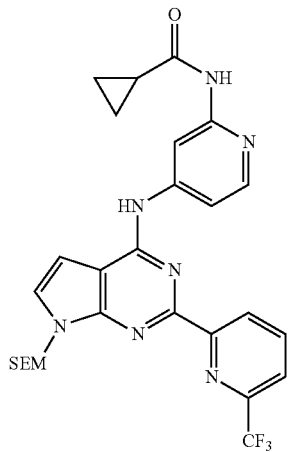 [SMILES: C[Si](C)(C)CCOCn1ccc2c(Nc3ccnc(NC(=O)C4CC4)c3)nc(-c3cccc(C(F)(F)F)n3)nc21]

Intermediate 9B (80 mg, 0.140 mmol, 88% yield was synthesized employing the procedure described for Example 4C (Scheme 4). The crude compound was used in the next reaction without further purification. LCMS: m/z 570.2 (M+H); rt 3.95 min; Condition E.

Example 41 (6.0 mg, 0.014 mmol, 9.6%) was synthesized employing the procedure described for Example 1 (Scheme 1). LCMS: m/z 440.1 (M+H); rt 1.83 min; Condition C. ¹H NMR (400 MHz, DMSO-d₆) δ 12.28 (br. s., 1H) 10.67 (s, 1H) 9.92 (s, 1H) 8.90 (d, J=7.83 Hz, 1H) 8.78 (s, 1H) 8.14-8.21 (m, 2H) 8.08 (dd, J=5.87, 1.71 Hz, 1H) 7.97 (d, J=7.83 Hz, 1H) 7.45-7.48 (m, 1H) 6.97-7.01 (m, 1H) 2.02-2.09 (m, 1H) 0.80-0.89 (m, 4H).

Example 42

3-methoxy-N-{2-[6-(trifluoromethyl)pyridin-2-yl]-7H-pyrrolo[2,3-d]pyrimidin-4-yl}pyridin-4-amine

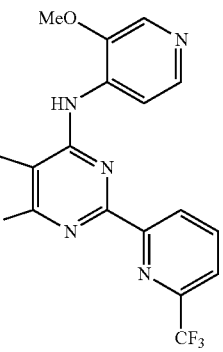

Example 42 (3.4 mg, mmol, 6.9% yield) was synthesized employing the procedure described for Example 1 (Scheme 1). LCMS: m/z 387.2 (M+H); rt 1.50 min; Conditions G. ¹H NMR (DMSO-d6) δ 12.19 (br. s., 1H), 8.86 (d, J=5.2 Hz, 1H), 8.82 (s, 1H), 8.60 (d, J=8.0 Hz, 1H), 8.30 (s, 1H), 8.23 (t, J=7.8 Hz, 1H), 8.15 (d, J=5.1 Hz, 1H), 7.95 (d, J=7.7 Hz, 1H), 7.45 (br. s., 1H), 6.95 (br. s., 1H), 3.99 (s, 3H).

Scheme 10

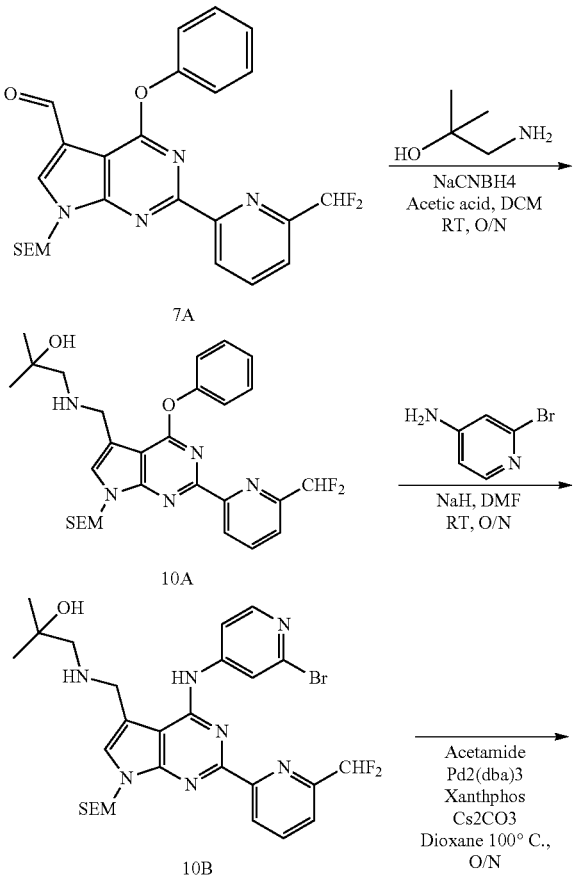

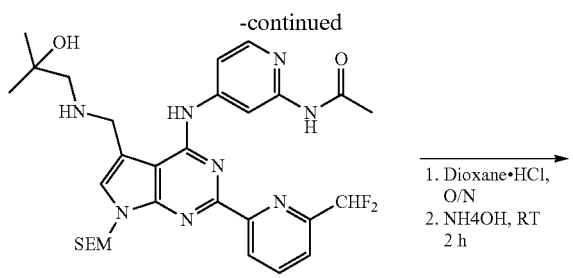

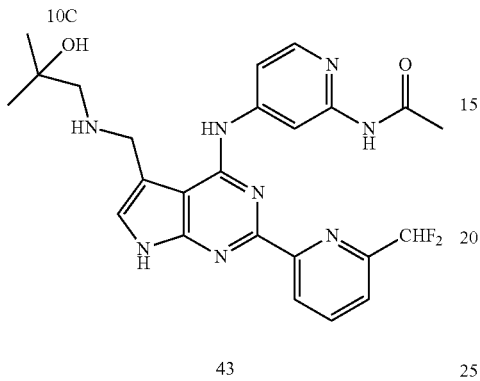

Example 43

N-[4-({2-[6-(difluoromethyl)pyridin-2-yl]-5-{[(2-hydroxy-2-methylpropyl)amino]methyl}-7H-pyrrolo[2,3-d]pyrimidin-4-yl}amino)pyridin-2-yl]acetamide

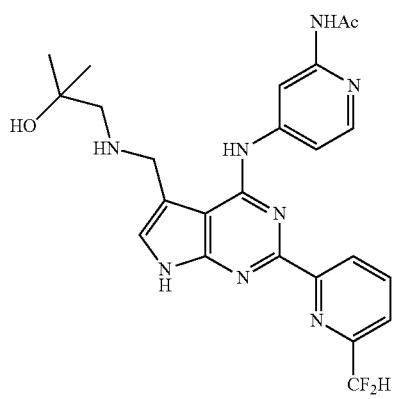 [SMILES: CC(=O)Nc1cc(Nc2nc(-c3cccc(C(F)F)n3)nc3[nH]cc(CNCC(C)(C)O)c23)ccn1]

Intermediate 10A: 1-(((2-(6-(difluoromethyl)pyridin-2-yl)-4-phenoxy-7-((2-(trimethylsilyl)ethoxy)methyl)-7H-pyrrolo[2,3-d]pyrimidin-5-yl)methyl)amino)-2-methylpropan-2-ol

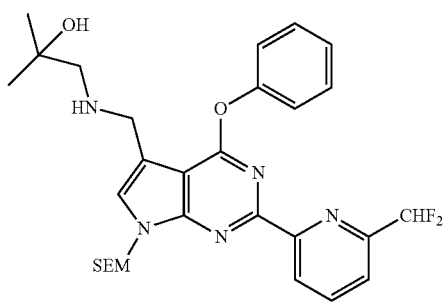 [SMILES: CC(C)(O)CNCc1cn(COCC[Si](C)(C)C)c2nc(-c3cccc(C(F)F)n3)nc(Oc3ccccc3)c12]

Intermediate 10A (crude yield, 140 mg) was synthesized employing the procedure described for Example 7B (Scheme 7). LCMS: m/z 570.8 (M+H); rt 1.36 min; Conditions B.

Intermediate 10B: 1-(((4-((2-bromopyridin-4-yl)amino)-2-(6-(difluoromethyl)pyridin-2-yl)-7-((2-(trimethylsilyl)ethoxy)methyl)-7H-pyrrolo[2,3-d]pyrimidin-5-yl)methyl)amino)-2-methylpropan-2-ol

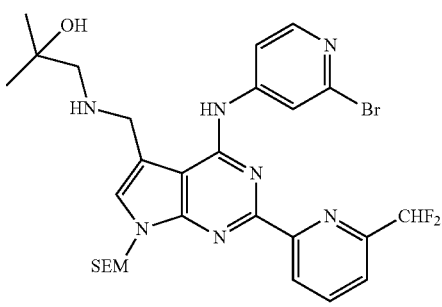 [SMILES: CC(C)(O)CNCc1cn(COCC[Si](C)(C)C)c2nc(-c3cccc(C(F)F)n3)nc(Nc3ccnc(Br)c3)c12]

Intermediate 10B (crude, 80 mg) was synthesized employing the procedure described for Example 7C (Scheme 7). LCMS: m/z 650.3; rt 1.33 min; Conditions B.

Intermediate 10C: N-(4-((2-(6-(difluoromethyl)pyridin-2-yl)-5-(((2-hydroxy-2-methylpropyl)amino)methyl)-7-((2-(trimethylsilyl)ethoxy)methyl)-7H-pyrrolo[2,3-d]pyrimidin-4-yl)amino)pyridin-2-yl)acetamide

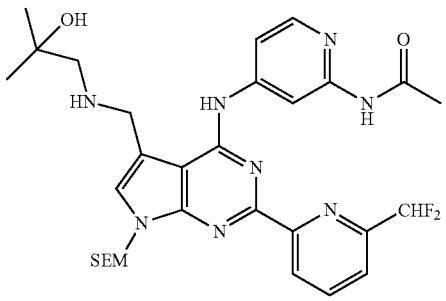 [SMILES: CC(=O)Nc1cc(Nc2nc(-c3cccc(C(F)F)n3)nc3c2c(CNCC(C)(C)O)cn3COCC[Si](C)(C)C)ccn1]

Intermediate 10C was synthesized employing the procedure described for Example 3 (Scheme 3). The crude compound was purified by silica gel column chromatography eluted with 5% Methanol in Dichloromethane to afford 10C (50 mg, 0.059 mmol, 47.9% yield) as a off white solid. LCMS: m/z 627.7; rt 1.28 min; Conditions B.

Example 43 (3.3 mg, 6.83% yield) was synthesized employing the procedure described for Example 1 (Scheme 1). LCMS: m/z 394.1 (M+H); rt 1.62 min; Conditions C. $^1$H NMR (400 MHz, DMSO-$d_6$) δ 12.34 (s, 1H), 12.00 (s, 1H), 10.32 (s, 1H), 8.81-8.93 (m, 2H), 8.07-8.20 (m, 2H), 7.77 (d, J=7.53 Hz, 1H), 7.63 (dd, J=2.01, 5.52 Hz, 1H), 7.37 (d, J=2.01 Hz, 1H), 6.88-7.24 (m, 2H), 4.40 (s, 2H), 3.90-4.06 (m, 3H), 3.08 (br. s., 2H), 2.13 (s, 3H), 1.04-1.17 (m, 6H).

Scheme 11

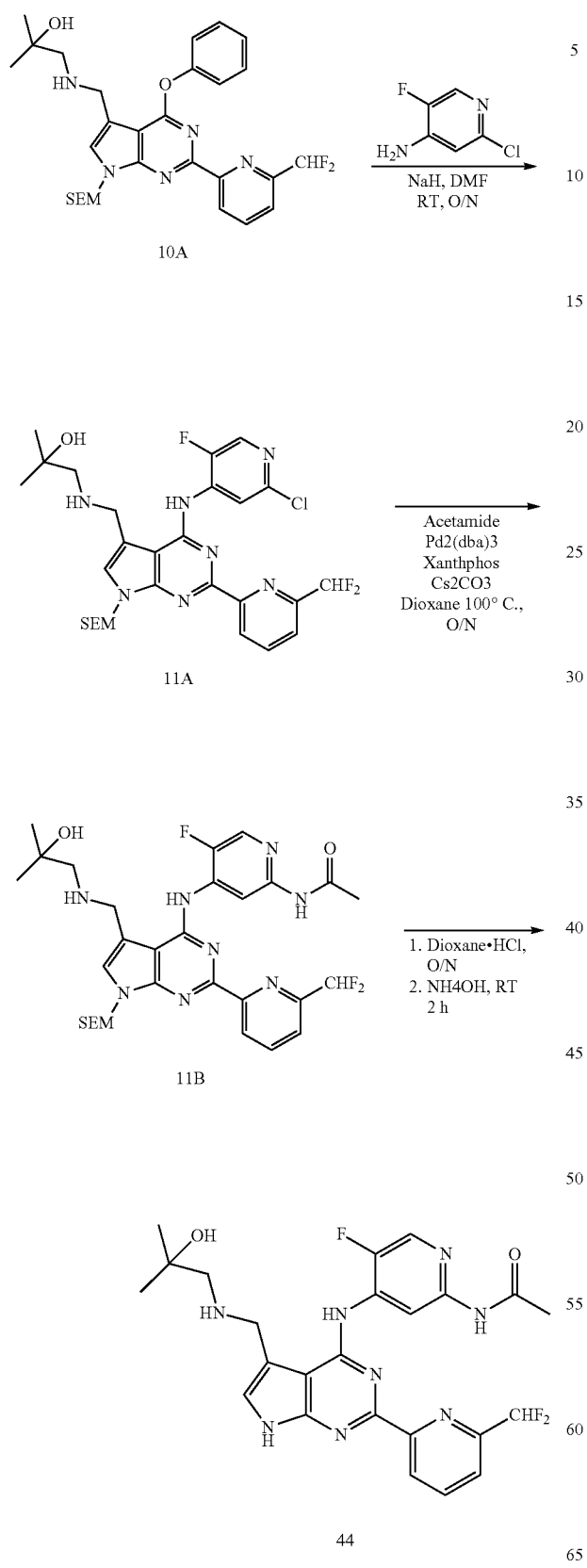

Example 44

N-[4-({2-[6-(difluoromethyl)pyridin-2-yl]-5-{[(2-hydroxy-2-methylpropyl)amino]methyl}-7H-pyrrolo[2,3-d]pyrimidin-4-yl}amino)-5-fluoropyridin-2-yl]acetamide

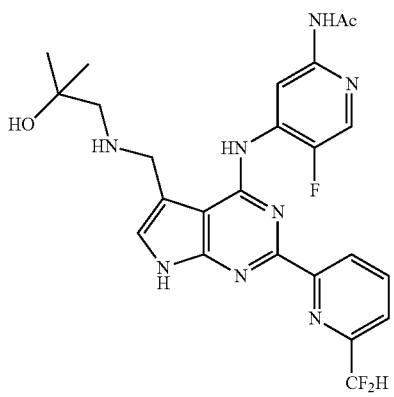

Intermediate 11A: 1-(((4-((2-chloro-5-fluoropyridin-4-yl)amino)-2-(6-(difluoromethyl)pyridin-2-yl)-7-((2-(trimethylsilyl)ethoxy)methyl)-7H-pyrrolo[2,3-d]pyrimidin-5-yl)methyl)amino)-2-methylpropan-2-ol

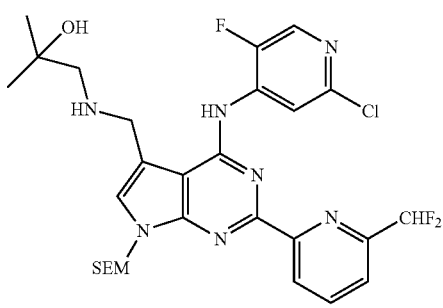 [SMILES: CC(C)(O)CNCc1cn(COCC[Si](C)(C)C)c2nc(-c3cccc(C(F)F)n3)nc(Nc3cc(Cl)ncc3F)c12]

Intermediate 11A was synthesized employing the procedure described for Example 7C (Scheme 7). The crude compound was purified by silica gel column chromatography eluted with 55% Ethylacetate in Hexane to afford 11A (120 mg, 0.112 mmol, 19.3% yield) as a off white solid. LCMS: m/z 622.7 (M+H); rt 1.60 min; Conditions B.

Intermediate 11B: N-(4-((2-(6-(difluoromethyl)pyridin-2-yl)-5-(((2-hydroxy-2-methylpropyl)amino)methyl)-7-((2-(trimethylsilyl)ethoxy)methyl)-7H-pyrrolo[2,3-d]pyrimidin-4-yl)amino)-5-fluoropyridin-2-yl)acetamide

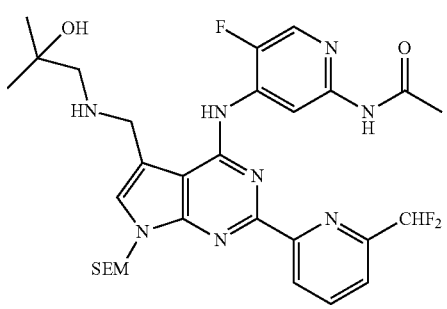 [SMILES: CC(=O)Nc1cc(Nc2nc(-c3cccc(C(F)F)n3)nc3c2c(CNCC(C)(C)O)cn3COCC[Si](C)(C)C)c(F)cn1]

Intermediate 11B was synthesized employing the procedure described for Example 3 (Scheme 3). The crude compound was purified by silica gel column chromatography eluted with 55% Ethylacetate in Petether to afford 11B (100 mg, 0.107 mmol, 55.5% yield) as a off white solid. LCMS: m/z 645.8; rt 1.26 min; Conditions B.

Example 44 (8.4 mg, 0.016 mmol, 13.03% yield) was synthesized employing the procedure described for Example 1 (Scheme 1). LCMS: m/z, 515.2 (M+H); rt 1.66 min; condition C. $^1$H NMR (400 MHz, DMSO-d$_6$) δ 12.09 (s, 1H), 10.38 (s, 1H), 9.68 (d, J=6.60 Hz, 1H), 9.01 (d, J=7.83 Hz, 1H), 8.23 (d, J=2.93 Hz, 1H), 8.10 (t, J=7.83 Hz, 2H), 7.76 (d, J=7.34 Hz, 1H), 7.41 (d, J=2.20 Hz, 1H), 6.90-7.22 (m, 3H), 4.35 (s, 2H), 3.99 (s, 2H), 2.39-2.45 (m, 3H), 2.14 (s, 3H), 0.99-1.07 (m, 6H).

Example 45

N-[2-(5-fluoro-6-methylpyridin-2-yl)-7H-pyrrolo[2,3-d]pyrimidin-4-yl]-3-methylpyridin-4-amine

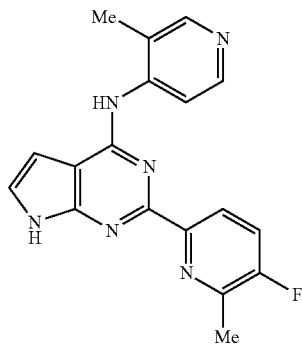 [SMILES: Cc1cnccc1Nc1nc(-c2ccc(F)c(C)n2)nc2[nH]ccc12]

Example 45 (23.5 mg, 0.070 mmol, 62.7% yield) was synthesized employing the procedure described for Example 1 (Scheme 1). LCMS: m/z 335.0 (M+H); rt 1.22 min; Conditions G. $^1$H NMR (DMSO-d6) δ 12.04 (br. s., 1H), 8.96 (s, 1H), 8.40 (s, 1H), 8.37 (d, J=5.4 Hz, 1H), 8.10-8.18 (m, 1H), 8.04 (d, J=5.1 Hz, 1H), 7.71 (t, J=8.9 Hz, 1H), 7.38 (br. s., 1H), 6.76 (br. s., 1H), 2.53 (br. s., 3H), 2.34 (s, 3H).

Example 46

N-[2-(5-fluoro-6-methylpyridin-2-yl)-7H-pyrrolo[2,3-d]pyrimidin-4-yl]-3-methoxypyridin-4-amine

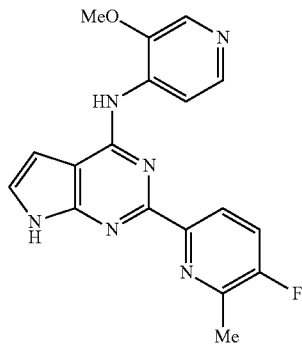 [SMILES: COc1cnccc1Nc1nc(-c2ccc(F)c(C)n2)nc2[nH]ccc12]

Example 46 (17.4 mg, 0.047 mmol, 42.5% yield) was synthesized employing the procedure described for Example 1 (Scheme 1). LCMS: m/z 351.0 (M+H); rt 1.31 min; Conditions G. $^1$H NMR (DMSO-d6) δ 12.09 (br. s., 1H), 8.61-9.00 (m, 2H), 8.33 (s, 1H), 8.18-8.27 (m, 2H), 7.75 (t, J=8.9 Hz, 1H), 7.41 (br. s., 1H), 6.92 (br. s., 1H), 4.01 (s, 3H), 2.56 (br. s., 2H).

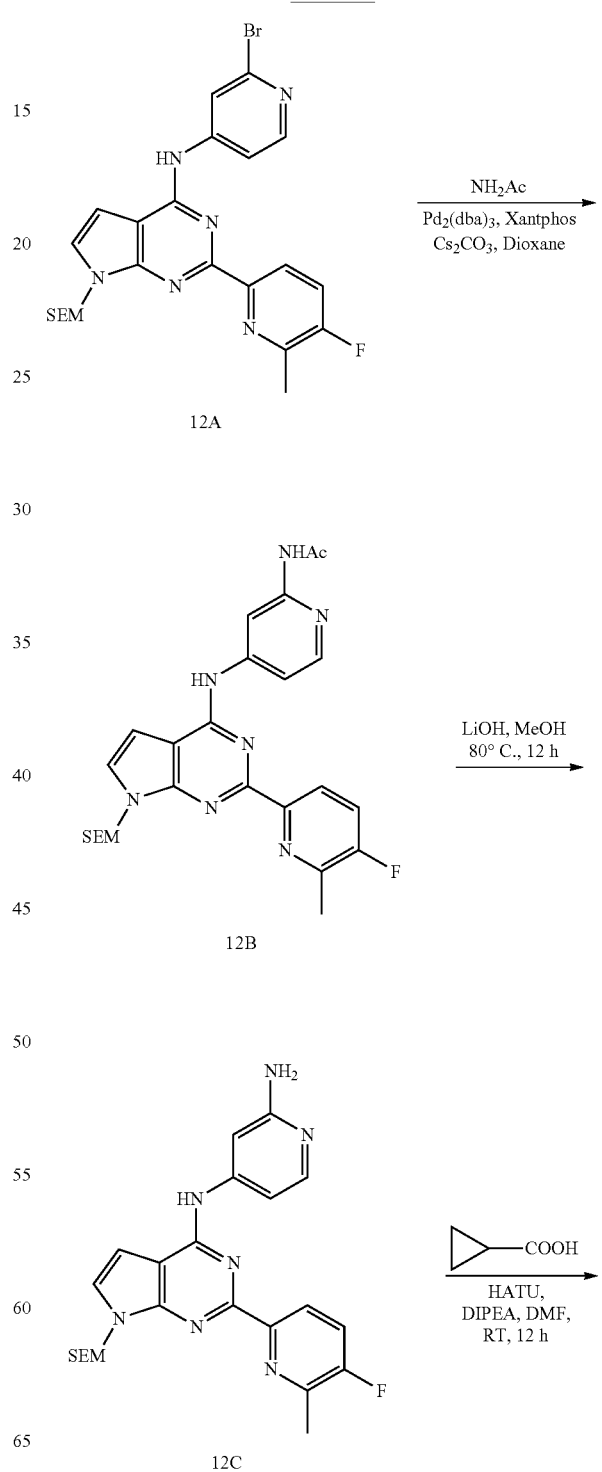

Scheme-12

85

-continued

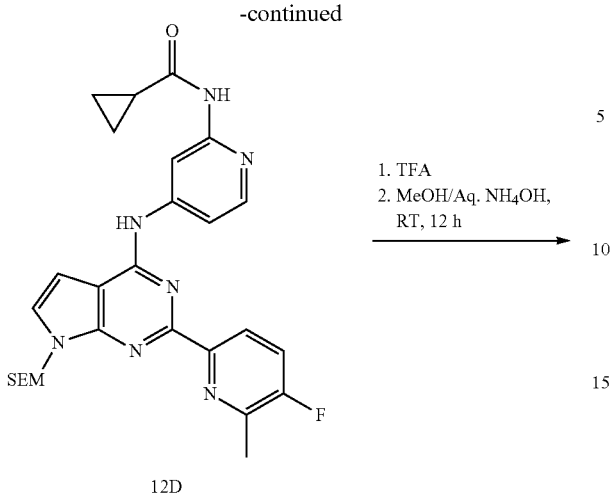

12D

1. TFA
2. MeOH/Aq. NH₄OH, RT, 12 h

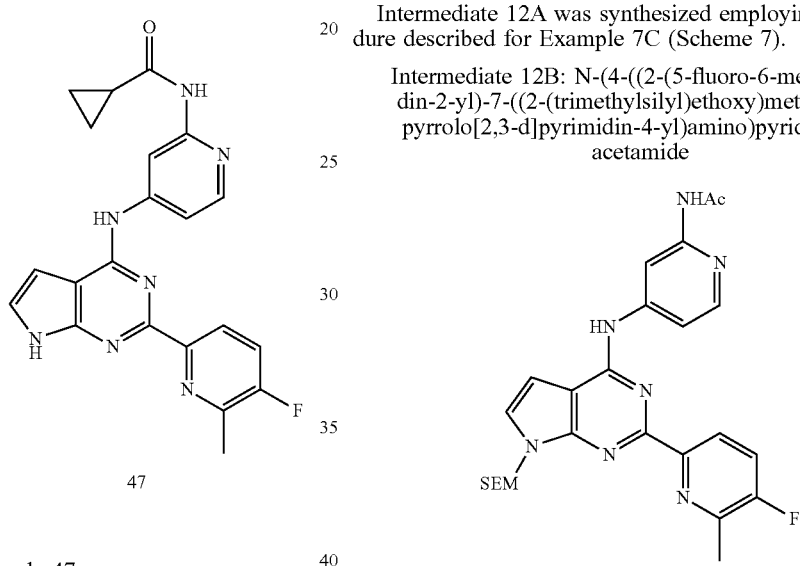

47

Example 47

N-(4-{[2-(5-fluoro-6-methylpyridin-2-yl)-7H-pyrrolo[2,3-d]pyrimidin-4-yl]amino}pyridin-2-yl)cyclopropanecarboxamide

86

Intermediate 12A: N-(2-bromopyridin-4-yl)-2-(5-fluoro-6-methylpyridin-2-yl)-7-((2-(trimethylsilyl)ethoxy)methyl)-7H-pyrrolo[2,3-d]pyrimidin-4-amine

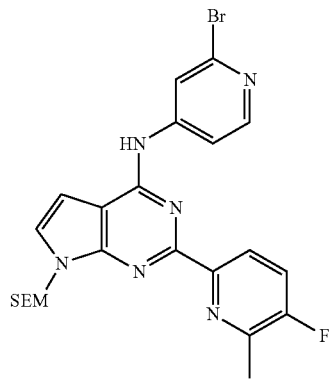 [SMILES: Cc1nc(-c2nc(Nc3ccnc(Br)c3)c3ccn(COCC[Si](C)(C)C)c3n2)ccc1F]

Intermediate 12A was synthesized employing the procedure described for Example 7C (Scheme 7).

Intermediate 12B: N-(4-((2-(5-fluoro-6-methylpyridin-2-yl)-7-((2-(trimethylsilyl)ethoxy)methyl)-7H-pyrrolo[2,3-d]pyrimidin-4-yl)amino)pyridin-2-yl)acetamide Intermediate 12B (0.15 g, 0.295 mmol, 62.6%) was synthesized employing the procedure described for Example 3 (Scheme 3). LCMS: m/z 508.4 (M+H); rt 3.02 min; Condition E.

Intermediate 12C: N4-(2-(5-fluoro-6-methylpyridin-2-yl)-7-((2-(trimethylsilyl)ethoxy)methyl)-7H-pyrrolo[2,3-d]pyrimidin-4-yl)pyridine-2,4-diamine

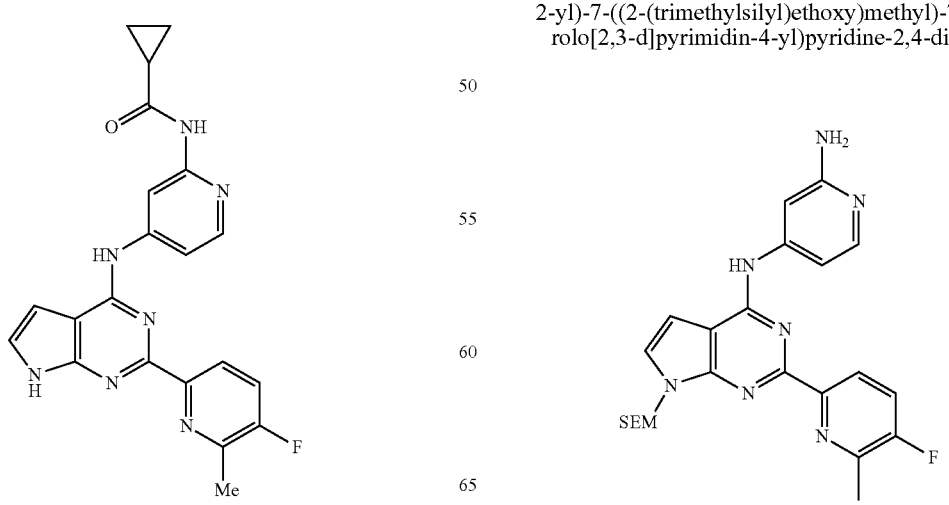

Example 12C (100.0 mg, 72.7%) was synthesized employing the procedure described for Example 4 (Scheme 4). LCMS: m/z 466.5 (M+H); rt 3.21 min; Condition E.

Intermediate 12D: Intermediate 2: N-(4-((2-(5-fluoro-6-methylpyridin-2-yl)-7-((2-(trimethylsilyl)ethoxy)methyl)-7H-pyrrolo[2,3-d]pyrimidin-4-yl)amino)pyridin-2-yl)cyclopropanecarboxamide

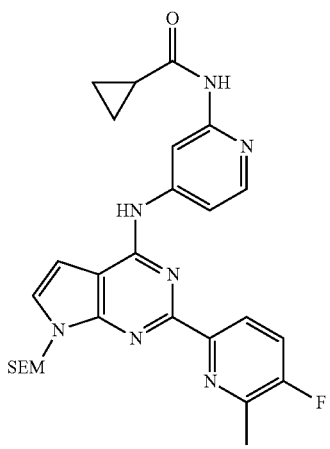 [SMILES: Cc1nc(-c2nc(Nc3ccnc(NC(=O)C4CC4)c3)c3ccn(COCC[Si](C)(C)C)c3n2)ccc1F]

Intermediate 12D (70 mg, 0.131 mmol, 76%) was synthesized employing the procedure described for Example 4C (Scheme 4). LCMS: m/z 578.2 (M+H); rt 3.853 min; condition E.

Example 47 (3 mg, 7.44 μmol, 4.96%) was synthesized employing the procedure described for Example 1 (Scheme 1). LCMS: m/z 404.1 (M+H); rt 1.54 min; Conditions C. $^1$H NMR (400 MHz, DMSO-$d_6$) δ 12.10 (s, 1H) 8.70 (d, J=1.96 Hz, 1H) 8.48 (dd, J=8.68, 4.04 Hz, 1H) 8.20 (d, J=5.62 Hz, 1H) 8.09 (dd, J=5.62, 1.96 Hz, 1H) 7.65 (t, J=8.93 Hz, 1H) 7.40 (d, J=3.18 Hz, 1H) 6.95 (dd, J=3.55, 1.59 Hz, 1H) 1.99-2.10 (m, 1H) 0.78-0.90 (m, 4H).

Example 48

N-(6-{4-[methyl(pyridin-4-yl)amino]-7H-pyrrolo[2,3-d]pyrimidin-2-yl}pyridin-2-yl)methanesulfonamide

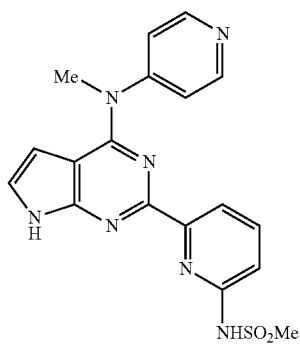

Example 48 (4.9 mg, 0.012 mmol, 12.6% yield) was synthesized employing the procedure described for Example 1 (Scheme 1). LCMS: m/z 396.2 (M+H); rt 1.05 min; Conditions G. $^1$H NMR (DMSO-d6) δ 12.11 (br. s., 1H), 8.54 (d, J=5.0 Hz, 2H), 7.83-7.98 (m, 2H), 7.36 (d, J=5.1 Hz, 2H), 7.29 (br. s., 1H), 6.96 (d, J=8.0 Hz, 1H), 5.46 (br. s., 1H).

Example 49

N-(6-{4-[(3-chloropyridin-4-yl)amino]-7H-pyrrolo[2,3-d]pyrimidin-2-yl}pyridin-2-yl)methanesulfonamide

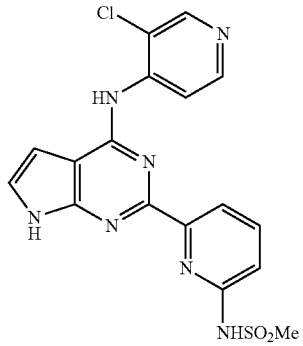

Example 49 (1.3 mg, 3.13 μmol, 3.2% yield) was synthesized employing the procedure described for Example 1 (Scheme 1). LCMS: m/z 416.1 (M+H); rt 1.23 min; Conditions G. $^1$H NMR (DMSO-d6) δ 8.61 (br. s., 2H), 8.48 (br. s., 1H), 7.75-8.01 (m, 2H), 7.47 (br. s., 1H), 6.74-7.03 (m, 2H).

Biological Assays

Assays are conducted in 1536-well plates and 2 mL reactions are prepared from addition of HIS-TGFβR1 T204D or HIS-TGFβR2 WT, anti-HIS detection antibody, a labeled small molecule probe ($K_d$=<100 nM; $k_{off}$=<0.001 s$^{-1}$.) and test compounds in assay buffer (20 mM HEPES pH 7.4, 10 mM MgCl$_2$, 0.015% Brij35, 4 mM DTT, and 0.05 mg/ml BSA). The reaction is incubated for 1 hour at room temperature and the HTRF signal was measured on an Envision plate reader (Ex: 340 nm; Em: 520 nm/495 nm). Inhibition data were calculated by comparison to no enzyme control reactions for 100% inhibition and vehicle-only reactions for 0% inhibition. The final concentration of reagents in the assay are 1 nM HIS-TGFβR1 T204D or HIS-TGFβR2 WT, 0.2 nM anti-HIS detection antibody, labeled small molecule probe (at $K_d$) and 0.5% DMSO. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

Table 1 shows the TGFβR1 and TGFβR2 IC$_{50}$ values for Examples 1-49 of this invention.

| Example# | TGFβR1 HIS T204D HTRF IC$_{50}$ (μM) | TGFβR2 HIS WT HTRF IC$_{50}$ (μM) |
| --- | --- | --- |
| 1 | 0.00070 | 0.50 |
| 2 | 0.00025 | 0.74 |
| 3 | 0.00078 | 0.19 |
| 4 | 0.00042 | >15 |

-continued

| Example# | TGFβR1 HIS T204D HTRF IC$_{50}$ (μM) | TGFβR2 HIS WT HTRF IC$_{50}$ (μM) |
|---|---|---|
| 5 | 0.00053 | >15 |
| 6 | 0.00076 | >15 |
| 7 | 0.0037 | >15 |
| 8 | 0.00026 | 0.15 |
| 9 | 0.0012 | 0.15 |
| 10 | 0.00056 | >15 |
| 11 | 0.00060 | 0.17 |
| 12 | 0.00064 | 0.59 |
| 13 | 0.0040 | >15 |
| 14 | 0.00091 | 0.24 |
| 15 | 0.16 | >15 |
| 16 | 0.00071 | >15 |
| 17 | 0.00076 | 0.10 |
| 18 | 0.0013 | >15 |
| 19 | 0.0058 | >15 |
| 20 | 0.00067 | 5 |
| 21 | 0.00090 | 0.05 |
| 22 | 0.0010 | 0.23 |
| 23 | 0.0047 | >15 |
| 24 | 0.00074 | 4.8 |
| 25 | 0.0015 | 4.1 |
| 26 | 0.0027 | >15 |
| 27 | 0.00085 | >15 |
| 28 | 0.97 | >15 |
| 29 | 0.00077 | 0.19 |
| 30 | 0.0025 | >15 |
| 31 | 0.00037 | 1.2 |
| 32 | 0.00077 | >15 |
| 33 | 0.00025 | 1.2 |
| 34 | 0.0045 | >15 |
| 35 | 0.0014 | 5.2 |
| 36 | 0.0017 | >15 |
| 37 | 0.00087 | >15 |
| 38 | 0.00059 | >15 |
| 39 | 0.00064 | >15 |
| 40 | 0.00060 | >15 |
| 41 | 0.00087 | 0.23 |
| 42 | 0.0017 | >15 |
| 43 | 0.00075 | 0.81 |
| 44 | 0.0026 | >15 |
| 45 | 0.0010 | 3.4 |
| 46 | 0.00079 | 1.8 |
| 47 | 0.0014 | 0.026 |
| 48 | 0.0043 | >15 |
| 49 | 0.0022 | >15 |

What is claimed is:

1. A compound of formula III

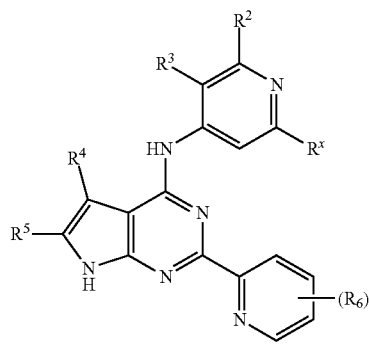

(III)

wherein:
$R^2$ is hydrogen, pyrrolidin-2-one, $NHSO_2R^7$ or $NHCOR^7$;
$R^3$ is hydrogen, halogen, $(C_1$-$C_3)$alkyl, $(C_1$-$C_3)$alkoxy, —$CONR^8R^9$ or —$OR^{10}$; or
$R^3$ and the —NH— linker group are taken together to form a 10-12 membered heterobicyclic ring containing 1-4 heteroatoms selected from —O—, —S— or —N—;
$R^4$ is $(C_1$-$C_6)$alkyl, —$CH_2NR^{11}R^{12}$ or —$CONR^{11}R^{12}$;
$R^5$ is hydrogen, —$CONHR^{13}$, —$CH_2NHR^{14}R^{15}$ or —$NHR^{14}R^{15}$;
$R^x$ is hydrogen, halogen, $(C_1$-$C_6)$alkyl or —$NHCO(C_1$-$C_6)$alkyl;
$R^6$ is hydrogen, halogen, $(C_1$-$C_6)$alkyl, $(C_1$-$C_6)$alkoxy, —$CHF_2$, —$CFH_2$, $CF_3$, $(C_3$-$C_8)$cycloalkyl, —$NH_2$ or $NHSO_2(C_1$-$C_6)$alkyl;
$R^7$ is $(C_1$-$C_6)$alkyl, $(C_1$-$C_6)$alkoxy, $(C_3$-$C_8)$cycloalkyl, heterocyclylalkyl, amino$(C_1$-$C_6)$alkyl or hydroxy$(C_1$-$C_6)$alkyl;
$R^8$ is hydrogen, $(C1$-$C_6)$alkoxy or $(C_1$-$C_6)$alkyl;
$R^9$ is hydrogen or a 5-8 membered heterocyclic ring containing 1-4 heteroatoms selected from —O—, —S— or —N—; or
$R^8$ and $R^9$ are taken together with the nitrogen to which they are attached to form a 5-8 membered heterocyclic ring containing 1-4 heteroatoms selected from —O—, —S— or —N—;
$R^{10}$ is $(C_1$-$C_6)$alkyl;
$R^{11}$ is hydrogen, amino$(C_1$-$C_6)$alkyl or hydroxy$(C_1$-$C_6)$alkyl;
$R^{12}$ is hydrogen, amino$(C_1$-$C_6)$alkyl or hydroxy$(C_1$-$C_6)$alkyl; or
$R^{11}$ and $R^{12}$ are taken together with the nitrogen to which they are attached to form a 5-8 membered heterocyclic ring containing 1-4 heteroatoms selected from —O—, —S— or —N—;
$R^{13}$ is hydrogen or $(C_1$-$C_6)$alkyl;
$R^{14}$ is hydrogen or $(C_1$-$C_6)$alkyl
$R^{15}$ is hydrogen or $(C_1$-$C_6)$alkyl; or
$R^{14}$ and $R^{15}$ are taken together with the nitrogen to which they are attached to form a 5-8 membered heterocyclic ring containing 1-4 heteroatoms selected from —O—, —S— or —N—;
n is 0, 1, 2 or 3;
or a pharmaceutically acceptable salt, tautomer or stereoisomer thereof.

2. A compound according to claim 1 of formula III

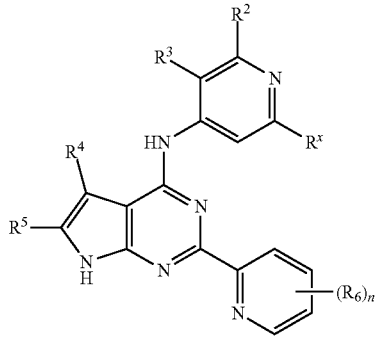

(III)

wherein:
$R^2$ is hydrogen, pyrrolidin-2-one, $NHSO_2R^7$ or $NHCOR^7$;
$R^3$ is hydrogen, halogen, $(C_1$-$C_3)$alkyl, $(C_1$-$C_3)$alkoxy, —$CONR^8R^9$ or —$OR^{10}$; or
$R^3$ and the —NH— linker group are taken together to form a 10-12 membered heterobicyclic ring containing 1-4 heteroatoms selected from —O—, —S— or —N—;

R⁴ is $(C_1-C_6)$alkyl, —CH$_2$NR$^{11}$R$^{12}$ or —CONR$^{11}$R$^{12}$;
R⁵ is hydrogen, —CONHR$^{13}$, —CH$_2$NHR$^{14}$R$^{15}$ or —NHR$^{14}$R$^{15}$;
R$^x$ is hydrogen, halogen, $(C_1-C_6)$alkyl or —NHCO$(C_1-C_6)$alkyl;
R⁶ is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;
R⁷ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;
R⁸ is hydrogen, $(C_1-C_6)$alkoxy or $(C_1-C_6)$alkyl;
R⁹ is hydrogen or a 5-8 membered heterocyclic ring containing 1-4 heteroatoms selected from —O—, —S— or —N—; or
R⁸ and R⁹ are taken together with the nitrogen to which they are attached to form a 5-8 membered heterocyclic ring containing 1-4 heteroatoms selected from —O—, —S— or —N—;
R¹⁰ is $(C_1-C_6)$alkyl;
R¹¹ is hydrogen, amino$(C_1-C_6)$alkyl or hydroxy$(C_1-C_6)$alkyl;
R¹² is hydrogen, amino$(C_1-C_6)$alkyl or hydroxy$(C_1-C_6)$alkyl; or
R¹¹ and R¹² are taken together with the nitrogen to which they are attached to form a 5-8 membered heterocyclic ring containing 1-4 heteroatoms selected from —O—, —S— or —N—;
R¹³ is hydrogen or $(C_1-C_6)$alkyl;
R¹⁴ is hydrogen or $(C_1-C_6)$alkyl
R¹⁵ is hydrogen or $(C_1-C_6)$alkyl; or
R¹⁴ and R¹⁵ are taken together with the nitrogen to which they are attached to form a 5-8 membered heterocyclic ring containing 1-4 heteroatoms selected from —O—, —S— or —N—;
n is 0, 1 or 2;
or a pharmaceutically acceptable salt, tautomer or stereoisomer thereof.

3. A compound according to claim 2 of formula III

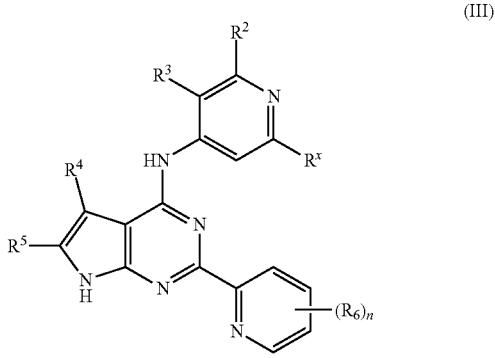

(III)

wherein:
R² is hydrogen, pyrrolidin-2-one, NHSO$_2$R⁷ or NHCOR⁷;
R³ is hydrogen, halogen, $(C_1-C_3)$alkyl, $(C_1-C_3)$alkoxy, —CONR⁸R⁹ or —OR$^{10}$; or
R³ and the —NH— linker group are taken together to form a 10-12 membered heterobicyclic ring containing 1-4 heteroatoms selected from —O—, —S— or —N—;
R⁴ is $(C_1-C_6)$alkyl, —CH$_2$NR$^{11}$R$^{12}$ or —CONR$^{11}$R$^{12}$;
R⁵ is hydrogen, —CONHR$^{13}$, —CH$_2$NHR$^{14}$R$^{15}$ or —NHR$^{14}$R$^{15}$;
R$^x$ is hydrogen, halogen, $(C_1-C_6)$alkyl or —NHCO$(C_1-C_6)$alkyl;
R⁶ is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;
R⁷ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;
R⁸ is hydrogen, $(C_1-C_6)$alkoxy or $(C_1-C_6)$alkyl;
R⁹ is hydrogen or a 5-8 membered heterocyclic ring containing 1-4 heteroatoms selected from —O—, —S— or —N—; or
R⁸ and R⁹ are taken together with the nitrogen to which they are attached to form a 5-8 membered heterocyclic ring containing 1-4 heteroatoms selected from —O—, —S— or —N—;
R¹⁰ is $(C_1-C_6)$alkyl;
R¹¹ is hydrogen, amino$(C_1-C_6)$alkyl or hydroxy$(C_1-C_6)$alkyl;
R¹² is hydrogen, amino$(C_1-C_6)$alkyl or hydroxy$(C_1-C_6)$alkyl; or
R¹¹ and R¹² are taken together with the nitrogen to which they are attached to form a 5-8 membered heterocyclic ring containing 1-4 heteroatoms selected from —O—, —S— or —N—;
R¹³ is hydrogen or $(C_1-C_6)$alkyl;
R¹⁴ is hydrogen or $(C_1-C_6)$alkyl
R¹⁵ is hydrogen or $(C_1-C_6)$alkyl; or
R¹⁴ and R¹⁵ are taken together with the nitrogen to which they are attached to form a 5-8 membered heterocyclic ring containing 1-4 heteroatoms selected from —O—, —S— or —N—;
n is 0 or 1;
or a pharmaceutically acceptable salt, tautomer or stereoisomer thereof.

4. A compound according to claim 3 wherein:
R² is hydrogen, pyrrolidin-2-one, NHSO$_2$R⁷ or NHCOR⁷;
R³ is hydrogen, halogen, $(C_1-C_3)$alkyl, $(C_1-C_3)$alkoxy, —CONR⁸R⁹ or —OR$^{10}$; or
R³ and the —NH— linker group are taken together to form a 10-12 membered heterobicyclic ring containing 1-4 heteroatoms selected from —O—, —S— or —N—;
R⁴ is $(C_1-C_6)$alkyl, —CH$_2$NR$^{11}$R$^{12}$ or —CONR$^{11}$R$^{12}$;
R⁵ is hydrogen, —CONHR$^{13}$, —CH$_2$NHR$^{14}$R$^{15}$ or —NHR$^{14}$R$^{15}$;
R$^x$ is hydrogen, halogen, $(C_1-C_6)$alkyl or —NHCO$(C_1-C_6)$alkyl;
R⁶ is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;
R⁷ is $(C_1-C_6)$alkyl, $(C_1-C_6)$alkoxy, heterocyclylalkyl, amino$(C_1-C_6)$alkyl or hydroxy$(C_1-C_6)$alkyl;
R⁸ is hydrogen, $(C_1-C_6)$alkoxy or $(C_1-C_6)$alkyl;
R⁹ is hydrogen or a 5-8 membered heterocyclic ring containing 1-4 heteroatoms selected from —O—, —S— or —N—; or
R⁸ and R⁹ are taken together with the nitrogen to which they are attached to form a 5-8 membered heterocyclic ring containing 1-4 heteroatoms selected from —O—, —S— or —N—;
R¹⁰ is $(C_1-C_6)$alkyl;
R¹¹ is hydrogen, amino$(C_1-C_6)$alkyl or hydroxy$(C_1-C_6)$alkyl;
R¹² is hydrogen, amino$(C_1-C_6)$alkyl or hydroxy$(C_1-C_6)$alkyl;

$R^{13}$ is hydrogen or $(C_1-C_6)$alkyl;
$R^{14}$ is hydrogen or $(C_1-C_6)$alkyl
$R^{15}$ is hydrogen or $(C_1-C_6)$alkyl;
n is 0 or 1;
or a pharmaceutically acceptable salt, tautomer or stereoisomer thereof.

5. A compound according to claim 4 of the formula

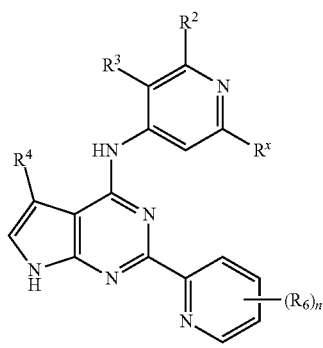

(III)

wherein:
$R^2$ is hydrogen or NHCOR$^7$;
$R^3$ is hydrogen, halogen, $(C_1-C_3)$alkyl, $(C_1-C_3)$alkoxy, —CONR$^8$R$^9$ or —OR$^{10}$;
$R^4$ is $(C_1-C_6)$alkyl, —CH$_2$NR$^{11}$R$^{12}$ or —CONR$^{11}$R$^{12}$;
$R^x$ is hydrogen, halogen, $(C_1-C_6)$alkyl or —NHCO$(C_1-C_6)$alkyl;
$R^6$ is hydrogen, halogen, $(C_1-C_6)$alkyl, $(C_1-C_6)$alkoxy, —CHF$_2$, —CFH$_2$, CF$_3$, $(C_3-C_8)$cycloalkyl, —NH$_2$ or NHSO$_2(C_1-C_6)$alkyl;
$R^7$ is $(C_1-C_6)$alkyl, $(C_1-C_6)$alkoxy, $(C_3-C_8)$cycloalkyl, heterocyclylalkyl, amino$(C_1-C_6)$alkyl or hydroxy$(C_1-C_6)$alkyl;
$R^8$ is hydrogen, $(C_1-C_6)$alkoxy or $(C_1-C_6)$alkyl;
$R^9$ is hydrogen or a 5-8 membered heterocyclic ring containing 1-4 heteroatoms selected from —O—, —S— or —N—; or
$R^8$ and $R^9$ are taken together with the nitrogen to which they are attached to form a 5-8 membered heterocyclic ring containing 1-4 heteroatoms selected from —O—, —S— or —N—;
$R^{10}$ is $(C_1-C_6)$alkyl;
$R^{11}$ is hydrogen, amino$(C_1-C_6)$alkyl or hydroxy$(C_1-C_6)$alkyl;
$R^{12}$ is hydrogen, amino$(C_1-C_6)$alkyl or hydroxy$(C_1-C_6)$alkyl;
n is 0 or 1;
or a pharmaceutically acceptable salt, tautomer or stereoisomer thereof.

6. A pharmaceutical composition which comprises a compound according to claim 1 or a pharmaceutically acceptable salt thereof and one or more pharmaceutically acceptable carriers, diluents or excipients.

7. A combination pharmaceutical product comprising a compound according to claim 1 or a pharmaceutically acceptable salt thereof together with one or more other therapeutically active agents.

8. A compound according to claim 1 or a pharmaceutically acceptable salt thereof for use in therapy.

9. A compound according to claim 1 or a pharmaceutically acceptable salt thereof for use in the treatment of diseases or conditions for which a TGFβR antagonist is indicated.

10. A compound or a pharmaceutically acceptable salt thereof for use according to claim 9, wherein the disease or condition is cancer.

11. A compound selected from
N-(3-fluoropyridin-4-yl)-2-(6-methylpyridin-2-yl)-7H-pyrrolo[2,3-d]pyrimidin-4-amine,
2-(6-(difluoromethyl)pyridin-2-yl)-N-(3-fluoropyridin-4-yl)-7H-pyrrolo[2,3-d]pyrimidin-4-amine,
N-(4-((2-(6-(difluoromethyl)pyridin-2-yl)-7H-pyrrolo[2,3-d]pyrimidin-4-yl)amino)pyridin-2-yl)acetamide,
2-(pyrrolidin-1-yl)-N-(4-((2-(6-(trifluoromethyl)pyridin-2-yl)-7H-pyrrolo[2,3-d]pyrimidin-4-yl)amino)pyridin-2-yl)acetamide,
2-(4-methylpiperazin-1-yl)-N-(4-((2-(6-(trifluoromethyl)pyridin-2-yl)-7H-pyrrolo[2,3-d]pyrimidin-4-yl)amino)pyridin-2-yl)acetamide,
2-(6-(difluoromethyl)pyridin-2-yl)-N-(3-fluoropyridin-4-yl)-5-methyl-7H-pyrrolo[2,3-d]pyrimidin-4-amine,
2-(6-(difluoromethyl)pyridin-2-yl)-N-(3-fluoropyridin-4-yl)-5-(4-methylpiperazin-1-yl)methyl)-7H-pyrrolo[2,3-d]pyrimidin-4-amine,
N-(3-fluoropyridin-4-yl)-2-(pyridin-2-yl)-7H-pyrrolo[2,3-d]pyrimidin-4-amine,
2-(pyridin-2-yl)-4-(1H-pyrrolo[3,2-c]pyridin-1-yl)-7H-pyrrolo[2,3-d]pyrimidine,
N-(3-fluoropyridin-4-yl)-2-(6-(trifluoromethyl)pyridin-2-yl)-7H-pyrrolo[2,3-d]pyrimidin-4-amine,
2-(5-fluoro-6-methylpyridin-2-yl)-N-(3-fluoropyridin-4-yl)-7H-pyrrolo[2,3-d]pyrimidin-4-amine,
2-(6-(difluoromethyl)pyridin-2-yl)-4-(1H-pyrrolo[3,2-c]pyridin-1-yl)-7H-pyrrolo[2,3-d]pyrimidine,
N-(2-chloro-5-fluoropyridin-4-yl)-2-(5-fluoro-6-methylpyridin-2-yl)-7H-pyrrolo[2,3-d]pyrimidin-4-amine,
2-(5-fluoropyridin-2-yl)-N-(3-fluoropyridin-4-yl)-7H-pyrrolo[2,3-d]pyrimidin-4-amine,
N-(2-chloropyrimidin-4-yl)-2-(6-(difluoromethyl)pyridin-2-yl)-7H-pyrrolo[2,3-d]pyrimidin-4-amine,
N-(4-((2-(6-(difluoromethyl)pyridin-2-yl)-7H-pyrrolo[2,3-d]pyrimidin-4-yl)amino)-5-fluoropyridin-2-yl)acetamide,
methyl (4-((2-(6-(difluoromethyl)pyridin-2-yl)-7H-pyrrolo[2,3-d]pyrimidin-4-yl)amino)pyridin-2-yl)carbamate,
N-(5-fluoro-4-((2-(5-fluoro-6-methylpyridin-2-yl)-7H-pyrrolo[2,3-d]pyrimidin-4-yl)amino)pyridin-2-yl)acetamide,
1-(4-((2-(6-(difluoromethyl)pyridin-2-yl)-7H-pyrrolo[2,3-d]pyrimidin-4-yl)amino)pyridin-2-yl)pyrrolidin-2-one,
N-(4-((2-(6-(trifluoromethyl)pyridin-2-yl)-7H-pyrrolo[2,3-d]pyrimidin-4-yl)amino)pyridin-2-yl)acetamide,
N-(4-((2-(pyridin-2-yl)-7H-pyrrolo[2,3-d]pyrimidin-4-yl)amino)pyridin-2-yl)acetamide,
N-(4-((2-(6-methylpyridin-2-yl)-7H-pyrrolo[2,3-d]pyrimidin-4-yl)amino)pyridin-2-yl)acetamide,
N-(4-((2-(5-(trifluoromethyl)pyridin-2-yl)-7H-pyrrolo[2,3-d]pyrimidin-4-yl)amino)pyridin-2-yl)acetamide,
N-(4-((2-(6-(trifluoromethyl)pyridin-2-yl)-7H-pyrrolo[2,3-d]pyrimidin-4-yl)amino)pyridin-2-yl)propionamide,
N-(4-((2-(6-(difluoromethyl)pyridin-2-yl)-5-methyl-7H-pyrrolo[2,3-d]pyrimidin-4-yl)amino)pyridin-2-yl)acetamide,
3,3-dimethyl-N-(4-((2-(6-(trifluoromethyl)pyridin-2-yl)-7H-pyrrolo[2,3-d]pyrimidin-4-yl)amino)pyridin-2-yl)butanamide, 3-methyl-N-(4-((2-(6-(trifluoromethyl)pyridin-2-yl)-7H-pyrrolo[2,3-d]pyrimidin-4-yl)amino)pyridin-2-yl)butanamide, N-(4-((2-(6-(trifluoromethyl)pyridin-2-yl)-7H-pyrrolo[2,3-d]pyrimidin-4-yl)amino)pyridin-2-yl)methanesulfonamide, N-(4-((2-(5-fluoro-6-methylpyridin-2-yl)-7H-pyrrolo[2,3-d]pyrimidin-4-yl)amino)pyridin-2-yl)acetamide, methyl (4-((2-(6-(trifluoromethyl)pyridin-2-yl)-7H-pyrrolo[2,3-d]pyrimidin-4-yl)amino)pyridin-2-yl)carbamate, N-(4-((2-(6-(difluoromethyl)pyridin-2-yl)-7H-pyrrolo[2,3-d]pyrimidin-4-yl)amino)-3-fluoropyridin-2-yl)acetamide, 2-morpholino-N-(4-((2-(6-(trifluoromethyl)pyridin-2-yl)-7H-pyrrolo[2,3-d]pyrimidin-4-yl)amino)pyridin-2-yl)acetamide, N-(3-fluoropyridin-4-yl)-5-methyl-2-(6-methylpyridin-2-yl)-7H-pyrrolo[2,3-d]pyrimidin-4-amine, N-(3-fluoropyridin-4-yl)-5-methyl-2-(6-(trifluoromethyl)pyridin-2-yl)-7H-pyrrolo[2,3-d]pyrimidin-4-amine, 1-(((2-(6-(difluoromethyl)pyridin-2-yl)-4-(3-fluoropyridin-4-yl)amino)-7H-pyrrolo[2,3-d]pyrimidin-5-yl)methyl)amino)-2-methylpropan-2-ol, N-[3-fluoro-4-({2-[6-(trifluoromethyl)pyridin-2-yl]-7H-pyrrolo[2,3-d]pyrimidin-4-yl}amino)pyridin-2-yl]acetamide, 3-methyl-N-{2-[6-(trifluoromethyl)pyridin-2-yl]-7H-pyrrolo[2,3-d]pyrimidin-4-yl}pyridin-4-amine, N-methyl-N-{2-[6-(trifluoromethyl)pyridin-2-yl]-7H-pyrrolo[2,3-d]pyrimidin-4-yl}pyridin-4-amine, 3-(trifluoromethyl)-N-{2-[6-(trifluoromethyl)pyridin-2-yl]-7H-pyrrolo[2,3-d]pyrimidin-4-yl}pyridin-4-amine, 3-chloro-N-{2-[6-(trifluoromethyl)pyridin-2-yl]-7H-pyrrolo[2,3-d]pyrimidin-4-yl}pyridin-4-amine, N-[4-({2-[6-(trifluoromethyl)pyridin-2-yl]-7H-pyrrolo[2,3-d]pyrimidin-4-yl}amino)pyridin-2-yl]cyclopropanecarboxamide, 3-methoxy-N-{2-[6-(trifluoromethyl)pyridin-2-yl]-7H-pyrrolo[2,3-d]pyrimidin-4-yl}pyridin-4-amine, N-[4-({2-[6-(difluoromethyl)pyridin-2-yl]-5-{[(2-hydroxy-2-methylpropyl)amino]methyl}-7H-pyrrolo[2,3-d]pyrimidin-4-yl}amino)pyridin-2-yl]acetamide, N-[4-({2-[6-(difluoromethyl)pyridin-2-yl]-5-{[(2-hydroxy-2-methylpropyl)amino]methyl}-7H-pyrrolo[2,3-d]pyrimidin-4-yl}amino)-5-fluoropyridin-2-yl]acetamide, N-[2-(5-fluoro-6-methylpyridin-2-yl)-7H-pyrrolo[2,3-d]pyrimidin-4-yl]-3-methylpyridin-4-amine, N-[2-(5-fluoro-6-methylpyridin-2-yl)-7H-pyrrolo[2,3-d]pyrimidin-4-yl]-3-methoxypyridin-4-amine, N-(4-{[2-(5-fluoro-6-methylpyridin-2-yl)-7H-pyrrolo[2,3-d]pyrimidin-4-yl]amino}pyridin-2-yl)cyclopropanecarboxamide, N-(6-{4-[methyl(pyridin-4-yl)amino]-7H-pyrrolo[2,3-d]pyrimidin-2-yl}pyridin-2-yl)methanesulfonamide, or N-(6-{4-[(3-chloropyridin-4-yl)amino]-7H-pyrrolo[2,3-d]pyrimidin-2-yl}pyridin-2-yl)methanesulfonamide, or a pharmaceutically acceptable salt thereof.

* * * * *